(12) United States Patent
Gillberg et al.

(10) Patent No.: US 11,583,539 B2
(45) Date of Patent: Feb. 21, 2023

(54) TREATING PROGRESSIVE FAMILIAL INTRAHEPATIC CHOLESTASIS (PFIC) WITH IBAT INHIBITORS

(71) Applicant: ALBIREO AB, Gothenburg (SE)

(72) Inventors: Per-Göran Gillberg, Åsbro (SE); Jan Mattsson, Gothenburg (SE); Pat Horn, Boston, MA (US); Paresh Soni, Mystic, CT (US)

(73) Assignee: Albireo AB, Gothenburg (SE)

( * ) Notice: Subject to any disclaimer, the term of this patent is extended or adjusted under 35 U.S.C. 154(b) by 0 days.

(21) Appl. No.: 17/548,090

(22) Filed: Dec. 10, 2021

(65) Prior Publication Data

US 2022/0143043 A1 May 12, 2022

Related U.S. Application Data

(63) Continuation of application No. PCT/EP2021/081462, filed on Nov. 12, 2021.

(60) Provisional application No. 63/255,719, filed on Oct. 14, 2021, provisional application No. 63/195,512, filed on Jun. 1, 2021, provisional application No. 63/185,876, filed on May 7, 2021, provisional application No. 63/152,307, filed on Feb. 22, 2021, provisional application No. 63/113,170, filed on Nov. 12, 2020.

(51) Int. Cl.
*A61K 31/554* (2006.01)
*A61P 1/16* (2006.01)
*A61K 9/16* (2006.01)

(52) U.S. Cl.
CPC .......... *A61K 31/554* (2013.01); *A61K 9/1652* (2013.01); *A61K 9/1676* (2013.01); *A61P 1/16* (2018.01)

(58) Field of Classification Search
CPC ........ A61K 9/1652; A61K 31/554; A61P 1/16
See application file for complete search history.

(56) References Cited

U.S. PATENT DOCUMENTS

| 3,539,380 A | 11/1970 | Johnson |
| 4,507,235 A | 3/1985 | Wunsch |
| 5,167,965 A | 12/1992 | Schulz |

(Continued)

FOREIGN PATENT DOCUMENTS

| DE | 3930168 | 3/1991 |
| DE | 19825804 | 8/2000 |

(Continued)

OTHER PUBLICATIONS

Slavetinsky (Oevixibat and Partial External Biliary Diversion Showed Equal Improvement of Cholestasis in a Patient with Progressive Familial Intrahepatic Cholestasis (Pediatric Gastroenterology and Hepatology. (Year: 2020).*

(Continued)

*Primary Examiner* — Carlos A Azpuru
(74) *Attorney, Agent, or Firm* — Fish & Richardson P.C.

(57) ABSTRACT

Provided herein are methods for treating progressive familial intrahepatic cholestasis (PFIC) with an ileal bile acid transport (IBAT) inhibitor such as odevixibat, or a pharmaceutically acceptable salt thereof. Such methods can include reducing mean pruritus score, mean serum bile acid concentration, increasing height, normalizing weight, improving sleep, and improving liver parameters.

29 Claims, 27 Drawing Sheets

(56) References Cited

U.S. PATENT DOCUMENTS

| | | |
|---|---|---|
| 5,384,130 A | 1/1995 | Kamada |
| 5,663,165 A | 9/1997 | Brieaddy |
| 5,723,458 A | 3/1998 | Brieaddy et al. |
| 5,811,388 A | 9/1998 | Friend et al. |
| 5,817,652 A | 10/1998 | Brieaddy et al. |
| 5,900,233 A | 5/1999 | Day |
| 5,910,494 A | 6/1999 | Brieaddy |
| 5,976,811 A | 11/1999 | Mullner et al. |
| 5,994,391 A | 11/1999 | Lee et al. |
| 5,998,400 A | 12/1999 | Brieaddy et al. |
| 6,020,330 A | 2/2000 | Enhsen et al. |
| 6,069,167 A | 5/2000 | Sokol |
| 6,277,831 B1 | 8/2001 | Frick et al. |
| 6,346,527 B1 | 2/2002 | Takanaka et al. |
| 6,355,672 B1 | 3/2002 | Yasuma et al. |
| 6,387,924 B2 | 5/2002 | Lee et al. |
| 6,387,944 B1 | 5/2002 | Frick et al. |
| 6,426,340 B1 | 7/2002 | Gibson et al. |
| 6,562,860 B1 | 5/2003 | Keller et al. |
| 6,635,280 B2 | 10/2003 | Shell et al. |
| 6,642,269 B2 | 11/2003 | Frick et al. |
| 6,676,979 B2 | 1/2004 | Marlett et al. |
| 6,784,201 B2 | 8/2004 | Lee et al. |
| 6,906,058 B2 | 6/2005 | Starke et al. |
| 6,943,189 B2 | 9/2005 | Keller et al. |
| 7,019,023 B2 | 3/2006 | Frick et al. |
| 7,125,864 B2 | 10/2006 | Starke et al. |
| 7,132,416 B2 | 11/2006 | Starke et al. |
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,615,536 B2 | 11/2009 | Frick et al. |
| 7,767,229 B1 | 8/2010 | Milne et al. |
| 7,923,468 B2 | 4/2011 | Frick et al. |
| 7,939,061 B2 | 5/2011 | Prakash et al. |
| 7,956,085 B2 | 6/2011 | Frick et al. |
| 8,048,413 B2 | 11/2011 | Huguet |
| 8,067,584 B2 | 11/2011 | Starke et al. |
| 8,101,583 B2 | 1/2012 | Glombik et al. |
| 8,106,023 B2 | 1/2012 | Glombik et al. |
| 9,295,677 B2 | 3/2016 | Ling et al. |
| 9,339,480 B2 | 5/2016 | Young et al. |
| 9,409,875 B2 | 8/2016 | Bohlin et al. |
| 9,684,018 B2 | 6/2017 | Horanzy |
| 9,688,720 B2 | 6/2017 | Gillberg et al. |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 10,000,528 B2 | 6/2018 | Gillberg et al. |
| 10,011,633 B2 | 7/2018 | Gillberg et al. |
| 10,093,697 B2 | 10/2018 | Gillberg et al. |
| 10,183,920 B2 | 1/2019 | Ymen et al. |
| 10,428,109 B1 | 10/2019 | Bhat et al. |
| 10,441,604 B2 | 10/2019 | Gillberg et al. |
| 10,441,605 B2 | 10/2019 | Gillberg et al. |
| 10,487,111 B2 | 11/2019 | Gillberg et al. |
| 10,709,755 B2 | 7/2020 | Ando et al. |
| 10,793,534 B2 | 10/2020 | Gillberg |
| 10,941,127 B2 | 3/2021 | Gilberg et al. |
| 10,975,045 B2 | 4/2021 | Gillberg et al. |
| 10,975,046 B2 | 4/2021 | Lundqvist et al. |
| 10,981,952 B2 | 4/2021 | Gilberg et al. |
| 10,995,115 B2 | 5/2021 | Bhat et al. |
| 11,014,898 B1 | 5/2021 | Gillberg et al. |
| 11,111,224 B2 | 9/2021 | Gillberg |
| 11,180,465 B2 | 11/2021 | Gillberg et al. |
| 11,261,212 B2 * | 3/2022 | Gillberg ............ A61K 38/05 |
| 11,267,794 B2 | 3/2022 | Gillberg et al. |
| 11,306,064 B2 | 4/2022 | Gillberg et al. |
| 2002/0142054 A1 | 10/2002 | Marlett et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0166927 A1 | 9/2003 | Starke et al. |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0038009 A1 | 2/2005 | Starke et al. |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2006/0083790 A1 | 4/2006 | Anderberg et al. |
| 2007/0197522 A1 | 8/2007 | Edwards et al. |
| 2008/0207592 A1 | 8/2008 | Frick et al. |
| 2008/0300171 A1 | 12/2008 | Balkan et al. |
| 2009/0131395 A1 | 5/2009 | Antonelli et al. |
| 2010/0130472 A1 | 5/2010 | Young et al. |
| 2011/0003782 A1 | 1/2011 | Pellicciari |
| 2011/0152204 A1 | 6/2011 | Gedulin et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2014/0275090 A1 | 9/2014 | Gedulin et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182059 A1 | 6/2017 | Gillberg et al. |
| 2017/0182115 A1 | 6/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0162904 A1 | 6/2018 | Gillberg et al. |
| 2018/0362577 A1 | 12/2018 | Gillberg et al. |
| 2019/0177286 A1 | 6/2019 | Ymen et al. |
| 2019/0276493 A1 | 9/2019 | Bhat et al. |
| 2019/0367467 A1 | 12/2019 | Gillberg et al. |
| 2020/0002299 A1 | 1/2020 | Lundqvist |
| 2020/0109165 A1 | 4/2020 | Bhat et al. |
| 2020/0140484 A1 | 5/2020 | Gillberg et al. |
| 2020/0247768 A1 | 8/2020 | Gillberg et al. |
| 2020/0247769 A1 | 8/2020 | Gillberg et al. |
| 2020/0330545 A1 | 10/2020 | Gillberg et al. |
| 2021/0017141 A1 | 1/2021 | Gillberg et al. |
| 2021/0024475 A1 | 1/2021 | Lundqvist |
| 2021/0147372 A1 | 5/2021 | Gillberg |
| 2021/0171479 A1 | 6/2021 | Gillberg |
| 2021/0171480 A1 | 6/2021 | Gillberg |
| 2021/0171481 A1 | 6/2021 | Gillberg |
| 2021/0171482 A1 | 6/2021 | Gillberg |
| 2021/0171483 A1 | 6/2021 | Gillberg |
| 2021/0177767 A1 | 6/2021 | Byrod |
| 2021/0179572 A1 | 6/2021 | Gillberg |
| 2021/0236511 A1 | 8/2021 | Byrod |

(56) References Cited

U.S. PATENT DOCUMENTS

| | | |
|---|---|---|
| 2021/0299141 A1 | 9/2021 | Gillberg |
| 2021/0340175 A1 | 11/2021 | Gillberg |
| 2021/0387956 A1 | 12/2021 | Gillberg |
| 2022/0041567 A1 | 2/2022 | Gillberg et al. |

FOREIGN PATENT DOCUMENTS

| | | |
|---|---|---|
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0864582 | 9/1998 |
| EP | 1173205 | 4/2000 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | B-3665055 | 6/2005 |
| JP | 2013-541584 | 11/2013 |
| JP | A-2013-542953 | 11/2013 |
| JP | H02258719 | 10/2019 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/020421 | 10/2004 |
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2013/168671 | 11/2013 |
| WO | WO 2014/174066 | 10/2014 |
| WO | WO 2016/062848 | 4/2016 |
| WO | WO 2017/138876 | 8/2017 |
| WO | WO 2017/138877 | 8/2017 |
| WO | WO 2017/138878 | 8/2017 |
| WO | WO 2019/032026 | 2/2019 |
| WO | WO 2019/032027 | 2/2019 |
| WO | WO 2019/172834 | 9/2019 |
| WO | WO 2019/234077 | 12/2019 |
| WO | WO 2019/245448 | 12/2019 |
| WO | WO 2019/245449 | 12/2019 |
| WO | 2020/16758 A1 * | 8/2020 |
| WO | WO 2020/161216 | 8/2020 |
| WO | WO 2020/161217 | 8/2020 |
| WO | WO 2020/167958 | 8/2020 |
| WO | WO 2020/167964 | 8/2020 |
| WO | WO 2020/167981 | 8/2020 |
| WO | WO 2020/167985 | 8/2020 |

OTHER PUBLICATIONS

Dury et al: Ileal Bile Acid Transporter Inhibitor for the Treatment of Chronic Constipation, Cholestatic Pruritis, and NASH, vol. 9. (Year: 2018).*

Al-Dury,"Ileal Bile Acid Transporter Inhibition for the Treatment of Chronic Constipation, Cholestatic Pruritus, and NASH," Frontiers in Pharmacology, 2018, 9:931.

International Search Report and Written Opinion in Appl. No. PCT/EP2021/081462, dated Jan. 1, 2022, 18 pages.

Sangkhathat et al., "Variants Associated with Infantile Cholestatic Syndromes Detected in Extrahepatic Biliary Atresia by Whole Exome Studies: A 20-Case Series from Thailand," J. Pediatr Genet., 2018, 7:67-73.

Slavetinsky et al., "Odevixibat and partial external biliary diversion showed equal improvement of cholestasis in a patient with progressive familial intrahepatic cholestasis," BMJ Case Rep, 2020, 13:e234185.

[No Author Listed],"Practical Pharmaceutical Preparation Technology," People's Medical Publishing House, Jan. 1999, 286-287 (Machine Translation).

"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001 &rank=7, 4 pages.

AASLD: 2017 68th Annual Meeting of the American Association for the Study of Liver Diseases, Washington, DC, Oct. 20-24, 2017, (Abstract only).

Adams et al., "Hepascore: an accurate validated predictor of liver fibrosis in chronic hepatitis C infection," Clin. Chem. 2005, vol. 51(10), p. 1867-1873.

Alagille Syndrome, Wikipedia, the free encyclopedia, posted on or about Feb. 11, 2005, retrieved Feb. 12, 2014, http://en.wikipedia.org/wiki/Alagille_syndrome, 3 pages.

(56) References Cited

OTHER PUBLICATIONS

Alashkar et al., "Meeting Info: 57th Annual Meeting of the American Society of Hematology," Orlando, FL, USA. Dec. 5-8, 2015, Amer Soc Hematol, Blood, 2015, 126(23).

"Albireo's Lead Compound in Cholestatie Liver Diseases, A4250, Projects Against Bile Acid-Mediated Cholestatie Liver Injury in Mice," Albireo Press Release, Apr. 11, 2014, 2 pages.

Alissa et al., "Invited Review: Update on Progressive Familial Intrahepatic Cholestasis," Journal of Pediatric Gastroenterology and Nutrition, 2008, 46:241-252.

Alonso et al., "Histologic pathology of the liver in progressive familial intrahepatic cholestasis," Journal of Pediatric Gastroenterology and Nutrition, 14: 128-133, 1994.

Alvarez et al., "Reduced hepatic expression of farnesoid X receptor in hereditary cholestasis associated to mutation in ATP8B1," Hum Mol Genet, 2004, 13(20):2451-2460.

Alvarez, "Development of crystallization processes for pharmaceutical applications," LACCEI, 2007, 2E.3-1-2E.3-9.

Alvarez, Fernando, "Treatments in chronic cholestasis in children," Ann. Nestlé (2008) 66 p. 127-135.

American Diabetes Association, "Management of Dyslipidemia in Adults with Diabetes," Diabetes Care, Jan. 2003, 26(1).

An Extension Study to Evaluate the Long-Term Safety and Durability of Effect of LUM001 in the Treatment of Cholestatic Liver Disease in Subjects With Alagille Syndrome (IMAGINE), Clinical Trials.gov, Jan. 23, 2014, retrieved on Oct. 3, 2014, http://clinicaltrials.gov/ct2/show/NCT02047318?term=LUM001&rank=3, 3 pages.

An Extension Study to Evaluate the Long-Term Safety and Durability of Effect of LUM001 in the Treatment of Cholestatic Liver Disease in Subjects With Alagille Syndrome (IMAGINE-II), Clinical Trials.gov, Apr. 16, 2014, retrieved on Oct. 3, 2014, http://clinicaltrials.gov/ct2/show/NCT02117713?term=LUM001&rank=2, 3 pages.

Anakk et al., "Bile acids activate YAP to promote liver carcinogenesis," Cell Rep., Nov. 27, 2013, 5(4):1060-1069.

Angulo et al., "Independent Predictors of Liver Fibrosis in Patients With Nonalcoholic Steatohepatitis," Hepatology, Dec. 1999, 30(6): 1356-1362.

Angulo et al., "The NAFLD fibrosis score: a noninvasive system that identifies liver fibrosis in patients with NAFLD," Hepatology, 2007, vol. 45(4), p. 846-54.

Angulo, "Use of ursodeoxycholic acid in patients with liver disease," Current Gastroenterology Reports, Feb. 1, 2002, 4(1):37-44.

Anzivino et al., "ABCB4 and ABCB11 mutations in intrahepatic cholestasis of pregnancy in an Italian population," Dig Liver Dis., 2013, 45(3):226-232.

Appleby et al., "Effects of conventional and a novel colonic-release bile acid sequestrant, A3384, on fibroblast growth factor 19 and bile acid metabolism in healthy volunteers and patients with bile acid diarrhoea," United Eur. Gastroent. J., vol. 5, pp. 380-388, 2017.

Arnell et al., "Follow-up in children with progressive familial intrahepatic cholestasis after partial external biliary diversion," J Pediatr Gastroenterol Nutr., 2010, 51(4):494-499.

Artursson and Karlsson, "Correlation Between Oral Drag Absorption in Humans and Apparent Drug Permeability Coefficients in Human Intestinal Epithelial (CACO-2) Cells," Biochemical and Biophysical Research Communications, Mar. 1991, 175(3):880-885.

Attili et al., "Bile Acid-induced Liver Toxicity: Relation to the Hydrophobic-Hydrophilic Balance of Bile Acids," Medical Hypotheses, 1986, 19:57-69.

Baghdasaryan et al., "Inhibition of intestinal bile acid absorption by ASBT inhibitor A4250 protects against bile acid-mediated cholestatic liver injury in mice," J. Hepatology, 2014, 60:S57.

Baghdasaryan et al., "Inhibition of intestinal bile acid absorption by ASBT inhibitor A4250 protects against bile acid-mediated cholestatic liver injury in mice," Presented at the EASL Conference, London, UK, Apr. 12, 2015, http://www.albireopharma.com/News.aspx?PageID=1591817, 22 pages.

Bajor et al., "Bile acids: short and long term effects in the intestine," Scandinavian J. Gastro., 2010, 45:645-664.

Baker et al., "Systematic review of progressive familial intrahepatic cholestasis," Clin Res Hepatol Gastroenterol., 2019;43:20-36.

Balbach et al., "Pharmaceutical evaluation of early development candidates "the 100 mg-approach"," Int J Pharm, May 4, 2004, 275(1):1-12.

Banker et al., "Modem Pharmaceutics, 3ed," Marcel Dekker, New York, 1996, pp. 451 and 596.

Baumannet al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).

Bavin, "Polymorphism in Process Development," Chemistry and Industry, 527-529, 1989.

Beausejour et al., "Description of two new ABCB11 mutations responsible for type 2 benign recurrent intrahepatic cholestasis in a French-Canadian family," Can J Gastroenterol., 2011, 25(6):311-314.

Beraza et al., "Nor-ursodeoxycholic acid reverses hepatocyte-specific nemo-dependent steatohepatitis," Gut, 2011: 60: 387-396.

Billington et al., "Effects of bile salts on the plasma membranes of isolated rat hepatocytes," Biochem. J. 188: 321-327, 1980.

Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.

Bonge et al., "Cytostar-T Scintillating Microplate Assay for Measurement of Sodium-Dependent Bile Acid Uptake in Transfected HEK-293 Cells," Analytical Biochemistiy, 2000, 282:94-101.

Bounford. University of Birmingham. Dissertation Abstracts International, (2016) vol. 75, No. IC. Order No. AA110588329. ProQuest Dissertations & Theses.

Bowel Diversion Surgeries: Ileostomy, Colostomy, Ileoanal Reservoir and Continent Ileostomy, US Department of Health and Human Services: National Institute of Diabetes and Digestive And Kidney Diseases, Feb. 2009, retrieved on Jan. 27, 2014, http://digestive.niddk.nih.gov/ddiseases/pub/ileostomy/Bowel_Diversion_508.pdf, 4 pages.

Brunt et al., "Nonalcoholic Steatohepatitis: A Proposal for Grading and Staging the Histological Lesions," American Journal of Gastroenterology, Sep. 1999, 94(9): 2467-2474.

Brunzell and Hokanson, "Dislipidemia of Central Obesity and Insulin Resistance," Diabetes Care, 1999, 22(Suppl. 3):C10-C13.

Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.

Bull et al., "Progressive Familial Intrahepatic Cholestasis," Clin Liver Dis., Nov. 2018, 22:4:657-669.

Burrows, "Interventions for treating cholestasis in pregnancy," Cochrane Database Syst. Rev., 4:CD00493, 2001.

Byrne et al., "Missense mutations and single nucleotide polymorphisms in ABCB11 impair bile salt export pump processing and function or disrupt pre-messenger RNA splicing," Hepatology, 2009, 49(2):553-567.

Caira, "Crystalline Polymorphism of Organic Compounds," in: Topics in Current Chemistry, Jan. 1998, 198:163-208.

Camilleri, "Probiotics and irritable bowel syndrome: rationale, putative mechanisms, and evidence of clinical efficacy," Clin. Gastroenterol., 40(3):264-9, Mar. 2006.

Centeno, "Molecular mechanisms triggered by low-calcium diets," Nutrition Research Reviews, 22(2):163-74, Dec. 2009.

Chalasani et al., "The diagnosis and management of nonalcoholic fatty liver disease: Practice guidance from the American Association for the Study of Liver Diseases," Hepatology, 2018, 67(1):328-357.

Chang et al., "Bile acids promote the expression of hepatitis c virus in replicon-harboring cells," Journal of Virology, Sep. 2007, 81(18):9633-9640.

Chauhan et al., "Pharmaceutical polymers," Encycl. Biomed. Polymers and Polymeric Biomaterials, 2016, 5929-5942.

Chen et al., "Bile salt export pump is dysregulated with altered farnesoid X receptor isoform expression in patients with hepatocellular carcinoma," Hepatology, 57: 4, 1530-1541, 2013.

(56) References Cited

OTHER PUBLICATIONS

Chen et al., "Diagnosis of BSEP/ABCB11 mutations in Asian patients with cholestasis using denaturing high performance liquid chromatography," J Pediatr., 2008, 153(6):825-832.

Chen et al., "FIC1 and BSEP defects in Taiwanese patients with chronic intrahepatic cholestasis with low gamma-glutamyltranspeptidase levels," Journal of Pediatrics, 2002, 140(1):119-124.

Chen et al., "Inhibition of apical sodium-dependent bile acid transporter as a novel treatment for diabetes," Am J Physiol Endocrinol Metab, 2012, 302:E68-E76.

Chen et al., "Progressive Familial Intrahepatic Cholestasis, Type 1, Is Associated with Decreased Farnesoid X Receptor Activity," Gastroenterology, 2004, 126:756-764.

Chen et al., "Serum and urine metabolite profiling reveals potential biomarkers of human hepatocellular carcinoma," Molecular and Cellular Proteomics 10.7, 2011.

Chen et al., "The effects of diets enriched in beta-glucans on blood lipoprotein concentrations," J. Clin. Lipidol., 3(3):154-8, May 2009.

Chen et al., "Treatment effect of rifampicin on cholestasis," Internet Journal of Pharmacology, 4(2), 2006.

Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.

Chiang, "Bile acids: regulation of synthesis," J. Lipid Res, 2009, 50(10):1955-1966.

Clinical Trials Identifier: NCT03566238, "A Double-Blind, Randomized, Placebo-Controlled, Phase 3 Study to Demonstrate Efficacy and Safety of A4250 in Children With Progressive Familial Intrahepatic Cholestasis Types 1 and 2 (PEDFIC 1)," version 24, Apr. 18, 2019, 8 pages.

Clinical Trials Identifier: NCT03659916, "Long Term Safety & Efficacy Study Evaluating The Effect of A4250 in Children With PFIC," version 11, Oct. 24, 2019, 7 pages.

Colorcon.com[online] "Achieving tablet stability with moisture management," retrieved on May 28, 2021, retrieved from URL<https://www.colorcon.com/connect-with-colorcon/achieving-tablet-stability-with-moisture-management>, 4 pages.

Copeland et al., "Novel splice-site mutation in ATP8B1 results in atypical progressive familial intrahepatic cholestasis type 1," J Gastroenterol Hepatol., 2013, 28(3):560-564.

Danese et al., "Analytical evaluation of three enzymatic assays for measuring total bile acids in plasma using a fully-automated clinical chemistry platform," PLoS One, 2017, 12(6):e0179200.

Das & Kar, "Non alcoholic steatohepatitis," JAPI. 53:, Mar. 2005.

Dashti et al., "A Phospholipidomic Analysis of All Defined Human Plasma Lipoproteins," Nature.com: Scientific Reports, Nov. 2011, DOI: 10.1038, 11 pages.

Davit-Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," Hepatology: Autoimmune, Cholestatic and Biliary Disease, May 2010, 1645-1655.

Davit-Spraul et al., "Liver transcript analysis reveals aberrant splicing due to silent and intronic variations in the ABCB11 gene," Mol Genet Metab., 2014, 113(3):225-229.

Davit-Spraul et al., "Progressive familial intrahepatic cholestasis," Orphanet Journal of Rare Diseases, Jan. 2009, 4:1-12.

Dawson et al., "Bile acid transporters," J. Lipid Res. 2009, 50, 2340-2357.

Dawson, "Role of the intestinal bile acid transporters in bile acid and drug disposition," Handb. Exp. Pharmacol. 2011, 201:169-203.

De Lédinghen et al., "Controlled attenuation parameter for the diagnosis of steatosis in non-alcoholic fatty liver disease," J Gastroenterol Hepatol., 2016, 31(4):848-855.

DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.

Deng et al., "Novel ATP8B1 mutation in an adult male with progressive familial intrahepatic cholestasis," World J Gastroenterol., 2012, 18(44):6504-6509.

Di Lascio et al., "Steato-Score: Non-invasive Quantitative Assessment of Liver Fat by Ultrasound Imaging," Ultrasound Med Biol., 2018, 44(8):1585-1596.

Di Padova et al., "Double-blind placebo-controlled clinical trial of microporous cholestyramine in the treatment of intra- and extrahepatic cholestasis: relationship between itching and scrum bile acids," Methods Find Exp Clin Pharmacol., Dec. 1984, 6(12):773-776 (Abstract Only).

Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.

Dong et al., "Structure-activity relationship for FDA approved drags as inhibitors of the human sodium taurocholate cotransporting polypeptide (NTCP)," Mol. Pharm. 2013, 10(3):1008-1019.

Dongiovanni et al., "Genetic Predisposition in NAFLD and NASH: Impact on Severity of Liver Disease and Response to Treatment," Curren Pharma Design, 2013, 19:5219-5238.

Droge et al., "Exon-skipping and mRNA decay in human liver tissue: molecular consequences of pathogenic bile salt export pump mutations," Sci Rep., 2016, vol. 6: 24827.

Droge et al., "Sequencing of FIC1, BSEP and MDR3 in a large cohort of patients with cholestasis revealed a high number of different genetic variants," J Hepatol. 2017, 67(6):1253-1264.

Droge et al., Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany. Jan. 22, 2016-Jan. 23, 2016.

Drumond et al., "Patients' appropriateness, acceptability, usability and preferences for pharmaceutical preparations: Results from a literature review on clinical evidence," Int. J. Pharm. 2017, 521(1-2):294-305.

EASL Clinical Practice Guidelines: Management of cholestatic liver diseases, European Assoc. for the Study of the Liver, Journal of Hepatology, 2009, 51:237-267.

Einspahr et al., "Protective role of wheat bran fiber: data from marker trials," Am. J. Med., 106(1A):32s-37s, Jan. 1999.

Eisai CO., Ltd., "Results from two phase 3 clinical trials of chronic constipation treatment GOOFICE 5 mg tablet," The Lancet Gastro & Hepat., Jul. 9, 2018, 3 pages.

Ekkehard Sturm et al., "The ileal bile acid transport inhibitor A4250 reduced pruritus and serum bile acid levels in children with cholestatic liver disease and pruritus: final results from a multiple-dose, open-label, multinational study," Hepatology 2017; 66: 646-47 (Suppl. 1). doi: 10.1002/hep.29501.

Ellinger et al., "Partial external biliary diversion in bile salt export pump deficiency: Association between outcome and mutation," World J Gastroenterol., 2017, 23(29):5295-5303.

Ellis et al., "Zebrafish abcb11b mutant reveals strategies to restore bile excretion impaired by bile salt export pump deficiency," Hepatology, 2018, 67(4)1531-1545.

Engelen et al., "Oral size perception of particles: effect of size, type, viscosity and method," J. Text. Studies 2005, 36(4):373-386.

Espenshade and Hughes, "Regulation of Sterol Synthesis in Eukaryotes," Annu. Rev. Genet., 2007, 41:401-427.

Evaluation of LUM001 in the Reduction of Pruritus in Alagille Syndrome (ITCH), Clinical Trials.gov, Feb. 5, 2014, retrieved on Oct. 3, 2014, http://clinicaltrials.gov/ct2/show/NCT02057692?term=LUM001&rank=5, 4 pages.

Evason et al., "Morphologic findings in progressive familial intrahepatic cholestasis 2 (PFIC2): correlation with genetic and immunohistochemical studies," Am J Surg Pathol., 2011, 35(5):687-696.

Extended European Search Report in European Application No. 11840392.2, dated Feb. 24, 2014, 7 pages.

Extended European Search Report in European Application No. 11840481.3, dated Feb. 13, 2014, 10 pages.

Faubion et al., "Toxic bile salts induce rodent hepatocyte apoptosis via direct activation of Fas," The Journal of Clinical Investigation, 103: 1, 137-145, 1999.

(56) References Cited

OTHER PUBLICATIONS

Ferreira et al., Pediatric Transplantation 2013, 17(SUPPL. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Fisher, "Milling of inactive pharmaceutical ingredients," Encyclopedia of Pharm. Tech., 2001, 2339-2351.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(SUPPL. 1):516, Abstract No. T.N.5.
Francalanci et al., Laboratory Investigation 2011, vol. 91, Supp. SUPPL. 1, pp. 360A. Abstract No. 1526.
Fujino et al., "Pruritus in patients with chronic liver disease and serum autotaxin levels in patients with primary biliary cholangitis," BMC Gastro., 2019, 19:169.
Gao et al., "Detection of hepatitis in children with idiopathic cholestatic bile salt export pump gene mutations," Shandong Yiyao, 2012, 52(10):14-16.
Gao et al., "Recent developments in the crystallization process: toward the pharmaceutical industry," Engineering, 2017, 3:343-353.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "Clinical Pharmacology of odevixibat, a potent, selective ileal bile acid transport inhibitor with minimal systemic exposure," Annual Meeting A4250: NASPGHAN, J Pediatr Gastroenterol Nutr., 69(suppl 2):S113 Abstract No. 166-167, 2019.
Gillberg et al., "The IBAT Inhibition by A3309—A Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human atherosclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate," Journal of Lipid Research 35(5):741-748, 1994.
Greten, "Molecular therapy for the treatment of hepatocellular carcinoma," Br. J. Cancer, 2009, 100:19-23.
Griffin et al., "A novel gene mutation in ABCB11 in siblings with progressive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of Pathology & Laboratory Medicine, Nov. 2008, 132(11):1761-1766.
Hancock et al., "Molecular mobility of amorphous pharmaceutical solids below their glass transition temperatures," Pharm. Res., 12(6): 799-806, 1995.
Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.
Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society, Astana, Kazakhstan, May 20, 2015-May 22, 2015.
Hasegawa et al., "Intractable itch relieved by 4-phenylbutyrate therapy in patients with progressive familial intrahepatic cholestasis type 1," Orphanet J Rare Dis., 2014, 9:89.
Hayashi et al., "Assessment of ATP8B1 Deficiency in Pediatric Patients With Cholestasis Using Peripheral Blood Monocyte-Derived Macrophages," EBioMedicine, 2018, 27:187-199.
Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.
Heathcote, "Management of primary biliary cirrhosis," Hepatology, 2000, 31(4):1005-1013.
hepc.liverfoundation.org [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal Na+/bile acid cotransporter by S-8921 reduces serum cholesterol and prevents atherosclerosis in rabbits," Arteriosclerosis, Thrombosis, and Vascular Biology 18(8):1304-1311, 1998.
Ho et al., "Polymorphic variants in the human bile salt export pump (BSEP; ABCB11): functional characterization and interindividual variability," Pharmacogenet Genomics, 2010, 20(1):45-57.
Hollands et al., "Ileal exclusion for Byler's disease: an alternative surgical approach with promising early results for pruritus," Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)—refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs—und Staffwechselkrankheiten mit Sektion Endoskopie—10. Herbsttagung derDeutschen Gesellschaft fur Allgemein—und Viszeralchirurgie. Hamburg, Germany. Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Nonsystemic Apical Sodium-Codependent Bile Acid Transporter Inhibitors (Part 2)," J. Med. Chem., 2005, 48:5853-5868.
IBAT inhibitor A4250 for Cholestatic Pruritus, ClinicalTrials.gov, Last updated Feb. 10, 2015, https://clinicaltrials.gov/ct2/show/NCT02360852?term=a4250&rank=1, 3 pages.

(56) References Cited

OTHER PUBLICATIONS

Imagawa et al., "Clinical phenotype and molecular analysis of a homozygous ABCB11 mutation responsible for progressive infantile cholestasis," J Hum Genet. 2018, 63(5):569-577.

Imagawa et al., "Generation of a bile salt export pump deficiency model using patient-specific induced pluripotent stem cell-derived hepatocyte-like cells," Sci Rep., 2017, 7:41806.

Imagawa et al., "Splicing analysis using induced pluripotent stem cell-derived hepatocyte-like cells generated from a patient with progressive familial intrahepatic cholestasis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.

Initiation of a Phase II Trial for A4250, the Company's Lead Compound for Cholestatic Liver Diseases and NASH, Albireo Pharma Press Release, Feb. 5, 2015, http://www.alberiopharma.com/News.aspx7PageID=1600872, 2 pages.

International Preliminary Report on Patentability for Application No. PCT/JP2015/068240, dated Jan. 5, 2017, 12 pages (with English translation).

International Preliminary Report on Patentability for International Application No. PCT/EP2015/074573, dated Apr. 25, 2017, 8 pages.

International Preliminary Report on Patentability for International Application No. PCT/SE2011/051335, dated May 23, 2011, 7 pages.

International Preliminary Report on Patentability for International Application No. PCT/SE2011/051336, dated May 23, 2013, 10 pages.

International Search Report and Written Opinion for Application No. PCT/EP2014/058432, dated Jul. 11, 2014, 9 pages.

International Search Report and Written Opinion for Appln. No. PCT/EP2019/064602, dated Aug. 9, 2019, 10 pages.

International Search Report and Written Opinion for International Application No. PCT/EP2015/074573, dated Apr. 28, 2016, 11 pages.

International Search Report and Written Opinion for International Application No. PCT/SE2011/051335, dated Feb. 3, 2012, 12 pages.

International Search Report and Written Opinion for International Application No. PCT/SE2011/051366, dated Feb. 22, 2012, 18 pages.

International Search Report and Written Opinion in Appln. No. PCT/EP2021/071618, dated Oct. 4, 2021, 13 pages.

International Search Report and Written Opinion in Appln. No. PCT/SE2019/050603, dated Sep. 18, 2019, 11 pages.

International Search Report and Written Opinion in International Application No. PCT/SE2018/050802, dated Oct. 26, 2018, 14 pages.

International Search Report and Written Opinion in International Application No. PCT/SE2018/050803, dated Oct. 26, 2018, 14 pages.

International Search Report and Written Opinion in International Appln. No. PCT/EP2020/052940, dated Mar. 23, 2020, 12 pages.

International Search Report and Written Opinion in International Appln. No. PCT/EP2020/052942, dated Mar. 23, 2020, 9 pages.

International Search Report, Application No. PCT/JP2015/068240, dated Sep. 15, 2015, 11 pages (with English translation).

Ishak et al., "Histological grading and staging of chronic hepatitis," J. Hepatol. 1995, vol. 22, p. 696-699.

Ishibashi et al., "Hypercholesterolemia in low density lipoprotein receptor knockout mice and its reversal by adenovirus-mediated gene delivery," Journal of Clinical Investigation 92(2):883-893, 1993.

Ivashkin et al., "A novel mutation of ATP8B1 gene in young patient with familial intrahepatic cholestasis," Hepatology International 2016, 10(1):S461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.

Jacquet et al., "Alagille Syndrome in Adult Patients: It is Never Too Late," American Journal of Kidney Diseases, May 2007, 49(5):705-709.

Jankowska et al., "Cholestatic liver disease in children," Przegl. Epidemiol., 56:16-21, 2002.

Jankowska et al., "Ileal exclusion in children with progressive familial intrahepatic cholestasis," J Pediatr Gastroenterol Nutr. 2014,58(1):92-95.

Jansen et al., "Endogenous bile acids as carcinogens," Journal of Hepatology, Sep. 2007, 47(3):434-435.

Jaquotot-Haerranz et al., "Clinical variability of mutations in the ABCB11 gene: a case report," Rev Esp Enferm Dig., 2013, 105(1):52-54.

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jiang et al., "Non alcoholic steatohepatitis a precursor for hepatocellular carcinoma development," World Journal of Gastroenterology: WJG, Nov. 28, 2014, 20(44):16464-16473.

Jirsa et al., "Indel in the FIC1/ATP8B1 gene—a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kamath et al, "Potential of ileal bile acid transporter inhibition as a therapeutic target in Alagille syndrome and progressive familial intrahepatic cholestasis," Liver Int., Aug. 2020, 40:8:1812-1822.

Kang et al., "Progressive Familial Intrahepatic Cholestasis in Korea: A Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):5397. Meeting Info.: 80th Annual Scientific Meeting of the American-College-of-Gastroenterology. Honolulu, HI, USA. Oct. 16-21, 2015.

Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Knisely et al., "Hepatocellular Carcinoma in ten children under five years of age with bile salt export pump deficiency," Hepatology, Aug. 2006, 44(2):478-486.

Kooistra et al., "KLIFS: A structural kinase-ligand interaction database," Nucleic Acids Res., 2016, vol. 44, No. DI, pp. D365-D371.

Korman et al., "Assessment of Activity in Chronic Active Liver Disease," New England Journal of Medicine, 2010, 290(25):1399-1402.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

Krawczyk et al., "Prolonged cholestasis triggered by hepatitis A virus infection and variants of the hepatocanalicular phospholipid and bile salt transporters," Ann Hepatol., 2012, 11(5):710-744.

Kremer et al., "Serum autotaxin is increased in pruritus of cholestasis, but not of other origin, and responds to therapeutic interventions," Hepatology, Oct. 2012, 56:4:1391-400.

(56) References Cited

OTHER PUBLICATIONS

Kumar and Tandon, "Use of ursodeoxycholic acid in liver diseases," J. Gastroenterology and Hepatology, 2001, 16:3-14.
Kumar et al., "Cholestatic presentation of chronic hepatitis C," Dig. Dis.Sci, 2001, 46(10):2066-2073.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Kurbegov et al., "Biliary diversion for progressive familial intrahepatic cholestasis: Improved liver morphology and bile acid profile," Gastroenterology, 125: 4, 1227-1234, 2003.
Lam et al., "A patient with novel ABCB11 gene mutations with phenotypic transition between BRIC2 and PFIC2," J Hepatol. 2006, 441):240-242.
Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.
Lang et al.,. "Genetic variability, haplotype structures, and ethnic diversity of hepatic transporters MDR3 (ABCB4) and bile salt export pump (ABCB11)," Drug Metab Dispos. 2006, 34(9):1582-1599.
Lang et al., "Mutations and polymorphisms in the bile salt export pump and the multidrug resistance protein 3 associated with drug-induced liver injury," Pharmacogenet Genomics, 2007, 17(1):47-60.
Lanzini et al., "Intestinal absorption of the bile acid analogue $^{75}$Se-homocholic acid-taurine is increased in primary biliary cirrhosis and reverts to normal during ursodeoxycholic acid administrations," Gut, 2003, 52:1371-1375.
Lee et al., "Early Diagnosis of ABCB11 Spectrum Liver Disorders by Next Generation Sequencing," Pediatr Gastroenterol Hepatol Nutr. 2017, 20(2):114-123.
Lewis et al., "Effects of 2164U90 on ileal bile acid adsorption and serum cholesterol in rats and mice," Journal of Lipid Research 36(5):1098-1105, 1995.
Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180, Abstract No. OP284.
Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.
Li et al., "Effect of Resistant Starch Film Properties on the Colon-Targeting Release of Drug From Coated Pellets," 152 J Control. Rel. e5, 2011.
Lichtinghagen et al., "The Enhanced Liver Fibrosis (ELF) score: normal values, influence factors and proposed cut-off values," J Hepatol. Aug. 2013;59(2):236-42.
Lin et al., "Clinical and genetic analysis of an infant with progressive familial intrahepatic cholestasis type II]," Zhongguo Dang Dai Er Ke Za Zhi. 2018, 20(9)758-764 (with English abstract).
Ling, "Congenital cholestatic syndromes: What happens when children grow up?" Can J Gastroenterol, Nov. 11, 2007, 21(11):743-751.
Liu et al., "ABCB11 gene mutations in Chinese children with progressive intrahepatic cholestasis and low gamma glutamyltransferase," Liver International 2010, 30(6):809-815.
Liu et al., "Association of variants of ABCB11 with transient neonatal cholestasis," Pediatr Int. 2013, 55(2):138-144.
Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.
Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.
Liu et al., "Homozygous p.Ser267Phe in SLC10A1 is associated with a new type of hypercholanemia and implications for personalized medicine," Scientific Reports, 2017, 7(9214):1-7.
Liu, et al., "Patient-centered pharmaceutical design to improve acceptability of medicines: similarities and differences in paediatric and geriatric populations," Drugs 2014, 74(16):1871-1889.
Loh et al., "Overview of milling techniques for improving the solubility of poorly water-soluble drags," Asian J Pharm Sci., 2015, 10:225-274.
Longo et al., "Hyperlipidemia in chronic cholestatic liver disease," Curr. Treat. Options Gastrenterol., 2001, 4:111-114.
Lopez et al., "Effect of formulation variables on oral grittiness and preferences of multiparticulate formulations in adult volunteers," Eur. J. Pharm. Sci. 2016, 92:156-162.
Lopez et al., "Formulation approaches to pediatric oral drag delivery: benefits and limitations of current platforms," Expert Opin. Drug Deliv., 2015, 12(11):1727-1740.
Lumena Pharmaceuticals Now Dosing Patients in the INDIGO Phase 2 Clinical Trial of LUM001 in Pediatric Patients with Progressive Familial Intrahepatic Cholestasis, PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
Lv et al., "Noninvasive Quantitative Detection Methods of Liver Fat Content in Nonalcoholic Fatty Liver Disease," J Clin Transl Hepatol. 2018, 6(2):217-221.
Lykavieris et al., "Outcome of liver disease in children with Alagille syndrome: a study of 163 patients," Gut, 2001, 49:431-435.
Maggiore et al., "Relapsing features of bile salt export pump deficiency after liver transplantation in two patients with progressive familial intrahepatic cholestasis type 2," J Hepatol. 2010, 53(5):981-6.
Manghat and Wierzbicki, "Colesevelam hydrochloride: a specifically engineered bile acid sequestrant," Future Lipidology, 3(3):237-255, Jun. 2008.
Masahata et al., "Recurrence of Progressive Familial Intrahepatic Cholestasis Type 2 Phenotype After Living-donor Liver Transplantation: A Case Report," Transplant Proc. 2016, 48(9):3156-3162.
Massei et al., "Cholestasis as a presenting feature of acute Epstein-Barr virus infection," The pediatric Infectious Disease J., Feb. 2001, 5 pages.
Matte et al., "Analysis of gene mutations in children with cholestasis of undefined etiology," J Pediatr Gastroenterol Nutr. 2010, 51(4):488-493.
McCullough et al., "The epidemiology and risk factors of NASH," Blackwell Publishing, Chapter 3, 2005.
McKay et al., "Mutation detection in cholestatic patients using microarray resequencing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst., 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
MerckManuals.com, "Obesity," 2008, Merck Manual for Health Care Professionals, Section—Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Michielsen et al., "Viral hepatitis and hepatocellular carcinoma," World Journal of Surg. Oncol, May 2005, 3(27):1-18.
Miloh et al., Gastroenterology, Meeting Info.: Digestive Disease Week Meeting/107th Annual Meeting of the American Gastroenterological Association. Los Angeles, CA, USA. May 2006, 130:(4)(2): A759-A760.

(56) References Cited

OTHER PUBLICATIONS

Mishra et al., "Investigation of organoleptic characteristics in the development of soft chews of calcium carbonate as mineral supplement," Yakugaku Zasshi 2009, 129(12):1537-1544.

Mistry et al., "Evidence of acceptability of oral paediatric medicines: a review," J. Pharm. Pharmacol. 2017, 69(4):361-376.

Mizuochi et al., "Characterization of urinary bile acids in a pediatric BRIC-1 patient: effect of rifampicin treatment," Clin Chim Acta. 2012, 413(15-16):1301-1304.

Moghadamrad et al., "Cholestasis in a patient with gallstones and a normal gamma-glutamyl transferase," Hepatology, 2013, 57(6):2539-2541.

Morissette et al., "High-throughput crystallization: polymorphs, salts, co-crystals and solvates of pharmaceutical solids," Advanced Drug Delivery Reviews, 2004, 56:275-300.

Morotti et al., "Progressive Familial Intrahepatic Cholestasis (PFIC) Type 1, 2, and 3: A Review of the Liver Pathology Findings," Seminars in Liver Disease, Feb. 2011, 31(1):3-10.

Mouzaki and Allard, "Non-alcoholic steatohepatitis: the therapeutic challenge of a global epidemic," Annals of Gastroenterology, 2012, 25: 207-217.

Mowat et al., "Respiratory chain complex III [correction of complex] in deficiency with pruritus: a novel vitamin responsive clinical feature," J. Pediatr., 134(3):352-4, Mar. 1999.

Mwesigwa et al., "An investigation into moisture barrier film coating efficacy and its relevance to drug stability in solid dosage forms," Int. J. of Pharmacies, Jan. 2016, 497:70-77.

Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.

Nagase et al., "Preparation of Benzothiazepine derivatives with activity of bringing about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.

Narchi et al., "Intrahepatic cholestasis in two Omani siblings associated with a novel homozygous ATP8B1 mutation, c.379C>G (p. L127V)," Saudi J Gastroenterol. 2017, 23(5):303-305.

Neuman, et al., "Biomarkers in nonalcoholic fatty liver disease," Can. J. Gastroenterol. Hepatol. 2014, 28(11):607-618.

Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.

No Author, "EASL Clinical Practice Guidelines: management of cholestatic liver diseases," J. Hepatol., Aug. 2009, 51:2:237-67.

Noe et al., "Impaired expression and function of the bile salt export pump due to three novel ABCB11 mutations in intrahepatic cholestasis," J Hepatol. 2005, 43(3):536-543.

O'Neill et al., "Comparison of efficacy of plant stanol ester and sterol ester: short-term and longer-term studies," American Journal of Cardiology, 96(1A):29d-36D, Jul. 2005.

Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89 (English Translation).

Open Label Study to Evaluate Efficacy and Long Term Safety of LUM001 in the Treatment of Cholestatic Liver Disease in Patients With Progressive Familial Intrahepatic Cholestasis (INDIGO), Clinical Trials.gov, Feb. 5, 2014, retrieved on Oct. 3, 2014, http://clinicaltrials.gov/ct2/show/NCT02057718?term=LUM001&rank=4, 3 pages.

Open Label Study to Evaluate Safety and Efficacy of LUM001 in Patients With Primary Sclerosing Cholangitis (CAMEO), Clinical Trials.gov, Feb. 11, 2014, retrieved Oct. 3, 2014, http://clinicaltrials.gov/ct2/show/NCT02061540?term=LUM001&rank=6, 3 pages.

Painter et al., "Sequence variation in the ATP8B1 gene and intrahepatic cholestasis of pregnancy," Eur J Hum Genet. 2005, 13(4):435-439.

Park et al., "Clinical and ABCB11 profiles in Korean infants with progressive familial intrahepatic cholestasis," World J Gastroenterol., 2016, 22(20):4901-4907.

Parker et al., "Molecular mechanisms underlying bile acid-stimulated glucagon-like peptide-1 secretion," British J. Pharmacology, 2012, 165:414-423.

Patani et al., "Bioisosterism: A Rational Approach in Drug Design," Chem Rev, 1996, 96:3147-3176.

Pauli-Magnus et al., "Enterohepatic transport of bile salts and genetics of cholestasis," Journal of Hepatology, 2005, 43(2):342-357.

Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.

PCT International Search Report and Written Opinion in Application No. PCT/SE2019/050208, dated Jul. 8, 2019, 15 pages.

PCT International Search Report and Written Opinion in International Appln No. PCT/EP2020/084569, dated Mar. 9, 2021, 13 pages.

PCT International Search Report and Written Opinion in International Appln. No. PCT/EP2020/084567, dated Feb. 11, 2021, 13 pages.

PCT International Search Report and Written Opinion in International Appln. No. PCT/EP2020/084568, dated Feb. 11, 2021, 13 pages.

PCT International Search Report and Written Opinion in International Appln. No. PCT/EP2020/084570, dated Feb. 11, 2021, 13 pages.

PCT International Search Report and Written Opinion in International Appln. No. PCT/EP2020/084571, dated Feb. 4, 2021, 14 pages.

Peng et al., "[Relationship between phenotype and genotype of ABCB11 deficiency in siblings and literature review]," Zhonghua erke za zhi (Chinese Journal of Pediatrics) 2018, 56(6):440-444.

Perez et al., "Bile-acid-induced cell injury and protection," World J Gastroenterol, Apr. 2009, 15(14)1677-1689.

Perumpail et al., "Clinical epidemiology and disease burden of nonalcoholic fatty liver disease," World Journal of Gastroenterology, Dec. 2017, 23(47): 8263-8276.

Phase 2 Study to Evaluate LUM001 in Combination With Ursodeoxycholic Acid in Patients With Primary Biliary Cirrhosis (CLARIFY),Clinical Trials.gov, Jul. 17, 2013, retrieved Oct. 3, 2014, http://clinicaltrials.gov/ct2/show/NCT01904058?term=LUM001&rank=8, 3 pages.

Plump et al., "Severe hypercholesterolemia and atherosclerosis in apolipoprotein E-deficient mice created by homologous recombination in ES cells", Cell (71):343-353, 1992.

Podesta et al., "Treatment of pruritus of primary biliary cirrhosis with rifampin," Dig. Dis. Sci, 1991, 36(2):216-220.

Poupon et al., "Chronic Cholestatic Disease," J. Hepatology, 2000, 32(1):12-140.

Progressive familial intrahepatic cholestasis, Wikipedia, the free encyclopedia, posted on or about Feb. 24, 2006, http://en.wikipedia.org/wiki/Progressive_familial_intrahepatic_cholestasis, 3 pages.

Qiu et al., "Defects in myosin VB are associated with a spectrum of previously undiagnosed low γ-glutamyltransferase cholestasis," Hepatology 2017, 65(5)1655-1669.

Qiu et al., "Disruption of BSEP function in HepaRG cells alters bile acid disposition and is a susceptive factor to drug-induced cholestatic injury," Mol. Pharmaceutics, 13:4,, 2016 (Abstract only).

Rancaniello, "How many viruses on earth?" Virology Blog, Sep. 2013, 6 pages.

Reeder et al., "Quantitative assessment of liver fat with magnetic resonance imaging and spectroscopy," J Magn Reson Imaging. 2011, 34(4):729-749.

Renga et al., "Role of FXR in regulating bile acid homeostasis and relevance for human diseases," Curr. Drug. Targets Immune Endocr. Metabol. Disord., 5(3):289-303, Sep. 2005.

(56) References Cited

OTHER PUBLICATIONS

Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Ricci, "Bridging studies in support of oral pediatric formulation development," Int. J. Pharmaceuticals, 2013, 457:323-326.
Rolo et al., "Bile acids affect liver mitochondrial bioenergetics: Possible relevance for cholestasis therapy," Toxicological Sciences, 57: 177-185, 2000.
Rumbo et al., Transplantation 2018, vol. 102, No. 7, Supp. Supplement 1, pp. S848. Abstract No. P.752. Meeting Info: 27th International Congress of The Transplantation Society, TTS 2018. Madrid, Spain. Jun. 30, 2018-Jul. 5, 2018.
Ryder, "Guidelines for the diagnosis and treatment of hepatocellular carcinoma (HCC) in adults," Gut, May 2003, 52:(Suppl.111):iii1-iii8.
Safety and Efficacy Study of LUM001 in the Treatment of Cholestatic Liver Disease in Patients With Alagille Syndrome (IMAGO), Clinical Trials.gov, Jul. 16, 2013, http://clinicaltrials.gov/ct2/show/NCT01903460?term=LUM001 &rank=1, 3 pages.
Sanyal et al., "The etiology of hepatocellular carcinoma and consequences of treatment," The Oncologist, 2010, 15 Suppl 4, 14-22.
Satapathy and Sanyal, "Epidemiology and Natural History of Nonalcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):S177. Meeting Info.: International Liver Congress/ 52nd Annual Meeting of the European Association for the Study of the Liver, Amsterdam, Netherlands, Apr. 19-23, 2017, European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American Gastroenterological Association. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer, "Primary Biliary Cirrhosis," Proc. R. Soc. Med., Dec. 1967, 60:1257-1260.
Schiller, "Review article: the therapy of constipation," Alimentary Pharmacology and Therapeutics 15(6):749-763, 2001.
Schumpelick et al., "[Ulcerative colitis—late functional results of ileal pouch-anal anastomosis]," Chirurg, 69(10):1013-19, Oct. 1998.
Sciveres. "Relapsing features of bile salt export pump (BSEP) deficiency in a patient successfully transplanted for progressive familial intrahepatic cholestasis type 2 (PFIC2)," Digestive and Liver Disease 2010, 42(5):S329. Abstract No. CO18. Meeting Info: 17th National Congress SIGENP. Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drag Absortption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?" Liver International: Official Journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drug polymorphism and dosage form design: a practical perspective," Adv Drug Deliv Rev, Feb. 23, 2004, 56(3):335-347.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing com oil but not milk fat," J. Nutrition (US) 132(6):1269-1274, 2002.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stein, "Managing Dyslipidemia in the High-Risk Patient," Am J. Cardiol., 2002, 89:50-57.
Sterling et al., "Steatohepatitis: Risk factors and impact on disease severity in human immunodeficiency viras/hepatitis c virus coinfection," Hepatology, Apr. 2008, 47(4) 1118-1127.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology, 2008, 134(4):1203-1214.
Sun et al., "Bile acids promote diethylnitrosamine-induced hepatocellular carcinoma via increased inflammatory signaling," American Journal of Physiology—Gastrointestinal and Liver Physiology, May 5, 2016, 311(1):G91-104.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Office Action in SW Appln. No. 1950463-8, dated Sep. 26, 2019, 3 pages.
Swedish Office Action in SW Appln. No. 1950464-6, dated Sep. 26, 2019, 3 pages.
Swedish Office Action in Swedish Appln. No. 1850761-6, dated Dec. 17, 2018, 8 pages.
Swedish Office Action in Swedish Appln. No. 1850762-4, dated Dec. 27, 2018, 7 pages.
Swedish Search Report for Swedish Appln. No. 1850915-8, dated Feb. 15, 2019, 2 pages.
Swedish Search Report in SW Appln. No. 1950463-8, dated Sep. 26, 2019, 2 pages.
Swedish Search Report in SW Appln. No. 1950464-6, dated Sep. 26, 2019, 3 pages.

(56) References Cited

OTHER PUBLICATIONS

Swedish Search Report in Swedish Appln. No. 1850761-6, dated Dec. 17, 2018, 3 pages.
Swedish Search Report in Swedish Appln. No. 1850762-4, dated Dec. 27, 2018, 3 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Thebaut et al., "An update on the physiopathology and therapeutic management of cholestatic pruritus in children," Clinics and Res in Hepatology and Gastro., 2018, 42:2:103-109.
Tian et al., "Factors affecting crystallization of hydrates," J. Pharm. Pharmacol., 2010, 62:1534-1546.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in Japanese patients with intrahepatic cholestasis associated with low gamma-glutamyl transpeptidase level," Journal of Pediatric Gastroenterology and Nutrition 2018, 67(1):S363, Abstract No. 615.
Tollefson et al., "A novel class of apical sodium co-dependent bile acid transporter inhibitors: the 1,2-Benzothiazepines," Bioorganic and Medicinal Chemistry Letters 12:3727-3730, 2003.
Trauner et al., " Inflammation-induced cholestasis," J. of Gastroenterology and Hepatology, Dec. 2001, 14:10:946-959.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology, 2004, 127(2):379-384.
Van Tilberg et al., "Na+-dependent bile acid transport in the ileum: the balance between diarrhea and constipation," Gastroenterology 98(1):25-32, 1989.
Van Wessel et al., "Genotype correlates with the natural history of severe bile salt export pump deficiency," Multicenter Study., Jul. 2020, 73:1:84-93.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.

Vippagunta et al., "Crystalline solids," Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm. 2017, 536(2):547-562.
Walsh et al., "Respiratory syncytial and other virus infections in persons with chronic cardiopulmonary disease," American Journal of Respiratory Critical Care Med., 1999, 160:791-795.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific Reports, Dec. 1, 2016, 6:38180, 9 pages.
Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.
Welberg et al., "Calcium and the prevention of colon cancer," Scandinavian J. Gasteroenterology Suppl. 188:52-59, 1991.
"What is Alagille Syndrome?" European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Whitington et al., "Partial external diversion of bile for the treatment of intractable pruritus associated with intrahepatic cholestasis," Gastroenterology, 95: 1, 130-136, 1988 (Abstract only).
Williams et al., "Foye's Principles of Medicinal Chemistry," 5th Edition, 2002, 59-63.
Wolff, "Burger's Medicinal Chemistry, 5ed, Part I," John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and Alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly, 2017, 17(2):e43500.
Zhang et al., "Abcb11 deficiency induces cholestasis coupled to impaired B-Fatty acid oxidation in mice," Journal of Biological Chemistry, 287: 29, 24784-2479, 2012.
Zhang et al., "Effect of bile duct ligation on bile acid composition in mouse serum and liver," Liver Int, 32: 1, 58-69, 2012.

(56) References Cited

OTHER PUBLICATIONS

Board of Appeal of European Patent Office, Case No. T 077/08-3. 3.01, dated May 24, 2011, 17 pages.
Boncristani et al., Respiratory Viruses, Encyclopedia of Microbiology, 2009, 19 pages.
Byrn et al., "Pharmaceutical Solids: A Strategic Approach to Regulatory Considerations," Pharmaceutical Research, 1995, 12(7), pp. 945-954.
Almasio et al., "Role of S-adenosyl-L-methionine in the treatment of intrahepatic cholestasis," Drugs, 1990, 40 Suppl (3):111-123.
Asami et al., "Treatment of children with familial hypercholesterolemia with colestilan, a newly developed bile acid-binding resin," Atherosclerosis, 2002, 164:381-2.
Baringhaus, "Substrate specificity of the ileal and the hepatic Na+/bile acid cotransporters of the rabbit. II. A reliable 3D QSAR pharmacophore model for the ileal Na+/bile acid cotransporter," J. Lipid Res., 1999, 40:2158-2168.
Bass et al., "Inherited Disorders of Cholestasis in Adulthood," Clin. Liver. Dis. (Hoboken), 2013, 2(5):200-203.
Charach et al., "The association of bile acid excretion and atherosclerotic coronary artery disease," Therapeutic Advances in Gastroenterology, 2011, 4(2):95-101.
Ellis et al. "Feedback regulation of human bile acid synthesis," Falk Symposium, 2005, 141:73-79.
Farmer et al., "Currently available hypolipidaemic drugs and future therapeutic developments," Baillieres Clin Endocrinol Metab, 1995, 9(4):825-47.
Glueck, "Colestipol and probucol: treatment of primary and familial hypercholesterolemia and amelioration of atherosclerosis," Ann. Intern. Med, Apr. 1982, 96(4): 475-82.
Guo et al., "Serum Metabolomic Analysis of Coronary Heart Disease Patients with Stable Angina Pectoris Subtyped by Traditional Chinese Medicine Diagnostics Reveals Biomarkers Relevant to Personalized Treatments," Frontiers in Pharmacology, Jun. 2022, 12: 1-14.
Hofmann, "Defective Biliary Secretion during Total Parenteral Nutrition," J. Ped. Gastro, & Nutr, May 1995, 20(4):376-390.
Khurana et al., "Bile Acids Regulate Cardiovascular Function," Clin Transl Sci, Jun. 2011, 4(3):210-218.
Mehl et al. "Liver transplantation and the management of progressive familial intrahepatic cholestasis in children," World J. Transplant, 2016, 6(2):278-90.
Schonherr, "Profound Methyl Effects in Drug Discovery and a Call for New C—H Methylation Reactions," Angew. Chem. Int. Ed., 2013, 52: 12256-12267.
Vasavan et al., "Heart and bile acids—Clinical consequences of altered bile acid metabolism," BBA—Molecular Basis of Disease, 2018, 1864:1345-1355.

\* cited by examiner

| | Placebo n=20 | Odevixibat 40 µg/kg/day n=23 | Odevixibat 120 µg/kg/day n=19 | Odevixibat, All Doses n=42 |
|---|---|---|---|---|
| Age, mean (SD), y | 3.8 (3.9) | 3.9 (3.7) | 5.2 (4.2) | 4.5 (3.9) |
| Sex, female, n (%) | 8 (40.0) | 12 (52.2) | 11 (57.9) | 23 (54.8) |
| PFIC type, n (%) | | | | |
| PFIC1 | 5 (25.0) | 7 (30.4) | 5 (26.3) | 12 (28.6) |
| PFIC2 | 15 (75.0) | 16 (69.6) | 14 (73.7) | 30 (71.4) |
| UDCA at baseline, n (%) | 18 (90.0) | 19 (82.6) | 13 (68.4) | 32 (76.2) |
| Rifampicin at baseline, n (%) | 17 (85.0) | 13 (56.5) | 11 (57.9) | 24 (57.1) |
| Serum bile acids, mean (range), µmol/L | 247.5 (56.5–435) | 254.5 (76–605) | 249.2 (36–599.5) | 252.1 (36–605) |
| Pruritus score, mean (range) | 3.0 (1.9–4.0) | 3.0 (2.0–4.0) | 2.8 (1.6–3.4) | 2.9 (1.6–4.0) |
| Serum ALT, mean (range), U/L | 76.9 (19–236) | 127.7 (21–798) | 89.1 (16–314) | 110.2 (16–798) |
| Total serum bilirubin, mean (range), mg/dL | 3.1 (0.3–11.4) | 3.1 (0.3–12.7) | 3.3 (0.2–18.6) | 3.2 (0.2–18.6) |

FIG. 3

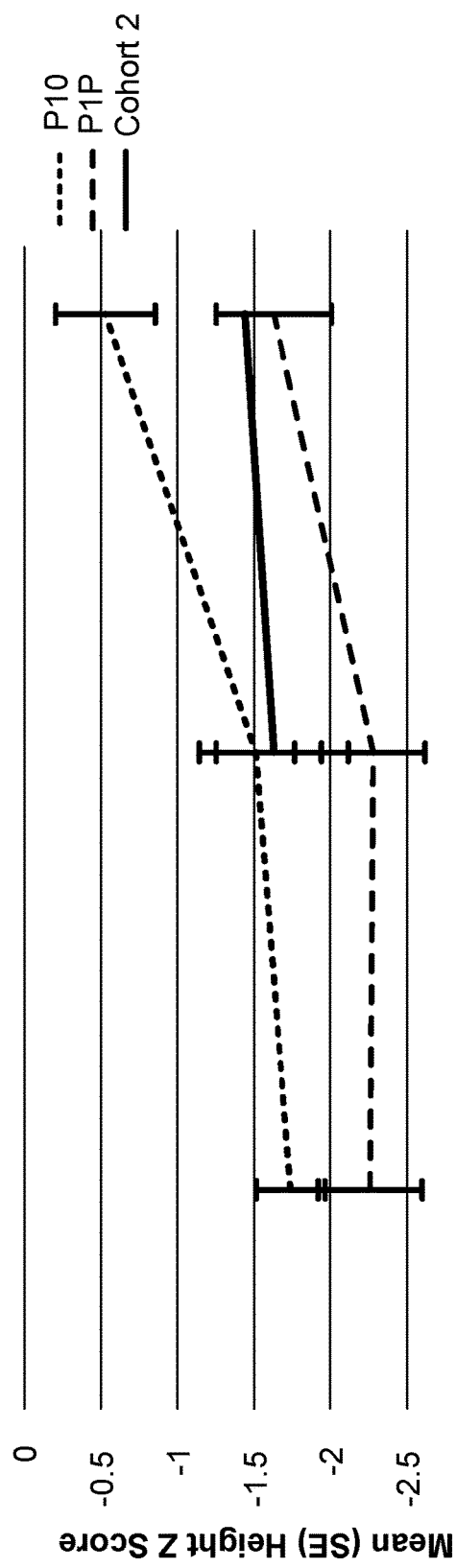
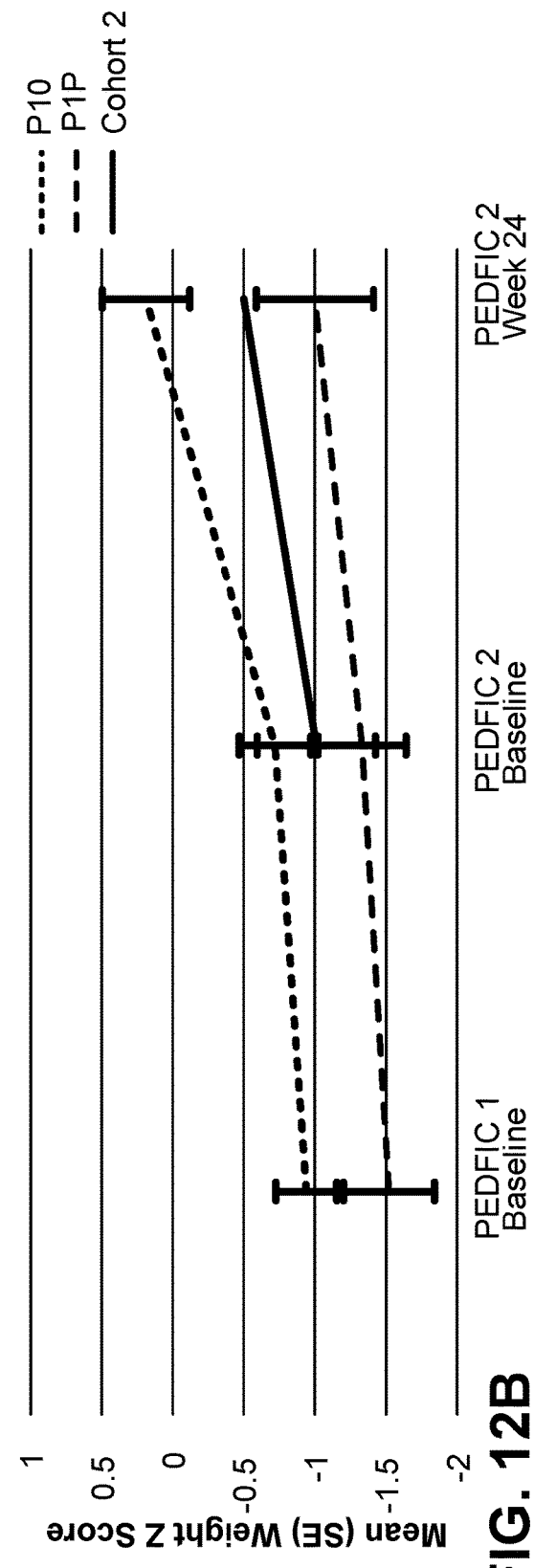
FIG. 12A
FIG. 12B

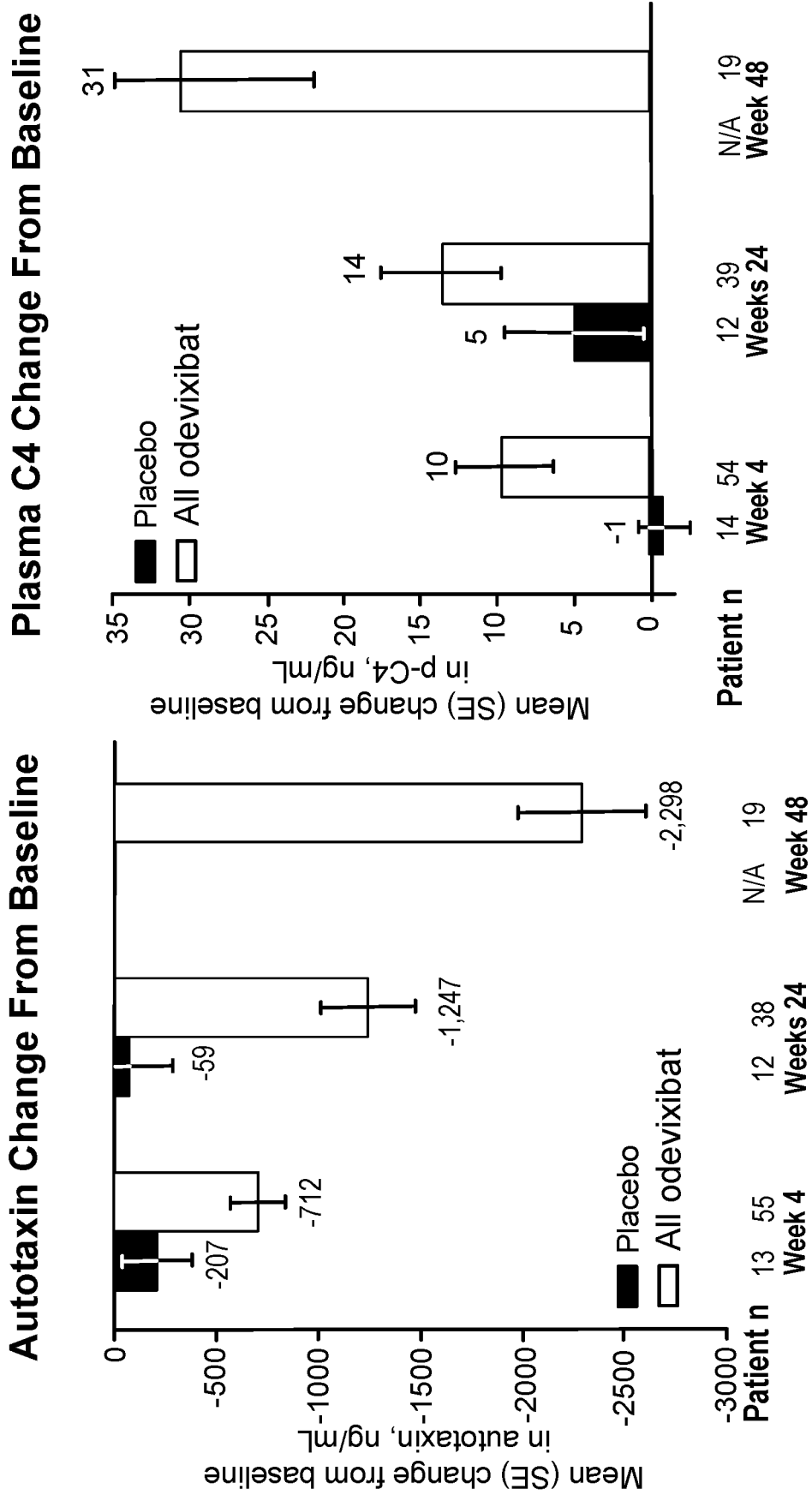

TREATING PROGRESSIVE FAMILIAL INTRAHEPATIC CHOLESTASIS (PFIC) WITH IBAT INHIBITORS

CROSS-REFERENCE TO RELATED APPLICATIONS

This application is a continuation of International Application No. PCT/EP2021/081462, filed on Nov. 12, 2021, which claims priority to U.S. Provisional Application No. 63/113,170 filed on Nov. 12, 2020, U.S. Provisional Application No. 63/152,307 filed on Feb. 22, 2021, U.S. Provisional No. 63/185,876 filed on May 7, 2021, U.S. Provisional Application No. 63/195,512 filed on Jun. 1, 2021, and U.S. Provisional Application No. 63/255,719 filed on Oct. 14, 2021, the disclosures of which are incorporated herein by reference in their entireties.

TECHNICAL FIELD

Provided herein are methods for treating progressive familial intrahepatic cholestasis (PFIC) with an ileal bile acid transport (IBAT) inhibitor such as odevixibat, or a pharmaceutically acceptable salt thereof. Such methods can include reducing mean pruritus score, mean serum bile acid concentration, increasing height, normalizing weight, improving sleep, and improving liver parameters.

BACKGROUND

The compound 1,1-dioxo-3,3-dibutyl-5-phenyl-7-methylthio-8-(N-{(R)-α-[N—((S)-1-carboxypropyl) carbamoyl]-4-hydroxybenzyl}carbamoylmethoxy)-2,3,4,5-tetrahydro-1,2,5-benzothiadiazepine (odevixibat; also known as A4250):

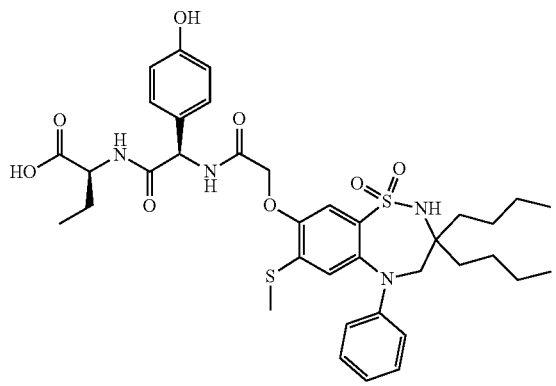 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1]

is an inhibitor of the ileal bile acid transport (IBAT) mechanism. Specifically, odevixibat inhibits the natural reabsorption of bile acids from the ileum into the hepatic portal circulation. Bile acids that are not reabsorbed from the ileum are instead excreted into the feces. The overall removal of bile acids from the enterohepatic circulation leads to a decrease in the level of bile acids in serum and the liver. Odevixibat, or a pharmaceutically acceptable salt thereof, is therefore useful in the treatment of liver diseases that are associated with elevated bile acid levels, and particularly in the treatment of rare paediatric cholestatic liver diseases including progressive familial intrahepatic cholestasis (PFIC).

SUMMARY

Provided herein are methods for treating progressive familial intrahepatic cholestasis (PFIC) or other inherited cholestatic liver diseases such as Alagille syndrome (ALGS), in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean monthly pruritus score.

Also provided herein are methods for treating pruritus associated with PFIC or other inherited cholestatic liver disease in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean monthly pruritus score.

Further provided herein are methods for reducing mean monthly pruritus score in a subject having PFIC or inherited cholestatic liver disease, the methods comprising orally administering to the subject a therapeutically effective amount of a pharmaceutical formulation comprising odevixibat, or a pharmaceutically acceptable salt thereof.

In some embodiments, provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean serum bile acid concentration.

Also provided herein are methods for treating pruritus associated with PFIC or other inherited cholestatic liver disease in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean serum bile acid concentration.

Further provided herein are methods for reducing mean serum bile acid concentration in a subject having PFIC, the methods comprising orally administering to the subject a therapeutically effective amount of a pharmaceutical formulation comprising odevixibat, or a pharmaceutically acceptable salt thereof.

Provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation for at least 24 weeks, the subject exhibits a serum bile acid concentration of less than 70 μmol/L.

Also provided herein are methods for treating pruritus associated with PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation for at least 24 weeks, the subject exhibits a serum bile acid concentration of less than 70 μmol/L.

Further provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation for at least 24 weeks, the subject exhibits a reduction in serum bile acid concentration of at least 50% relative to baseline.

In some embodiments, provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation for at least 24 weeks, the subject exhibits a reduction in serum bile acid concentration of at least 50% relative to baseline.

Also provided herein are methods for reducing serum bile acid concentrations by at least 50% relative to baseline in a subject having PFIC, the method comprising orally administering to the subject a therapeutically effective amount of a pharmaceutical formulation comprising odevixibat, or a pharmaceutically acceptable salt thereof, for at least 24 weeks.

Further provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits an increase in mean height Z score relative to baseline.

Provided herein are methods for treating pruritus associated with PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits an increase in mean height Z score relative to baseline.

Also provided herein are methods for increasing mean height Z score relative to baseline in a subject having PFIC, the methods comprising orally administering to the subject a therapeutically effective amount of a pharmaceutical formulation comprising odevixibat, or a pharmaceutically acceptable salt thereof.

Further provided herein are methods for treating PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits an increase in mean weight Z score.

In some embodiments, provided herein are methods for treating pruritus associated with PFIC in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation, the subject exhibits an increase in mean weight Z score.

Also provided herein are methods for increasing mean weight Z score in a subject having PFIC in a subject in need thereof, the methods comprising orally administering to the subject a therapeutically effective amount of a pharmaceutical formulation comprising odevixibat, or a pharmaceutically acceptable salt thereof.

Further provided herein are methods of treating progressive familial intrahepatic cholestasis 2 (PFIC2) in a subject in need thereof, the methods comprising orally administering to the subject a therapeutically effective amount of a pharmaceutical formulation comprising odevixibat, or a pharmaceutically acceptable salt thereof, wherein following administration of the pharmaceutical formulation for at least 48 weeks, the subject exhibits a serum bile acid concentration below the threshold for PFIC2 disease modification.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 provides the baseline characteristics for patients in this study.

FIG. 12 shows the effect of odevixibat on growth parameters (12A: mean height Z score; B: mean weight Z score) during PEDFIC1 and through PEDFIC2 week 24. Values shown for PEDFIC1 baseline represent all patients from PEDFIC1 (treated with odevixibat in PEDFIC1, n=42; treated with placebo in PEDFIC1, n=20); values shown for PEDFIC2 timepoints represent only patients in PEDFIC2 (P1O, n=34; P1P, n=19; cohort 2, n=16). Cohort 2, newly enrolled patients in PEDFIC2; P1O, PEDFIC2 participants who received odevixibat (combined 120 and 40 μg/kg/day dose groups) in the preceding PEDFIC1 study; P1P, PEDFIC2 participants who received placebo in the preceding PEDFIC1 study.

FIG. 14A-14D show that treatment with odevixibat was associated with rapid improvement in sBAs, pruritus, autotaxin, and p-C4 levels, respectively.

DETAILED DESCRIPTION

Definitions

Figure 1:
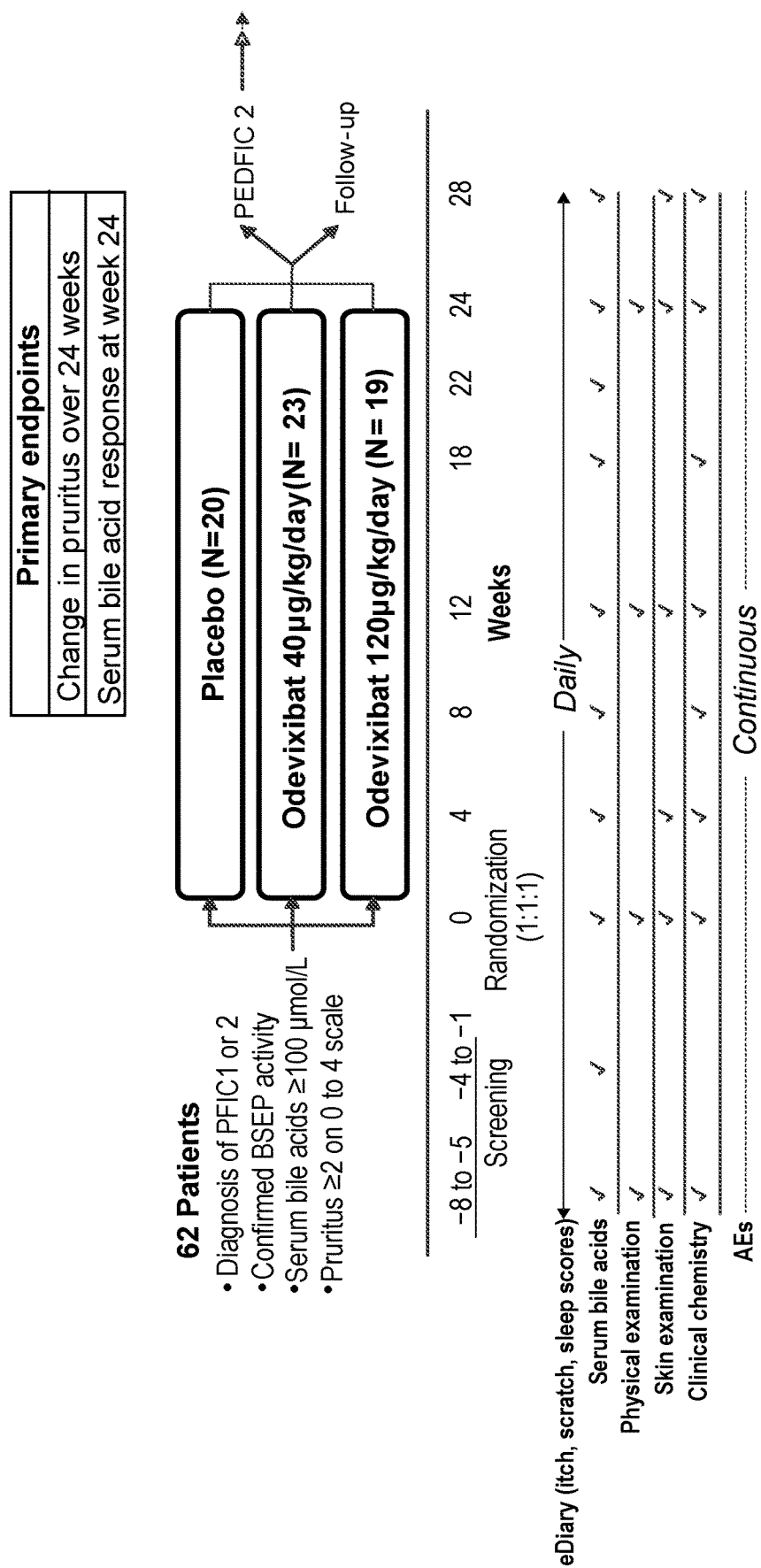
FIG. 1 provides a schematic of the study design and eligibility criteria for PEDFIC 1. The primary endpoint of change in pruritus over 24 weeks was based on the proportion of a patient's positive pruritus assessments (defined as a scratching score of ≤1 or at least a 1-point drop from baseline on an observer-reported instrument). The primary endpoint of serum bile acid (sBa) response at week 24 was defined as a ≥70% reduction from baseline in fasting sBas or sBAs ≤70 μmol/L compared with placebo.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "subject," "individual," or "patient," used interchangeably, refer to any animal, including mammals such as mice, rats, other rodents, rabbits, dogs, cats, swine, cattle, sheep, horses, primates, and humans. In some embodiments, the subject is a human.

The term "pediatric" as used herein refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E, *Textbook of Pediatrics*, 15th Ed. Philadelphia: W.B. Saunders Company, 1996; Rudolph A M, et al., *Rudolph's Pediatrics*, 21st Ed. New York: McGraw-Hill, 2002; and Avery M D, First L R, *Pediatric Medicine*, 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

As used herein, the term "baseline" refers to information obtained prior to the first administration of the drug or intervention of interest (e.g., at the beginning of a study) or an initial known value that is used for comparison with later data. Baseline values are taken at time "zero" (i.e., before subjects in a study receive the drug or intervention of interest or placebo).

As used herein, the term "normalized" refers to age-specific values that are within a range corresponding to a healthy individual (i.e., normal or normalized values).

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The term "crystal modification" refers to a crystalline solid phase of an organic compound. A crystal modification can be either a solvate or an ansolvate.

The term "solvate" refers to a crystalline solid phase of an organic compound, which has solvent (i.e., solvent molecules) incorporated into its crystal structure. A "hydrate" is a solvate wherein the solvent is water.

The term "sesquihydrate" refers to a hydrate containing about 1.5 moles of water associated with the crystal per mole of organic compound (i.e., a 1.5 hydrate). As used herein, a sesquihydrate includes from about 1.2 to about 1.8, for example, from about 1.3 to about 1.7, about 1.4 to about 1.6, or about 1.45 to about 1.55 moles of water associated with each mole of odevixibat in a crystal. The amount of water calculated herein excludes water adsorbed to the surface of the crystal.

The term "mixed solvate" refers to a crystalline solid phase of an organic compound, which has two or more different solvent molecules incorporated into its crystal structure. One of the at least two solvent molecules may be water.

The term "slurry" refers to a saturated solution to which an excess of solid is added, thereby forming a mixture of solid and saturated solution.

As used herein, the term "void volumes" refers to channels, layers or other more or less isolated voids in the crystal structure.

The crystallinity of a crystalline sample of odevixibat may be measured e.g. by X-Ray Powder Diffraction (XRPD) methods or by Differential Scanning calorimetry (DSC) methods, such as the method disclosed in the experimental section. When reference is made herein to a crystalline compound, the crystallinity as measured by DSC methods is greater than about 70%, such as greater than about 80%, particularly greater than about 90%, more particularly greater than about 95%. In some embodiments, the degree of crystallinity as measured by DSC methods is greater than about 98%. In some embodiments, the degree of crystallinity as measured by DSC methods is greater than about 99%. The % crystallinity refers to the percentage by weight of the total sample mass which is crystalline.

Methods of Treating PFIC

PFIC is a rare genetic disorder that is estimated to affect between one in every 50,000 to 100,000 children born worldwide and causes progressive, life-threatening liver disease.

One manifestation of PFIC is pruritus, which often results in a severely diminished quality of life. In some cases, PFIC leads to cirrhosis and liver failure. Current therapies include Partial External Biliary Diversion (PEBD) and liver transplantation, however, these options can carry substantial risk of post-surgical complications, as well as psychological and social issues.

Three alternative gene defects have been identified that correlate to three separate PFIC subtypes known as types 1, 2 and 3.

- PFIC, type 1, which is sometimes referred to as "Byler disease," is caused by impaired bile secretion due to mutations in the ATP8B1 gene, which codes for a protein that helps to maintain an appropriate balance of fats known as phospholipids in cell membranes in the bile ducts. An imbalance in these phospholipids is associated with cholestasis and elevated bile acids in the liver. Subjects affected by PFIC, type 1 usually develop cholestasis in the first months of life and, in the absence of surgical treatment, progress to cirrhosis and end-stage liver disease before the end of the first decade of life.
- PFIC, type 2, which is sometimes referred to as "Byler syndrome," is caused by impaired bile salt secretion due to mutations in the ABCB11 gene, which codes for a protein known as the bile salt export pump, that moves bile acids out of the liver. Subjects with PFIC, type 2 often develop liver failure within the first few years of life and are at increased risk of developing a type of liver cancer known as hepatocellular carcinoma.
- PFIC, type 3, which typically presents in the first years of childhood with progressive cholestasis, is caused by mutations in the ABCB4 gene, which codes for a transporter that moves phospholipids across cell membranes.
- PFIC, type 6, resulting from mutation of the gene encoding myosin 5B (MYO5B).

In addition, TJP2 gene and NR1H4 gene mutations have been proposed to be causes of PFIC. However, some subjects with PFIC do not exhibit a mutation in any of the ATP8B1, ABCB11, ABCB4, TJP2, NR1H4 or MYO5B genes. In these cases, the cause of the condition is unknown.

Another progressive inherited cholestatic liver disease that impacts children includes Alagille syndrome (ALGS), a rare, inherited cholestatic liver disease that typically presents within the first 3 months of life. Clinical features of ALGS can include mild to end-stage liver disease and pruritus, with up to 88% of patients presenting with pruritus and up to 45% having severe pruritus. As with PFIC, current therapies include surgery (PEBD) and liver transplantation. No medical therapy is currently available for the treatment of ALGS.

Provided herein are methods for treating PFIC or other inherited cholestatic liver disease in a subject in need thereof, the method comprising orally administering to the subject a therapeutically effective amount of a pharmaceutical formulation comprising odevixibat, or a pharmaceutically acceptable salt thereof. Also provided herein are methods for treating pruritus associated with PFIC in a subject in need thereof, the method comprising orally administering to the subject a therapeutically effective amount of a pharmaceutical formulation comprising odevixibat, or a pharmaceutically acceptable salt thereof.

Also provided herein is a pharmaceutical formulation comprising odevixibat, or a pharmaceutically acceptable salt thereof, for use in treating PFIC or other inherited cholestatic liver disease, and for use in treating pruritus associated with PFIC.

Also provided herein is the use of a pharmaceutical formulation comprising odevixibat, or a pharmaceutically acceptable salt thereof, for use in the manufacture of a medicament for the treatment of PFIC or other inherited cholestatic liver disease, and for the treatment of pruritus associated with PFIC.

Odevixibat, as referred to herein, includes solvates and hydrates thereof. For example, odevixibat can be present as a hydrate (e.g., a sesquihydrate).

In some embodiments, following administration of odevixibat, or a pharmaceutically acceptable salt thereof, the subject exhibits a reduction in mean monthly pruritus score.

In some embodiments, the reduction in mean monthly pruritus score is at least 0.5, at least 0.6, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, or at least 2.0. For example, the reduction in mean monthly pruritus score is about 0.5 to about 2.0 (e.g., about 0.5 to about 1.5; about 0.5 to about 1.2; about 0.8 to about 1.4; about 0.9 to about 1.2; about 1.2 to about 2.0; about 1.2 to about 1.5; about 1.2 to about 1.8; about 1.4 to about 2.0; about 1.6 to about 2.0; about 1.5 to about 2.0; about 1.3 to about 1.6; and about 1.4 to about 1.8). In some embodiments, the reduction in mean monthly pruritus score is about 1.1. In some embodiments, the reduction in mean monthly pruritus score is about 1.6.

In some embodiments, the reduction in mean monthly pruritus score occurs following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the reduction in mean monthly pruritus score occurs following administration of odevixibat, or a pharmaceutically acceptable salt thereof, for at least 4 weeks, at least 8 weeks, at least 12 weeks, at least 16 weeks, at least 20 weeks, or at least 24 weeks. In some embodiments, the reduction in mean monthly pruritus score occurs following 4 weeks of administration. In some embodiments, the reduction in mean monthly pruritus score occurs following 24 weeks of administration. In some embodiments, the reduction in mean monthly pruritus score occurs following 48 weeks of administration. In some embodiments, the reduction in mean monthly pruritus score occurs following 72 weeks of administration.

In some embodiments, the reduction in mean monthly pruritus score is about 0.5 to about 1.5 following 24 weeks of administration of odevixibat, or a pharmaceutically acceptable salt thereof. For example, the reduction in mean monthly pruritus score is about 0.9 to about 1.3 following 24 weeks of administration of odevixibat, or a pharmaceutically acceptable salt thereof. In some embodiments, the reduction in mean monthly pruritus score is about 1.1 following 24 weeks of administration of odevixibat, or a pharmaceutically acceptable salt thereof.

In some embodiments, the reduction in mean monthly pruritus score is about 1.2 to about 2.0 following 48 weeks of administration of odevixibat, or a pharmaceutically acceptable salt thereof. For example, the reduction in mean monthly pruritus score is about 1.4 to about 1.8 following 48 weeks of administration of odevixibat, or a pharmaceutically acceptable salt thereof. In some embodiments, the reduction in mean monthly pruritus score is about 1.6 following 48 weeks of administration of odevixibat, or a pharmaceutically acceptable salt thereof.

In some embodiments, the mean monthly pruritus score is normalized following administration of odevixibat, or a pharmaceutically acceptable salt thereof. In some embodiments, the mean monthly pruritus score is normalized following 48 weeks of administration of odevixibat, or a pharmaceutically acceptable salt thereof.

In some embodiments, the subject exhibits a reduction in mean serum bile acid concentration.

In some embodiments, the reduction in mean serum bile acid concentration is at least 50 µmol/L, at least 75 µmol/L, at least 100 µmol/L, at least 125 µmol/L, at least 150 µmol/L, or at least 175 µmol/L relative to baseline. For example, the reduction in mean serum bile acid concentration is about 50 µmol/L to about 180 µmol/L relative to baseline (e.g., about 50 µmol/L to about 100 µmol/L; about 50 µmol/L to about 120 µmol/L; about 50 µmol/L to about 150 µmol/L; about 65 µmol/L to about 120 µmol/L; about 50 µmol/L to about 90 µmol/L; about 65 µmol/L to about 85 µmol/L; about 100 µmol/L to about 130 µmol/L; about 100 µmol/L to about 180 µmol/L; and about 150 µmol/L to about 180 µmol/L). In some embodiments, the reduction in mean serum bile acid concentration of about 70 µmol/L to about 120 µmol/L relative to baseline. In some embodiments, the reduction in mean serum bile acid concentration is about 150 µmol/L to about 180 µmol/L.

In some embodiments, the reduction in mean serum bile acid concentration occurs following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the reduction in mean serum bile acid concentration occurs following administration of odevixibat, or a pharmaceutically acceptable salt thereof, for at least 4 weeks, at least 8 weeks, at least 12 weeks, at least 16 weeks, at least 20 weeks, or at least 24 weeks. In some embodiments, the reduction in mean serum bile acid concentration occurs following 4 weeks of administration. In some embodiments, the reduction in mean serum bile acid concentration occurs following 12 weeks of administration. In some embodiments, the reduction in mean serum bile acid concentration occurs following 24 weeks of administration. In some embodiments, the reduction in mean serum bile acid concentration occurs following 48 weeks of administration. In some embodiments, the reduction in mean serum bile acid concentration occurs following 72 weeks of administration.

In some embodiments, the reduction in mean serum bile acid concentration is about 50 μmol/L to about 90 μmol/L following 12 weeks of administration of odevixibat, or a pharmaceutically acceptable salt thereof. For example, the reduction in mean serum bile acid concentration is about 65 μmol/L to about 85 μmol/L following 12 weeks of administration of odevixibat, or a pharmaceutically acceptable salt thereof. In some embodiments, the reduction in mean serum bile acid concentration is about 70 (e.g., about 73) following 12 weeks of administration of odevixibat, or a pharmaceutically acceptable salt thereof.

In some embodiments, the reduction in mean serum bile acid concentration is about 100 μmol/L to about 130 μmol/L following 24 weeks of administration of odevixibat, or a pharmaceutically acceptable salt thereof. For example, the reduction in mean serum bile acid concentration is about 110 μmol/L to about 120 μmol/L following 24 weeks of administration of odevixibat, or a pharmaceutically acceptable salt thereof. In some embodiments, the reduction in mean serum bile acid concentration is about 115 following 24 weeks of administration of odevixibat, or a pharmaceutically acceptable salt thereof.

In some embodiments, the reduction in mean serum bile acid concentration is about 150 μmol/L to about 180 μmol/L following 48 weeks of administration of odevixibat, or a pharmaceutically acceptable salt thereof. For example, the reduction in mean serum bile acid concentration is about 155 μmol/L to about 170 μmol/L following 48 weeks of administration of odevixibat, or a pharmaceutically acceptable salt thereof. In some embodiments, the reduction in mean serum bile acid concentration is about 165 (e.g., about 166) following 48 weeks of administration of odevixibat, or a pharmaceutically acceptable salt thereof.

In some embodiments, following administration of odevixibat, or a pharmaceutically acceptable salt thereof, for at least 24 weeks, the subject exhibits a serum bile acid concentration of less than 70 μmol/L (e.g., less than 60 μmol/L; less than 50 μmol/L, etc.).

In some embodiments, following administration of odevixibat, or a pharmaceutically acceptable salt thereof, for at least 24 weeks, the subject exhibits a reduction in serum bile acid concentration of at least 50% relative to baseline (e.g., at least 55%; at least 60; at least 65%; at least 70%; at least 75%; at least 80%; at least 85%; at least 90%; at least 95%). In some embodiments, the subject exhibits a reduction in serum bile acid concentration of at least 60%, at least 70%, or at least 80% relative to baseline.

In some embodiments, the serum bile acid concentration is normalized following administration of odevixibat, or a pharmaceutically acceptable salt thereof. In some embodiments, the serum bile acid concentration is normalized following 48 weeks of administration of odevixibat, or a pharmaceutically acceptable salt thereof.

In some embodiments, wherein the subject has PFIC2 and is a subject in need thereof, following administration of odevixibat, or a pharmaceutically acceptable salt thereof, for at least 48 weeks, the subject exhibits a serum bile acid concentration below the threshold for PFIC2 disease modification. See, e.g., van Wessel D B E, et al. *J Hepatol.* 2020; 73:84-93.

In some embodiments, following administration of odevixibat or a pharmaceutically acceptable salt thereof, growth is improved relative to placebo. In some embodiments, following administration of odevixibat, or a pharmaceutically acceptable salt thereof, the subject exhibits an increase in mean height Z score relative to baseline.

In some embodiments, the increase in mean height Z score is at least 0.1, at least 0.2, at least 0.5, at least 0.75, at least 1, at least 1.25, or at least 1.5 relative to baseline. For example, the mean height Z score increased about 0.5 to about 2.0 (e.g., about 0.5 to about 0.8; about 0.5 to about 1.2; about 0.5 to about 1.5; about 0.7 to about 1.5; about 0.8 to about 1.4; about 0.9 to about 1.3; and about 1.0 to about 1.2). In some embodiments, the mean height Z score increased about 1.1.

In some embodiments, the increase in mean height Z score occurs following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the increase in mean height Z score occurs following administration of odevixibat, or a pharmaceutically acceptable salt thereof, for at least 4 weeks, at least 8 weeks, at least 12 weeks, at least 16 weeks, at least 20 weeks, or at least 24 weeks. In some embodiments, the increase in mean height Z score occurs following 12 weeks of administration. In some embodiments, the increase in mean height Z score occurs following 24 weeks of administration. In some embodiments, the increase in mean height Z score occurs following 48 weeks of administration. In some embodiments, the increase in mean height Z score occurs following 72 weeks of administration.

In some embodiments, the mean height Z score increases about 0.9 to about 1.3 following administration of odevixibat, or a pharmaceutically acceptable salt thereof, for 48 weeks. In some embodiments, the mean height Z score increases about 1.0 to about 1.2 following administration of odevixibat, or a pharmaceutically acceptable salt thereof, for 48 weeks. In some embodiments, the mean height Z score increases about 1.1 following administration of odevixibat, or a pharmaceutically acceptable salt thereof, for 48 weeks.

In some embodiments, following administration of odevixibat, or a pharmaceutically acceptable salt thereof, the subject exhibits an increase in mean weight Z score.

In some embodiments, the increase in mean weight Z score is at least 0.2, at least 0.4, at least 0.6, at least 0.8, at least 1, at least 1.2, or at least 1.4. For example, the mean weight Z score increased about 0.2 to about 1.5 (e.g., about 0.5 to about 0.8; about 0.5 to about 1.2; about 0.5 to about 1.5; about 0.7 to about 1.5; about 0.8 to about 1.4; about 0.9 to about 1.3; and about 1.0 to about 1.2). In some embodiments, the mean weight Z score increased about 1.1.

In some embodiments, the increase in mean weight Z score occurs following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the increase in mean weight Z score occurs following administration of odevixibat, or a pharmaceutically acceptable salt thereof, for at least 4 weeks, at least 8 weeks, at least 12 weeks, at least 16 weeks, at least 20 weeks, or at least 24 weeks. In some embodiments, the increase in mean weight Z score occurs following 12 weeks of administration. In some embodiments, the increase in mean weight Z score occurs following 24 weeks of administration. In some embodiments, the increase in mean weight Z score occurs following 48 weeks of administration. In some embodiments, the increase in mean weight Z score occurs following 72 weeks of administration.

In some embodiments, the mean weight Z score increases about 0.9 to about 1.3 following administration of odevixibat, or a pharmaceutically acceptable salt thereof, for 48 weeks. In some embodiments, the mean weight Z score increases about 1.0 to about 1.2 following administration of odevixibat, or a pharmaceutically acceptable salt thereof, for 48 weeks. In some embodiments, the mean weight Z score increases about 1.1 following administration of odevixibat, or a pharmaceutically acceptable salt thereof, for 48 weeks.

In some embodiments, the mean weight Z score normalizes following administration of odevixibat, or a pharmaceutically acceptable salt thereof, for 48 weeks.

In some embodiments, the subject exhibits improvement in sleep parameters following administration of odevixibat, or a pharmaceutically acceptable salt thereof. Improvements in sleep parameters can include, for example, mean decreases in caregiver-reported percentage of days with scratching associated with bleeding, needing help falling asleep, needing soothing, or sleeping with caregiver. As described in the Examples, at week 48, clinicians and caregivers reported that ≥88% of patients responding to odevixibat (sBA response, sBAs <65 or <102 μmol/L for patients with PFIC1 and PFIC2, respectively; or a pruritus response, a ≥1-point drop from baseline in pruritus score) had moderately or very much better sleep since starting odevixibat.

In some embodiments, the mean decrease in caregiver-reported percentage of days with scratching associated with bleeding is about 14% to about 45% (e.g., mean decrease of about 15%, about 20%, about 25%, about 30% about 35%, or about 45%) following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. In some embodiments, the mean decrease in caregiver-reported percentage of days with scratching associated with bleeding is about 14% to about 45% following administration of odevixibat, or a pharmaceutically acceptable salt thereof, for 48 weeks.

In some embodiments, the mean decrease in caregiver-reported percentage of days needing help falling asleep is about 20% to about 75% (e.g., mean decrease of about 22%, about 25%, about 30% about 35%, about 45%, about 50%, about 55%, about 60%, about 65%, about 70%, or about 75%) following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. In some embodiments, the mean decrease in caregiver-reported percentage of days needing help falling asleep is about 20% to about 75% following administration of odevixibat, or a pharmaceutically acceptable salt thereof, for 48 weeks.

In some embodiments, the mean decrease in caregiver-reported percentage of days needing soothing is about 20% to about 75% (e.g., mean decrease of about 22%, about 25%, about 30% about 35%, about 45%, about 50%, about 55%, about 60%, about 65%, about 70%, or about 75%) following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. In some embodiments, the mean decrease in caregiver-reported percentage of days needing soothing is about 20% to about 75% following administration of odevixibat, or a pharmaceutically acceptable salt thereof, for 48 weeks.

In some embodiments, the mean decrease in caregiver-reported percentage of days needing to sleep with caregiver is about 20% to about 75% (e.g., mean decrease of about 22%, about 25%, about 30% about 35%, about 45%, about 50%, about 55%, about 60%, about 65%, about 70%, or about 75%) following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. In some embodiments, the mean decrease in caregiver-reported percentage of days needing to sleep with the caregiver is about 20% to about 75% following administration of odevixibat, or a pharmaceutically acceptable salt thereof, for 48 weeks.

In some embodiments, the subject exhibits improvement in liver parameters following administration of odevixibat, or a pharmaceutically acceptable salt thereof. For example, in some embodiments, levels of autotaxin, which is linked to cholestatic pruritus intensity, and/or plasma 7α-hydroxy-4-cholesten-3-one (p-C4), a marker of bile acid synthesis, are improved following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc.

In some embodiments, autotaxin levels are decreased following administration of odevixibat, or a pharmaceutically acceptable salt thereof. In some embodiments, autotaxin levels can be decreased 500 to 1000 ng/mL, 750 to 1500 ng/mL, 1000 to 2000 ng/mL, or 1500 to 2500 ng/mL from baseline following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, autoxtaxin levels can be reduced approximately 50% following administration of odevixibat, or a pharmaceutically acceptable salt thereof, for at least 24 weeks.

In some embodiments, plasma C4 levels are increased following administration of odevixibat, or a pharmaceutically acceptable salt thereof. For example, plasma C4 levels (ng/mL) can be increased 7.5 to 15 ng/mL, 10 to 20 ng/mL, 15 to 25 ng/mL, 20 to 30 ng/mL, or 25 to 35 ng/mL from baseline following administration of odevixibat, or a pharmaceutically acceptable salt thereof, for at least 4 weeks, at least 24 weeks, or at least 48 weeks.

In some embodiments, serum alanine aminotransferase (ALT) levels are improved following administration of odevixibat, or a pharmaceutically acceptable salt thereof.

In some embodiments, the PFIC is PFIC 1. In some embodiments, the PFIC is PFIC 2. In some embodiments, the PFIC is PFIC 3.

In some embodiments, the subject is a pediatric subject.

In some embodiments, the subject is administered 120 μg/kg/day of odevixibat, or a pharmaceutically acceptable salt thereof. In some embodiments, the subject is administered 40 μg/kg/day of odevixibat, or a pharmaceutically acceptable salt thereof.

In some embodiments, the subject was odevixibat naïve prior to the first administration of the pharmaceutical formulation comprising odevixibat, or a pharmaceutically acceptable salt thereof.

IBAT Inhibitors

Provided herein are methods for treating PFIC with an ileal bile acid transport (IBAT) inhibitor (also referred to as an apical sodium-dependent bile acid transport inhibitor ASBTI). In some embodiments, the IBAT inhibitor is

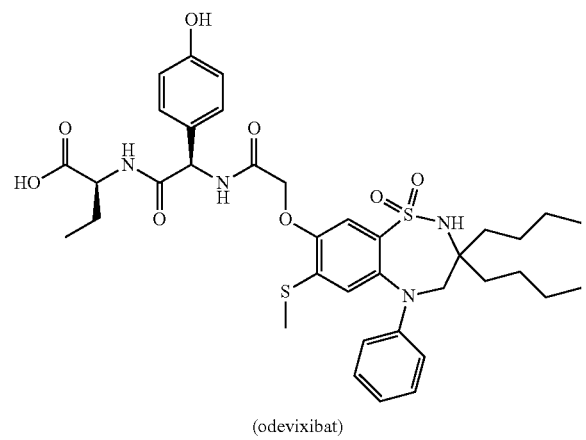

(odevixibat)

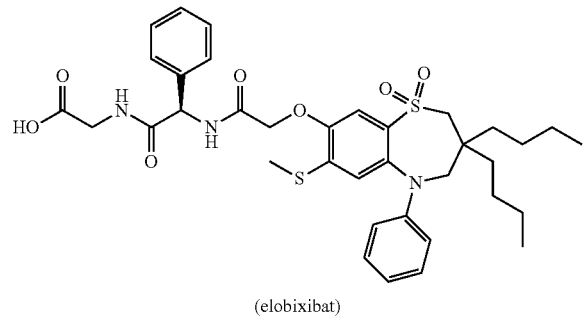

(elobixibat)

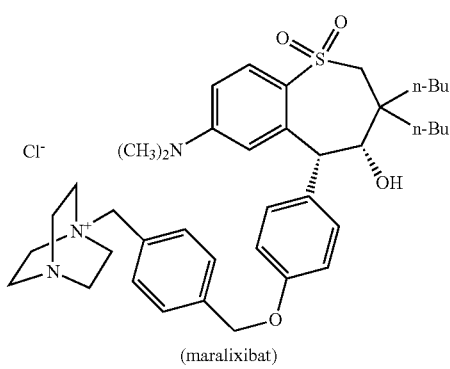

(maralixibat)

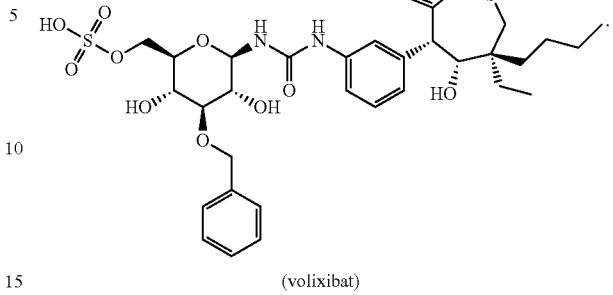

(volixibat)

or a pharmaceutically acceptable salt thereof. An IBAT inhibitor as provided herein includes solvates and hydrates thereof. For example, odevixibat can be present as a hydrate (e.g., a sesquihydrate). In some embodiments, the IBAT inhibitor is odevixibat, or a pharmaceutically acceptable salt thereof. In some embodiments, the IBAT inhibitor is maralixibat, or a pharmaceutically acceptable salt thereof. In some embodiments, the IBAT inhibitor is volixibat, or a pharmaceutically acceptable salt thereof. In some embodiments, the IBAT inhibitor is elobixibat, or a pharmaceutically acceptable salt thereof. In some embodiments, the IBAT inhibitor comprises a combination of two or more of odevixibat, maralixibat, volixibat, and elobixibat, or a pharmaceutically acceptable salt thereof.

IBAT inhibitors can be prepared using described methods, for example, U.S. Pat. Nos. 5,994,391; 6,020,330; 6,906,058; 7,192,945; 7,132,416; 7,238,684; and International Publication No. WO 96/05188. The IBAT inhibitor can be present in amorphous or crystalline form. See, for example, U.S. Pat. Nos. 9,409,875; 10,183,920; and International Publication No. WO 2019/245448.

Provided herein are methods for treating progressive familial intrahepatic cholestasis (PFIC) in a subject in need thereof, the method comprising administering (e.g., orally) to the subject a therapeutically effective amount of a pharmaceutical formulation comprising an IBAT inhibitor, or a pharmaceutically acceptable salt thereof. Also provided herein are methods for treating pruritus associated with progressive familial intrahepatic cholestasis (PFIC) in a subject in need thereof, the method comprising administering (e.g., orally) to the subject a therapeutically effective amount of a pharmaceutical formulation comprising an IBAT inhibitor, or a pharmaceutically acceptable salt thereof.

In some embodiments, following administration of the IBAT inhibitor, the subject exhibits a reduction in mean monthly pruritus score.

In some embodiments, the reduction in mean monthly pruritus score is at least 0.5, at least 0.6, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, or at least 2.0. For example, the reduction in mean monthly pruritus score is about 0.5 to about 2.0 (e.g., about 0.5 to about 1.5; about 0.5 to about 1.2; about 0.8 to about 1.4; about 0.9 to about 1.2; about 1.2 to about 2.0; about 1.2 to about 1.5; about 1.2 to about 1.8; about 1.4 to about 2.0; about 1.6 to about 2.0; about 1.5 to about 2.0; about 1.3 to about 1.6; and about 1.4 to about 1.8).

In some embodiments, the reduction in mean monthly pruritus score occurs following administration of the IBAT inhibitor for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the reduction in mean monthly pruritus score occurs following administration of the IBAT inhibitor for at least 4 weeks, at least 8 weeks, at least 12 weeks, at least 16 weeks, at least 20 weeks, or at least 24 weeks. In some embodiments, the reduction in mean monthly pruritus score occurs following 4 weeks of administration. In some embodiments, the reduction in mean monthly pruritus score occurs following 24 weeks of administration. In some embodiments, the reduction in mean monthly pruritus score occurs following 48 weeks of administration. In some embodiments, the reduction in mean monthly pruritus score occurs following 72 weeks of administration.

In some embodiments, the reduction in mean monthly pruritus score is about 0.5 to about 1.5 following 24 weeks of administration of the IBAT inhibitor. In some embodiments, the reduction in mean monthly pruritus score is about 1.2 to about 2.0 following 48 weeks of administration of the IBAT inhibitor.

In some embodiments, the subject exhibits a reduction in mean serum bile acid concentration.

In some embodiments, the reduction in mean serum bile acid concentration is at least 50 µmol/L, at least 75 µmol/L, at least 100 µmol/L, at least 125 µmol/L, at least 150 µmol/L, or at least 175 µmol/L relative to baseline. For example, the reduction in mean serum bile acid concentration is about 50 µmol/L to about 180 µmol/L relative to baseline (e.g., about 50 µmol/L to about 100 µmol/L; about 50 µmol/L to about 120 µmol/L; about 50 µmol/L to about 150 µmol/L; about 65 µmol/L to about 120 µmol/L; about 50 µmol/L to about 90 µmol/L; about 65 µmol/L to about 85 µmol/L; about 100 µmol/L to about 130 µmol/L; about 100 µmol/L to about 180 µmol/L; and about 150 µmol/L to about 180 µmol/L).

In some embodiments, the reduction in mean serum bile acid concentration occurs following administration of the IBAT inhibitor for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the reduction in mean serum bile acid concentration occurs following administration of the IBAT inhibitor for at least 4 weeks, at least 8 weeks, at least 12 weeks, at least 16 weeks, at least 20 weeks, or at least 24 weeks. In some embodiments, the reduction in mean serum bile acid concentration occurs following 4 weeks of administration. In some embodiments, the reduction in mean serum bile acid concentration occurs following 12 weeks of administration. In some embodiments, the reduction in mean serum bile acid concentration occurs following 24 weeks of administration. In some embodiments, the reduction in mean serum bile acid concentration occurs following 48 weeks of administration. In some embodiments, the reduction in mean serum bile acid concentration occurs following 72 weeks of administration.

In some embodiments, the reduction in mean serum bile acid concentration is about 50 µmol/L to about 90 µmol/L following 12 weeks of administration of the IBAT inhibitor. In some embodiments, the reduction in mean serum bile acid concentration is about 100 µmol/L to about 130 µmol/L following 24 weeks of administration of the IBAT inhibitor. In some embodiments, the reduction in mean serum bile acid concentration is about 150 µmol/L to about 180 µmol/L following 48 weeks of administration of the IBAT inhibitor.

In some embodiments, following administration of the IBAT inhibitor for at least 24 weeks, the subject exhibits a serum bile acid concentration of less than 70 µmol/L (e.g., less than 60 µmol/L; less than 50 µmol/L, etc.).

In some embodiments, following administration of the IBAT inhibitor for at least 24 weeks, the subject exhibits a reduction in serum bile acid concentration of at least 50% relative to baseline (e.g., at least 55%; at least 60; at least 65%; at least 70%; at least 75%; at least 80%; at least 85%; at least 90%; at least 95%). In some embodiments, the subject exhibits a reduction in serum bile acid concentration of at least 60%, at least 70%, or at least 80% relative to baseline.

In some embodiments, wherein the subject has progressive familial intrahepatic cholestasis 2 (PFIC2) is a subject in need thereof, following administration of the IBAT inhibitor for at least 48 weeks, the subject exhibits a serum bile acid concentration below the threshold for PFIC2 disease modification. See, e.g., van Wessel D B E, et al. *J Hepatol.* 2020; 73:84-93.

In some embodiments, following administration of the IBAT inhibitor, the subject exhibits an increase in mean height Z score relative to baseline.

In some embodiments, the increase in mean height Z score is at least 0.1, at least 0.2, at least 0.5, at least 0.75, at least 1, at least 1.25, or at least 1.5 relative to baseline. For example, the mean height Z score increased about 0.5 to about 2.0 (e.g., about 0.5 to about 0.8; about 0.5 to about 1.2; about 0.5 to about 1.5; about 0.7 to about 1.5; about 0.8 to about 1.4; about 0.9 to about 1.3; and about 1.0 to about 1.2).

In some embodiments, the increase in mean height Z score occurs following administration of the IBAT inhibitor for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the increase in mean height Z score occurs following administration of the IBAT inhibitor for at least 4 weeks, at least 8 weeks, at least 12 weeks, at least 16 weeks, at least 20 weeks, or at least 24 weeks. In some embodiments, the increase in mean height Z score occurs following 4 weeks of administration. In some embodiments, the increase in mean height Z score occurs following 12 weeks of administration. In some embodiments, the increase in mean height Z score occurs following 24 weeks of administration. In some embodiments, the increase in mean height Z score occurs following 48 weeks of administration. In some embodiments, the increase in mean height Z score occurs following 72 weeks of administration.

In some embodiments, the mean height Z score increases about 0.9 to about 1.3 following administration of the IBAT inhibitor for 48 weeks.

In some embodiments, following administration of the IBAT inhibitor, the subject exhibits an increase in mean weight Z score.

In some embodiments, the increase in mean weight Z score is at least 0.2, at least 0.4, at least 0.6, at least 0.8, at least 1, at least 1.2, or at least 1.4. For example, the mean weight Z score increased about 0.2 to about 1.5 (e.g., about 0.5 to about 0.8; about 0.5 to about 1.2; about 0.5 to about 1.5; about 0.7 to about 1.5; about 0.8 to about 1.4; about 0.9 to about 1.3; and about 1.0 to about 1.2).

In some embodiments, the increase in mean weight Z score occurs following administration of the IBAT inhibitor for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. For example, the increase in mean weight Z score occurs following administration of the IBAT inhibitor for at least 4 weeks, at least 8 weeks, at least 12 weeks, at least 16 weeks, at least 20 weeks, or at least 24 weeks. In some embodiments, the increase in mean weight Z score occurs following 4 weeks of administration. In some embodiments, the increase in mean weight Z score occurs following 12 weeks of administration. In some embodiments, the increase in mean weight Z score occurs following 24 weeks of administration. In some embodiments, the increase in mean weight Z score occurs following 48 weeks of administration. In some embodiments, the increase in mean weight Z score occurs following 72 weeks of administration.

In some embodiments, the mean weight Z score increases about 0.9 to about 1.3 following administration of the IBAT inhibitor for 48 weeks. In some embodiments, the mean weight Z score increases about 1.0 to about 1.2 following administration of the IBAT inhibitor for 48 weeks. In some embodiments, the mean weight Z score increases about 1.1 following administration of the pharmaceutical formulation for 48 weeks.

In some embodiments, the mean weight Z score normalizes following administration of the IBAT inhibitor for 48 weeks.

In some embodiments, the subject exhibits improvement in sleep parameters following administration of the IBAT inhibitor. Improvements in sleep parameters can include, for example, mean decreases in caregiver-reported percentage of days with scratching associated with bleeding, needing help falling asleep, needing soothing, or sleeping with caregiver. As described in the Examples, at week 48, clinicians and caregivers reported that ≥88% of patients responding to odevixibat (sBA response, sBAs <65 or <102 µmol/L for patients with PFIC1 and PFIC2, respectively; or a pruritus response, a ≥1-point drop from baseline in pruritus score) had moderately or very much better sleep since starting odevixibat.

In some embodiments, the subject exhibits improvement in liver parameters following administration of the IBAT inhibitor. For example, in some embodiments, levels of autotaxin, which is linked to cholestatic pruritus intensity and/or plasma 7α-hydroxy-4-cholesten-3-one (p-C4), a marker of bile acid synthesis, are improved following administration of odevixibat, or a pharmaceutically acceptable salt thereof, for at least 4 weeks, at least 8 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks, etc. In some embodiments, serum ALT levels are improved following administration of odevixibat, or a pharmaceutically acceptable salt thereof.

In some embodiments, the PFIC is PFIC 1. In some embodiments, the PFIC is PFIC 2. In some embodiments, the PFIC is PFIC 3.

In some embodiments, the subject is a pediatric subject.

In some embodiments, the subject was IBAT inhibitor naïve prior to the first administration of the pharmaceutical formulation comprising the IBAT inhibitor.

Formulations

IBAT inhibitors as provided herein can be formulated as previously described. See, for example, International Publication Nos. WO 2019/245449; WO 2020/0167981; WO 2020/0167985; WO 2020/0167964; U.S. Pat. No. 10,709,755; and U.S. Application No. US 2017/0143738.

Odevixibat, for example, exhibits high potency and should be administered in low doses, such as ranging from about 40 to about 120 µg/kg. This corresponds to doses as low as 200 to 800 µg in the treatment of paediatric patients that weigh about 5 to 20 kg (e.g., infants and toddlers). It is desirable that a formulation of odevixibat can be administered to young patients in a dosage form having a small size. It is further desirable that such a formulation has good palatability, is not perceived as gritty, and is well-tolerated by infants and small children.

Multiparticulates can be administered to infants from birth if they are administered with a liquid. For children aged approximately 6 months and older (i.e. after weaning), the multiparticulates can be administered in their solid form either directly into the mouth or mixed with semi-solid food. Particle size, shape, texture, hardness, taste and dose volume (i.e., the number of particles) have been reported to be important for acceptability of multiparticulates by infants and children (Kozarewicz, *Int. J. Pharm.* 2014, vol. 469, pp 245-248). Various literature reviews have been conducted on the acceptability of different oral dosage forms in paediatric and older adult patients (see e.g. Liu, et al., *Drugs* 2014, vol. 74, pp. 1871-1889; Drumond et al., *Int. J. Pharm.* 2017, vol. 521, pp. 294-305; Mistry et al., *J. Pharm. Pharmacol.* 2017, vol. 69, pp. 361-376; Walsh et al., *Int. J. Pharm.* 2017, vol. 536, pp. 547-562), but the size and/or dose volume (amount) of multiparticulates investigated have not always been reported in these reviews.

Perception of grittiness may be influenced by a range of factors including particle size, quantity and dosing vehicle (see Mishra et al., *Yakugaku Zasshi* 2009, vol. 129, pp. 1537-1544; Lopez et al., *Eur. J. Pharm. Sci.* 2016, vol. 92, pp. 156-162) as well as the hardness and shape of the particles (Tyle, *Acta Psychologica* 1993, vol. 84, pp. 111-118), with irregular particles being perceived as larger than round (spherical) particles of the same size (Engelen et al., *J. Text. Studies* 2005, vol. 36, pp. 373-386). Grittiness perception studies have shown that grittiness scores may increase with increasing size and dose of the multiparticulates, whereas grittiness scores may decrease with increasing vehicle viscosity (Lopez et al., *Eur. J. Pharm. Sci.* 2016, vol. 92, pp. 156-162).

Capsules can be acceptable for children from approximately 6 years of age. The swallowability of the capsules can depend upon the dosage form dimensions (i.e. the size) and the ability of the child. The size, shape, taste and after taste are important capsule attributes that can influence patient acceptability (Kozarewicz, *Int. J. Pharm.* 2014, vol. 469, pp 245-248). In some embodiments, the size of the capsules is kept as small as possible, and the number of capsules required per dose is kept to a minimum, e.g. not more than 1-3 capsules.

Provided herein is a multiparticulate formulation containing low doses of odevixibat. In some embodiments, the formulation is a paediatric formulation. In some embodiments, the formulation enables weight-based dosing and can be sprinkled onto food. The formulation can be designed to have a good palatability, with an optimal balance between particle size and dose volume.

Provided herein is a pharmaceutical formulation of odevixibat, comprising a plurality of particles, wherein each particle contains odevixibat, or a pharmaceutically acceptable salt thereof, in an amount of from about 0.1% w/w to about 5.0% w/w based on the total weight of the particle.

Because of the low doses in which odevixibat is to be administered, and further because of the multiparticulate form of the application, each particle of the formulation contains only a very low amount of the active ingredient. For example, the amount of odevixibat, or a pharmaceutically acceptable salt thereof, in each particle can be from about 0.2% w/w to about 3.5% w/w, for example, from about 0.3% w/w to about 3.0% w/w, from about 0.4% w/w to about 2.5% w/w, or from about 0.5% w/w to about 2.0% w/w based on the total weight of the particle. In some embodiments, each particle contains odevixibat, or a pharmaceutically acceptable salt thereof, in an amount of about 0.5% w/w based on the total weight of the particle. In another embodiment, each particle contains odevixibat, or a pharmaceutically acceptable salt thereof, in an amount of about 1.0% w/w based on the total weight of the particle. In yet another embodiment, each particle contains odevixibat, or a pharmaceutically acceptable salt thereof, in an amount of about 1.5% w/w based on the total weight of the particle.

As used herein, the term "particles" refers to small particles ranging in size from about 0.1 to about 1.5 mm. Such particles are essentially spherical, although elongated or oblong particles also might be used. The particles may e.g. be pellets, beads, microparticles, microspheres, granules or minitablets, and may optionally be coated with one or more coating layers surrounding every such pellet, bead, microparticle, microsphere, granule or minitablet.

In some embodiments, the particles of the formulation are small enough, that they can be sprinkled onto food and easily swallowed. In some embodiments, the particles can be swallowed without causing a perception of grittiness. In some embodiments, the particles do not give the patient an urge to chew the particles. The particles are, therefore, between about 0.1 and about 1.5 mm in size, for example, between about 0.1 and about 1.0 mm, or between about 0.1 and 0.8 mm, such as about 0.2 mm, about 0.3 mm, about 0.4 mm, about 0.5 mm, about 0.6 mm, or about 0.7 mm. In some embodiments, the particles are between about 0.4 and about 0.8 mm, such as about 0.5 mm, or such as about 0.6 mm, or such as about 0.7 mm. In some embodiments, the particles are about 0.7 mm.

In some embodiments, provided herein is a formulation of odevixibat, wherein each particle comprises a core and a coating layer surrounding the core. The core of each particle may be a pellet, a granule, a minitablet, a bead, a microparticle or a microsphere.

In some embodiments, the core of each particle comprises the active pharmaceutical ingredient (odevixibat), while the coating layer of each particle does not comprise the active pharmaceutical ingredient. In some embodiments, the core of each particle comprises from about 0.1% to about 5% w/w of the active pharmaceutical ingredient, based on the total weight of the particle, such as from about 0.1% to about 2% w/w, such as from about 0.1% to about 1% w/w, or such as from about 0.1% to about 0.5% w/w of the active pharmaceutical ingredient, based on the total weight of the particle.

In some embodiments, the coating layer of each particle comprises the active pharmaceutical ingredient (odevixibat), while the core of each particle does not comprise the active pharmaceutical ingredient. In some embodiments, the coating layer of each particle comprises from about 0.1% to about 5% w/w of the active pharmaceutical ingredient, based on the total weight of the particle, such as from about 0.1% to about 2% w/w, such as from about 0.1% to about 1% w/w, or such as from about 0.1% to about 0.5% w/w of the active pharmaceutical ingredient, based on the total weight of the particle.

The cores may be orally dispersible and comprise soluble ingredients such as a sugar (e.g., sucrose) or a soluble polymer (e.g. hydroxypropyl methylcellulose) or may be non-orally dispersible and comprise non-soluble ingredients such as a non-soluble polymer (e.g., microcrystalline cellulose). In some embodiments, the cores comprise microcrystalline cellulose. In some embodiments, the cores are microcrystalline cellulose spheres.

The coating layer can further comprise a film-forming polymer, such as a cellulose-based polymer, a polysaccharide-based polymer, an N-vinylpyrrolidone-based polymer, an acrylate, an acrylamide, or copolymers thereof. Examples of suitable film-forming polymers include polyvinyl alcohol (PVA), polyvinyl acetate phthalate (PVAP), polyethylene glycol (PEG), polyvinylpyrrolidone (PVP), methacrylic acid copolymers, starch, hydroxypropyl starch, chitosan, shellac, methyl cellulose, hydroxypropyl cellulose (HPC), low-substituted hydroxypropyl cellulose, hydroxypropyl methylcellulose (HPMC; or hypromellose), hydroxypropyl methylcellulose acetate succinate (HPMCAS), hydroxypropyl methylcellulose phthalate (HPMCP), cellulose acetate phthalate (CAP), cellulose acetate trimellitate (CAT), as well as combinations thereof, such as a mixture of methyl cellulose and hydroxypropyl methylcellulose (metolose). In some embodiments, the coating layer comprises a film-forming polymer selected from the group consisting of hydroxypropyl methylcellulose, polyvinyl alcohol (PVA), polyethylene glycol (PEG), starch, hydroxypropyl starch and hydroxypropyl cellulose (HPC). For example, the coating layer can comprise hydroxypropyl methylcellulose as the film-forming polymer.

The coating layer may optionally comprise one or more additional ingredients, such as a plasticizer (e.g. polyethylene glycol, triacetin or triethyl citrate), an anti-tack agent (e.g. talc or magnesium stearate) or a colouring agent (e.g. titanium dioxide, iron oxides, riboflavin or turmeric).

In some embodiments, the formulation comprises odevixibat in crystalline form. In some embodiments, the formulation comprises a crystalline hydrate of odevixibat. In some embodiments, the formulation comprises crystal modification 1 of odevixibat. This stable crystal modification can be obtained from a slurry of odevixibat in a mixture of water and an organic solvent such as ethanol. Under these conditions, a mixed solvate containing about two moles of water and about one to about three, such as about two to about three, moles of ethanol per mole of odevixibat (e.g., a dihydrate-diethanolate or a dihydrate-triethanolate) is initially formed. This mixed solvate is referred to herein as crystal modification 2. When crystal modification 2 is dried, such as under vacuum (e.g., less than 5 mbar) or under a nitrogen flow, it loses its organic solvent molecules and becomes crystal modification 1. In some embodiments, the transformation of crystal modification 2 to crystal modification 1 proceeds via a crystalline intermediate. It is believed that this crystalline intermediate is a dehydrated form, which quickly takes up water from the air. While not wishing to be bound by theory, it is believed that the solvent molecules can be removed without dissolution and recrystallization of the crystals.

Crystal modification 1 of odevixibat cannot only be obtained from a mixture of water and ethanol, as described above, but also from a slurry of odevixibat in a mixture of water and an organic solvent selected from the group consisting of methanol, 2-propanol, acetone, acetonitrile, 1,4-dioxane, DMF and DMSO. Upon drying of the different mixed solvates obtained under these conditions (crystal modification 2), the same crystalline hydrate of odevixibat is obtained, namely crystal modification 1.

Crystal modification 1 contains void volumes that are capable of containing up to about 2 moles of water associated with the crystal per mole of odevixibat, depending on the relative humidity. This form is therefore formally a channel hydrate. At about 30% relative humidity, however, crystal modification 1 contains a substantially stoichiometric amount of about 1.5 moles of water per mole of organic compound and is thus a sesquihydrate. The substantially stoichiometric amount of water is considered advantageous, as the water content of the crystals remains substantially constant even with humidity changes within the normal relative humidity range of about 30% to about 70% RH. Indeed, at normal humidities, such as between about 30 and about 70% RH, crystal modification 1 exhibits relatively low hygroscopicity.

In one embodiment, the formulation comprises crystal modification 1 of odevixibat having an X-ray powder diffraction (XRPD) pattern, obtained with CuKα1-radiation, with at least specific peaks at °2θ positions 5.6±0.2, 6.7±0.2 and/or 12.1±0.2.

In a specific embodiment, the formulation comprises crystal modification 1 having an XRPD pattern, obtained with CuKα1-radiation, with specific peaks at °2θ positions 5.6±0.2, 6.7±0.2 and 12.1±0.2 and one or more of the characteristic peaks: 4.1±0.2, 4.6±0.2, 9.3±0.2, 9.4±0.2 and 10.7±0.2.

In a more specific embodiment, the formulation comprises crystal modification 1 having an XRPD pattern, obtained with CuKα1-radiation, with specific peaks at °2θ positions 4.6±0.2, 5.6±0.2, 6.7±0.2, 9.3±0.2, 9.4±0.2 and 12.1±0.2.

In a more specific embodiment, the formulation comprises crystal modification 1 having an XRPD pattern, obtained with CuKα1-radiation, with characteristic peaks at °2θ positions 4.1±0.2, 4.6±0.2, 5.6±0.2, 6.7±0.2, 9.3±0.2, 9.4±0.2, 10.7±0.2 and 12.1±0.2, and one or more of 8.1±0.2, 8.6±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In an even more specific embodiment, the formulation comprises crystal modification 1 having an XRPD pattern, obtained with CuKα1-radiation, with characteristic peaks at °2θ positions 4.1±0.2, 4.6±0.2, 5.6±0.2, 6.7±0.2, 8.1±0.2, 8.6±0.2, 9.3±0.2, 9.4±0.2, 10.7±0.2, 12.1±0.2, 13.4±0.2, 13.8±0.2, 13.9±0.2, 16.6±0.2, 17.3±0.2, 17.7±0.2, 18.3±0.2, 18.9±0.2, 19.4±0.2, 19.7±0.2, 20.5±0.2, 20.8±0.2, 21.6±0.2, 23.2±0.2, 24.3±0.2, 29.8±0.2 and 30.6±0.2.

In another embodiment, the formulation comprises crystal modification 1 having an XRPD pattern, obtained with CuKα1-radiation, substantially as shown in FIG. 1.

Whereas crystal modification 1 is a sesquihydrate containing about 3.5% (w/w) water at about 30% relative humidity (based on the total crystal weight), it has been observed that the crystal can take up an additional 1.5% (w/w) water when the humidity is increased up to 95% RH. The sorption and desorption of this additional water is fully reversible. The additional water may be adsorbed on the surface or may further fill the channels of the structure. In some embodiments, the term "overhydrated" refers to crystal modification 1 containing from about 1.5 to about 4 moles of water per mole of odevixibat, such as from about 1.5 to about 3.5, or such as from about 1.5 to 3, or such as from about 1.5 to about 2.5, or such as from about 1.5 to about 2 moles of water per mole of odevixibat. In some embodiments, the term "overhydrated" refers to crystal modification 1 containing from about 2 to about 4 moles of water per mole of odevixibat, such as from about 2 to about 3.5, or such as from about 2 to about 3, or such as from about 2 to 2.5 moles of water per mole of odevixibat.

It has been observed that the XRPD pattern of overhydrated crystal modification 1 slightly changes when it is dried, e.g. at 50° C. in vacuum. A small shift of peaks is most clearly seen in the 2θ ranges 5-13° and 18-25°, as shown in FIGS. 3 and 4, respectively. Exposing the dried modification to elevated relative humidity, such as up to 95% RH, makes the XRPD pattern of the overhydrated modification appear again. The peak shifts are a result of the unit cell volume changes, which occur as water molecules go in and out of the crystal structure.

Therefore, in another embodiment, the formulation comprises overhydrated crystal modification 1 having an X-ray powder diffraction (XRPD) pattern, obtained with CuKα1-radiation, with at least specific peaks at °2θ positions 5.7±0.2, 6.7±0.2 and/or 12.0±0.2.

In a specific embodiment, the formulation comprises overhydrated crystal modification 1 having an XRPD pattern, obtained with CuKα1-radiation, with specific peaks at °2θ positions 5.7±0.2, 6.7±0.2 and 12.0±0.2 and one or more of the characteristic peaks: 4.0±0.2, 9.4±0.2, 9.6±0.2 and 10.8±0.2.

In a more specific embodiment, the formulation comprises overhydrated crystal modification 1 having an XRPD pattern, obtained with CuKα1-radiation, with specific peaks at °2θ positions 4.0±0.2, 5.7±0.2, 6.7±0.2, 9.4±0.2, 9.6±0.2, 10.8±0.2 and 12.1±0.2.

In a more specific embodiment, the formulation comprises overhydrated crystal modification 1 having an XRPD pattern, obtained with CuKα1-radiation, with characteristic peaks at °2θ positions 4.0±0.2, 5.7±0.2, 6.7±0.2, 9.4±0.2, 9.6±0.2, 10.8±0.2 and 12.1±0.2, and one or more of 4.7±0.2, 8.0±0.2, 8.6±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

In an even more specific embodiment, the formulation comprises overhydrated crystal modification 1 having an XRPD pattern, obtained with CuKα1-radiation, with characteristic peaks at °2θ positions 4.0±0.2, 4.7±0.2, 5.7±0.2, 6.7±0.2, 8.0±0.2, 8.6±0.2, 9.4±0.2, 9.6±0.2, 10.8±0.2, 12.1±0.2, 13.3±0.2, 14.1±0.2, 15.3±0.2, 16.5±0.2, 17.3±0.2, 19.3±0.2, 19.7±0.2, 19.9±0.2, 20.1±0.2, 20.8±0.2, 21.7±0.2, 23.6±0.2, 26.2±0.2, 26.5±0.2, 28.3±0.2 and 30.9±0.2.

Figure 2:
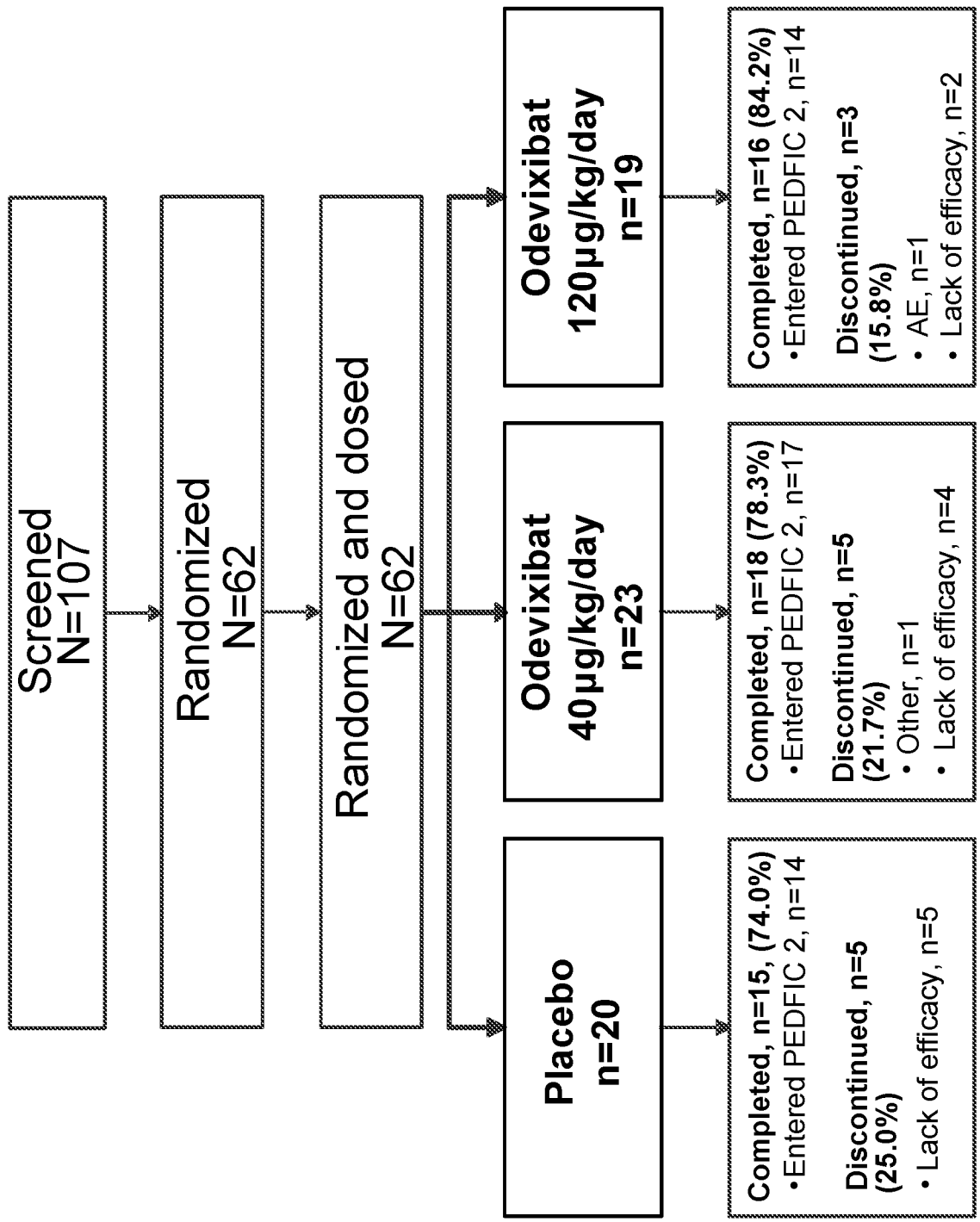
FIG. 2 illustrates the disposition and treatment protocols for patients in PEDFIC 1. "Completed" and "Discontinued" refer to the treatment period. There were 11 patients who rolled over early into the PEDFIC 2 open-label extension study: seven at week 12, one at week 14, and three at week 18.

In another embodiment, the formulation comprises overhydrated crystal modification 1 of odevixibat having an XRPD pattern, obtained with CuKα1-radiation, substantially as shown in FIG. 2.

It is desirable that the use of organic solvents in the preparation of the formulation is avoided. In some embodiments, water is used as the solvent for the preparation of the formulation. Odevixibat dissolves in water only very poorly, and the solubility at pH 7 and at 37° C. has been determined to be as low as about 30 µg/mL. Because of this low solubility in water, aqueous suspensions of odevixibat can contain larger agglomerates of odevixibat, which may lead to an uneven distribution of the active pharmaceutical ingredient on the cores, i.e. the cores may contain different amounts of odevixibat, which in turn impacts dose uniformity. Accordingly, in some embodiments, the aqueous suspension of odevixibat is homogeneous. In some embodiments, a homogeneous aqueous suspension of odevixibat is sprayed onto the cores.

Odevixibat exhibits high potency and it should be administered in low doses, especially in the treatment of pediatric patients that weigh about 5 to 20 kg. In order to reach high dose uniformity for the multiparticulate formulation disclosed herein, it is important that each particle of the formulation substantially contains the same amount of odevixibat, i.e., the deviation in the odevixibat content of the particles of the formulation should be as low as possible.

As used herein, the term "homogeneous" refers to a suspension that does not contain agglomerates of odevixibat that are larger than about 200 μm, for example, no agglomerates larger than about 100 μm, or no agglomerates larger than about 50 μm. The size of the odevixibat agglomerates in the coating suspension may be determined by optical microscopy, using a method based on European Pharmacopoeia 9.0, monograph 2.9.37, and as described in the experimental section. Alternatively, the size of the odevixibat agglomerates in the coating suspension may be determined by light scattering techniques, such as low-angle laser light scattering (LALLS). In some embodiments, the $d_{90}$ value for the particle size distribution of the coating suspension is smaller than 15 μm, such as smaller than 14 μm, such as smaller than 13 μm, such as smaller than 12 μm, such as smaller than 11 μm, or such as smaller than 10 μm.

In some embodiments, a homogeneous suspension of odevixibat can be prepared by dispersing the compound in water by wet-milling. Wet-milling is a process in which a solid substance is dispersed in a liquid by shearing, by crushing, or by attrition. Examples of wet-milling apparatus include colloid mills, conical mills, ball mills, disc mills and high-shear dispersing machines. A specific example of a wet-milling apparatus for use in the formulations provided herein is a colloid mill.

In some embodiments, the crystallinity of odevixibat increases during the wet-milling.

In some embodiments, odevixibat is first wetted in a small amount of water using a homogenizer and thereafter dispersed in water using a colloid mill. Spraying the homogenized dispersion onto the cores enables an even distribution of the active pharmaceutical ingredient.

It is desirable that the formulation is free of any ingredients that are not strictly necessary for the formulation, such as surfactants. In some embodiments, therefore, the coating suspension does not contain surfactants. Similarly, in some embodiments, the coating layer of the formulation does not contain surfactants.

In one embodiment, the particles are contained within a sachet. In another embodiment, the particles are contained within a capsule. Such capsules may be made from gelatine, from a cellulose-based polymer such as a hydroxypropyl methylcellulose (hypromellose), or from a polysaccharide-based polymer such as a pullulan. Capsules may be swallowed intact, or may be designed to be opened, so that, for example, the contents (i.e. the particles) can be sprinkled onto a food vehicle for administration. In the latter case, the number of particles in one capsule should fit onto a single tablespoon of food. In some embodiments, a capsule contains from about 20 to about 100 mg of particles, such as about 30, about 40, about 50, about 60, about 70, about 80 or about 90 mg.

For younger paediatric patients, such as infants, toddlers and children up to about 6 years old, the particles can be sprinkled onto food that can be easily swallowed and which does not require chewing, such as yoghurt, apple sauce, fruit purée or oatmeal. For older paediatric patients, such as children older than about 6 years old, adolescents and younger adults, capsules containing the particles may be swallowed intact, i.e. without opening. For newborn patients up to about 6 months old, who have not yet been weaned or are unable to take semi-solid food, the formulation can be administered by dispersing the particles in a suitable liquid vehicle, such as breast milk, baby formula or water. When the particles have been dispersed in a liquid vehicle, they can be administered to the patient within 30 minutes after dispersion, without loss of the active ingredient or indications of degradation. In some embodiments, the volume of liquid vehicle used for administering the odevixibat particles, including rinsing, can be smaller than about 20 mL, such as smaller than about 15 mL, such as smaller than about 10 mL, or such as smaller than about 5 mL. In some embodiments, the dispersed particles are administered directly into the mouth using an oral syringe.

A number of embodiments of the invention have been described. Nevertheless, it will be understood that various modifications may be made without departing from the spirit and scope of the invention. Accordingly, other embodiments are within the scope of the following claims.

EXAMPLES

Example 1—Efficacy and Safety of Odevixibat, an Ileal Bile Acid Transporter Inhibitor, in Children with Progressive Familial Intrahepatic Cholestasis Types 1 and 2: Results from PEDFIC 1, a Randomized, Double-Blind, Placebo-Controlled Phase 3 Trial PFIC is a group of rare, inherited diseases of hepatocellular origin with a common underlying pathogenesis involving disrupted bile formation. PFIC results from genetic variants in a number of genes, including mutations in ATP8B1 and ABCB11 (designated PFIC types 1 and 2, respectively). Severe pruritus is common in children diagnosed with PFIC, and the need for some form of relief is critical given that pruritus can considerably impact quality of life and result in an indication for liver transplantation. Retention of bile acids within the liver is a central component of the etiopathogenesis of cholestasis in PFIC. Secondary spillover of bile acids into the peripheral circulation is easily measured and forms a clinically useful marker of disease severity.

Current treatment options for patients with PFIC are limited to surgical interruption of bile and the enterohepatic circulation and/or off label symptomatic medical therapies. Because these therapies may not provide adequate relief or prevent progression to end-stage liver disease, patients often require liver transplantation.

The IBAT, also called the apical sodium-dependent bile acid transporter (SLC10A2), is located on the luminal surface of enterocytes in the terminal ileum; this transporter mediates resorption of conjugated bile acids for recirculation back to the liver. 11 Inhibition of IBAT disrupts the enterohepatic circulation and leads to fecal elimination of bile acids similar to surgical interruption of the enterohepatic circulation.

Odevixibat is an orally administered, potent, luminally restricted, selective IBAT inhibitor in development to treat cholestatic liver diseases. In this phase 3, randomized, 24-week trial (PEDFIC 1), the efficacy and safety of odevixibat versus placebo was evaluated in children with PFIC1 or PFIC2. The efficacy of odevixibat in patients with PFIC was evaluated a 24-week, randomized, double-blind, placebo-controlled trial conducted in 62 patients with a confirmed diagnosis of PFIC Type 1 or Type 2 (NCT03566238; European Union (EU), 2017-002338-21; PEDFIC1; FIG. 1). Patients were randomized 1:1:1 to placebo, or 40 or 120 μg/kg odevixibat and stratified by PFIC Type (1 or 2) and age (6 months to 5 years, 6 to 12 years, and 13 to ≤18 years). Patients with pathologic variations of the ABCB11 gene that predict complete absence of the bile salt export pump (BSEP) protein and those with alanine aminotransferase (ALT) >10×ULN or bilirubin >5×ULN were excluded from the study.

Methods

This multicenter study (ClinicalTrials.gov identifier: NCT03566238) was conducted at 33 sites in the United States, Canada, Europe, Australia, and the Middle East. The trial adhered to the Declaration of Helsinki and the International Conference on Harmonization guidelines for Good Clinical Practice. Research protocols and amendments were approved by relevant institutional review boards and ethics committees at each site. Patients or their caregivers provided written informed consent before entering the study.

Study Design and Treatment

The study consisted of a screening phase and parallel-design treatment period (FIG. 1). Two screening visits occurred: the first took place during days −56 to −35 prior to the first dose of study drug and the second occurred during days −28 to −7. On day 0, all eligible patients were randomized 1:1:1 to oral, once-daily placebo, 40 μg/kg/day odevixibat, or 120 μg/kg/day odevixibat. After written informed consent was obtained, an 8-digit patient identification number was assigned by the Interactive Web Response System (IWRS). The first two digits denoted country, followed by a 3-digit site number, and a 3-digit patient sequence number. The randomization codes were computer generated by a biostatistician at ICON Clinical Research Ltd (Dublin, Ireland) and kept by an unblinded statistician at Firma Clinical Research (Chicago, Ill., USA), independent from the project team. Patients deemed eligible for randomization were assigned a unique 4 digit randomization number by the IWRS that identified which treatment was allocated to the patient. Randomization was done in a block size of six and stratified according to PFIC type 1 or 2 and age group (6 months to 5 years, 6 to 12 years, and 13 to ≤18 years) to ensure approximate balance between dose schemes (1:1:1). A separate randomization list was prepared for the patients who had taken part in study A4250-003, regardless of stratification. Randomization codes were assigned sequentially as patients became eligible for randomization. The IWRS system assigned a study drug number(s) corresponding to the randomization arm at each dispensing visit. A 5-digit study drug number identified study drug packs and was detailed on the study drug label.

To ensure blinding of treatment assignment, study drug and matching placebo had the same shape and size, with labels on the study drug containers that did not identify the randomized treatment assignment. Dispensing of study drug was coordinated by IWRS.

Treatment was dispensed during on-site clinic visits, and patients or caregivers were instructed to take or administer the study drug at home each morning, either as an intact capsule(s) (swallowed with a glass of water and with food) or sprinkled on soft, room-temperature food (e.g., applesauce, followed by water). The double-blind PEDFIC 1 treatment period lasted 24 weeks.

Patients who completed the treatment period either attended a follow-up visit 28 days after the last dose of study drug, or they could continue into an optional 72 week open-label extension study (PEDFIC 2; ClinicalTrials.gov identifier: NCT03659916), in which all patients received odevixibat. Initially, patients could withdraw from PEDFIC 1 due to intolerable symptoms after ≥12 weeks of treatment and roll over early into PEDFIC 2; however, this provision was removed with the last PEDFIC 1 protocol amendment. There were up to 10 planned clinic visits, including visits for screening, treatment, and follow-up, with one telephone call at week 2 between the randomization and week 4 visits.

Patients

Key Eligibility Criteria

Children (aged 0.5 to 18 years) with genetic confirmation of biallelic pathogenic mutations in the ATP8B1 (i.e., PFIC1) or ABCB11 genes (i.e., PFIC2), elevated serum bile acids (≥100 μmol/L), history of significant pruritus, and an average caregiver-reported observed scratching score ≥2 (calculated from daily electronic diary [eDiary] entries) in the 14 days prior to randomization, were eligible for inclusion. Additionally, caregivers or age-appropriate patients (≥8 years of age) agreed to use the eDiary device to record symptoms. Patients with two mutations in ABCB11 predicting a complete absence of functional bile salt export pump protein were excluded.

Additional exclusion criteria included the following: medical history or ongoing presence of other types of liver disease (e.g., biliary atresia, benign recurrent intrahepatic cholestasis, liver cancer, histopathologic evidence of non-progressive familial intrahepatic cholestasis [PFIC] etiology of cholestasis); diseases or conditions known to interfere with bile acid metabolism (e.g., inflammatory bowel disease); chronic (>3 months) diarrhea; active, clinically significant, acute or chronic infection or infection requiring hospitalization or parenteral anti-infective treatment within 4 weeks of treatment start; or chronic kidney disease. Patients were excluded from the study if they had biliary diversion surgery within the 6 months prior to the screening period; had a liver transplant or one planned within 6 months of randomization; signs of decompensated liver disease (e.g., ascites); or pruritus caused by any condition other than chronic cholestasis (e.g., treatment-refractory atopic dermatitis, other primary pruritic skin disease). Use of resins or medications that slow gastrointestinal motility were not permitted. Patients with laboratory parameters above the following thresholds were excluded: international normalized ratio (INR) >1.4, serum alanine aminotransferase (ALT) >10 times the upper limit of normal (ULN) at screening, serum ALT >15 times the ULN during the last 6 months, and total bilirubin >10 times the ULN at screening.

Assessments

Two different primary endpoints were evaluated. The first primary endpoint in this study was the proportion of positive pruritus assessments at the patient level over the 24-week treatment period based on an observer-reported outcome (ObsRO) instrument. A positive pruritus assessment was a score of ≤1 or at least 1-point improvement from baseline. Pruritus assessments were conducted in the morning and evening using a 5-point scale (0-4), with higher scores indicating worse scratching and/or sleep disturbance. A change from baseline of 1-point or more improvement in pruritus score was determined to be clinically meaningful through a blinded analysis prior to database lock.

The study was also powered for a second primary endpoint, the proportion of patients with at least a 70% reduction in fasting serum bile acid levels or who achieved a level ≤70 μmol/L (28.6 μg/mL) at the end of treatment (i.e., administration of odevixibat for 24 weeks). Additional secondary endpoints included changes from baseline to end of treatment in growth, sleep parameters (per ObsRO), and ALT. All serum bile acid results during treatment and the follow-up period were blinded.

Efficacy was assessed via collection of blinded blood samples to measure sBAs and by eDiary responses to record pruritus (pruritus responses were rated from 0-4; higher scores indicate worse symptoms). Blood samples to measure fasting serum bile acids were drawn at all visits and were processed by a central laboratory using a validated commercial assay (Diazyme Laboratories; Poway, Calif., USA). Patients were asked to fast for ≥4 hours prior to sample collection. Safety assessments included adverse events (AEs), laboratory monitoring, and physical examinations.

Secondary efficacy endpoints included change from baseline to week 24 in serum bile acids, serum alanine aminotransferase (ALT), and growth; the proportion of patients with a pruritus response at week 24 (i.e., ≥1-point drop on the ObsRO pruritus measure); the number of patients undergoing surgical interruption of the enterohepatic circulation or liver transplantation; and change in sleep parameters based on ObsRO assessments.

Growth was based on Z-scores for height and weight, with change in growth assessed by comparison to standard growth curves.

Exploratory endpoints included change from baseline to week 24 in total bilirubin, aspartate aminotransferase (AST), and gamma glutamyl-transferase; change in select markers of bile acid synthesis (i.e., autotaxin, plasma 7α hydroxy-4-cholesten-3-one [C4]); and change in liver pathology scores (i.e., AST to platelet ratio index [APRI], Fibrosis-4 [FIB-4], and pediatric end-stage liver disease/model for end-stage liver disease [PELD/MELD]).

Blood samples for autotaxin and plasma C4 levels were taken in children whose body weight was >10 kg. An APRI score was used to measure fibrosis of the liver. The lower the APRI score (<0.5), the greater the negative predictive value (and ability to rule out cirrhosis), and the higher the value (>1.5), the greater the positive predictive value (and ability to rule in cirrhosis). The FIB-4 score estimates the amount of scarring in the liver. A FIB-4 score <1.45 has a negative predictive value of 90% for advanced fibrosis, while a score >3.25 has a positive predictive value of 65% for advanced fibrosis. 5 PELD/MELD scores were used to estimate relative hepatic disease severity and the probability of survival for patients awaiting liver transplantation. The PELD score, for patients <12 years of age, ranges across negative to positive values (e.g., from −10 to 50) and takes into account the following test results: albumin, bilirubin, INR, growth, and age. The MELD score, for patients ≥12 years, ranges from 6 to 40 and takes into account the following test results: serum creatinine, bilirubin, INR, and serum sodium. Lower scores for each represent less severe hepatic disease.

Safety

The primary safety analysis for PEDFIC 1 was based on the incidence of treatment-emergent adverse events (TEAEs). TEAEs were categorized by causality, severity, and seriousness for odevixibat and placebo. Other safety assessments included physical examinations, vital signs, laboratory tests, and abdominal ultrasounds (liver and spleen).

Statistical Analyses

Descriptions of statistical analyses, including sample size calculations and how inferential and descriptive measures were applied. The planned sample size was 60 to 70 patients to yield ≥20 evaluable patients per treatment arm; for each primary endpoint, simulations with 5000 iterations using 20 patients per arm were conducted to estimate the power after multiplicity adjustment, resulting in a standard error of <0.7% for each estimated power.

Analysis of Efficacy and Safety Outcomes

For the primary efficacy variable of proportion of positive pruritus assessments at the patient level over the 24-week treatment period, an analysis of covariance (ANCOVA) model was used that included treatment arm and rounded AM and PM baseline pruritus scores as covariates, and treatment group and stratification factors (i.e., PFIC type and age category [0.5 to 5 years; 6 to 12 years; 13 to 18 years]) as fixed effects. The AM baseline score was the mean AM score for the 14 days prior to the first dose of study medication, and the same approach was used for deriving the PM baseline score. There were a total of 336 possible AM and PM scores for each individual over the 24-week treatment period. For patients who rolled over early into the PEDFIC 2 extension study, all pruritus assessments after the early rollover time point were considered negative. Least squares (LS) mean (SE) by treatment arm, 95% CIs, and P values, where applicable, were calculated.

For the primary efficacy variable of fasting serum bile acid response, a Cochran-Mantel-Haenszel test stratified by PFIC type and age category (0.5 to 5 years; 6 to 12 years; 13 to 18 years) was performed at the end of treatment to compare the two odevixibat groups to placebo (see additional details in next paragraph). Baseline for fasting serum bile acids was calculated as the average of the last two values prior to the first dose of study drug; the end value was calculated by averaging the values at weeks 22 and 24. All patients who rolled over early into the PEDFIC 2 extension study and had missing data at this time point were considered nonresponders for the primary efficacy endpoint for serum bile acids. The proportion of patients with response, Clopper-Pearson exact 95% CIs, and P values, where applicable, were calculated.

For each primary endpoint, a closed-testing procedure was used to control for type I error as follows: the low- and high-dose groups were pooled and compared with placebo first; if the one-sided P value was ≤0.025, one sided P values for low dose versus placebo and high dose versus placebo were calculated, respectively. P values presented here have been converted to 2-sided P values by multiplying one-sided P values by two.

Secondary endpoints, exploratory endpoints, subgroup analyses, and safety data were summarized descriptively. Adverse events (AEs) were coded using Medical Dictionary for Regulatory Activities version 23.0.

Results

Patients

Patient Disposition

Study disposition and baseline characteristics are provided in FIGS. 2 and 3, and Table 1A. A total of 62 patients were randomized; 20, 23, and 19 to placebo, odevixibat 40 μg/kg/day, and odevixibat 120 μg/kg/day, respectively. Overall, 49 (79%) completed the 24-week treatment period (FIG. 2). Eleven patients (placebo, N=5; odevixibat 40 μg/kg/day, N=4; odevixibat 120 μg/kg/day, N=2) discontinued treatment due to patient or caregiver judgment of no improvement or intolerable symptoms (i.e., perceived lack of efficacy, as patients and clinicians were blinded to study outcomes until the last patient completed the study) and rolled over into the long-term extension study prior to completing 24 weeks of treatment. Additionally, one patient treated with odevixibat 40 μg/kg/day discontinued due to noncompliance and inability to travel to the clinic, and one patient treated with odevixibat 120 μg/kg/day discontinued early due to a TEAE of diarrhea.

Patient demographics and baseline characteristics are depicted in Table 1A. Median (range) age of the patients in Trial 1 was 3.2 years (0.5 to 15.9 years; 76% were aged ≤5 years); 50% were male and 84% were white. 27% of patients had PFIC Type 1 and 73% had PFIC Type 2, with an overall median time since diagnosis of 1.5 years. At baseline (study entry), 81% of patients were treated with ursodeoxycholic acid (UDCA), 66% with rifampicin, and 89% with UDCA and/or rifampicin. Baseline hepatic impairment per Child-Pugh classification was mild in 66% and moderate in 64% of patients. Baseline mean (SD) eGFR was 164 (30.6) mL/min/1.73 m². Baseline mean (SD) ALT, AST and bilirubin levels were 100 (116.8) U/L, 101 (69.8) U/L, and 3.2 (3.57) mg/dL, respectively. See FIG. 3. Baseline mean (SD) pruritus score (range: 0-4) and serum bile acids levels were similar in odevixibat-treated patients (2.9 [0.09] and 103 [8.2] µg/mL, respectively) and placebo-treated (3.0 [0.14] and 101 [9.2] µg/mL, respectively). See FIG. 3.

Figure 4A:
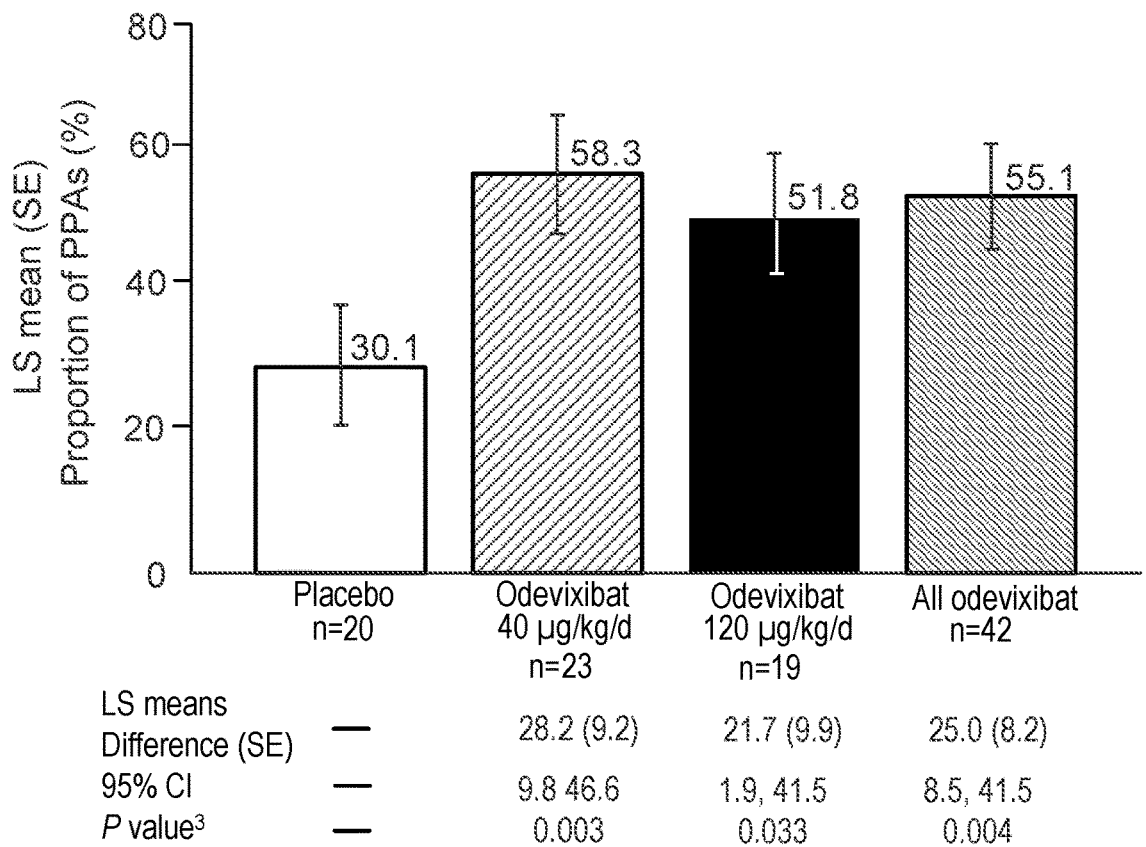
FIG. 4A is a bar graph showing the proportion of positive pruritus assessments (PPAs) at the patient level following 24 weeks of treatment with odevixibat. PPAs are defined as a scratching score of ≤1 or a ≥1-point drop from baseline on an observer-reported instrument. LS refers to least squares.

Consistent with the potential for patients with PFIC to experience impaired growth, median height-for-age and weight for-age Z-scores were −1.7 and −1.0 at baseline, respectively, indicating that patients were below their age-matched peers for growth. At baseline, median serum bile acids, serum ALT, and total bilirubin levels were considerably elevated above normal limits (Table 1A), indicating cholestasis. There were some differences in certain characteristics at baseline between the placebo and odevixibat groups (e.g., ALT levels, use of UDCA or rifampicin), although these were not stratification factors used in randomization.

versus placebo (FIGS. 4 and 5). Treatment with odevixibat overall, and separately, at doses of 40 µg/kg/day and 120 µg/kg/day, led to statistically significant improvements in pruritus compared with placebo over the 24 week treatment period based on the ObsRO instrument: the least square mean proportion of positive pruritus assessments at the patient level was 55% for the all-odevixibat group (P=0.004; 58% and 52% in the odevixibat 40 and 120 µg/kg/day groups, respectively) compared with 30% with placebo (FIG. 4A). In particular, as shown in FIG. 4A, the least squares mean treatment difference in the proportion of positive pruritus assessments over 24 weeks between odevixibat 40 µg/kg/day and placebo was 28.2% (95% CI 9.2, 46.6; one-sided P=0.0019) and between odevixibat 120 µg/kg/day and placebo was 21.7% (95% CI 1.9, 41.5; one-sided P=0.0163). Mean pruritus score change from baseline to end of treatment was −1.13 with odevixibat vs −0.25 with placebo.

Figure 4B:
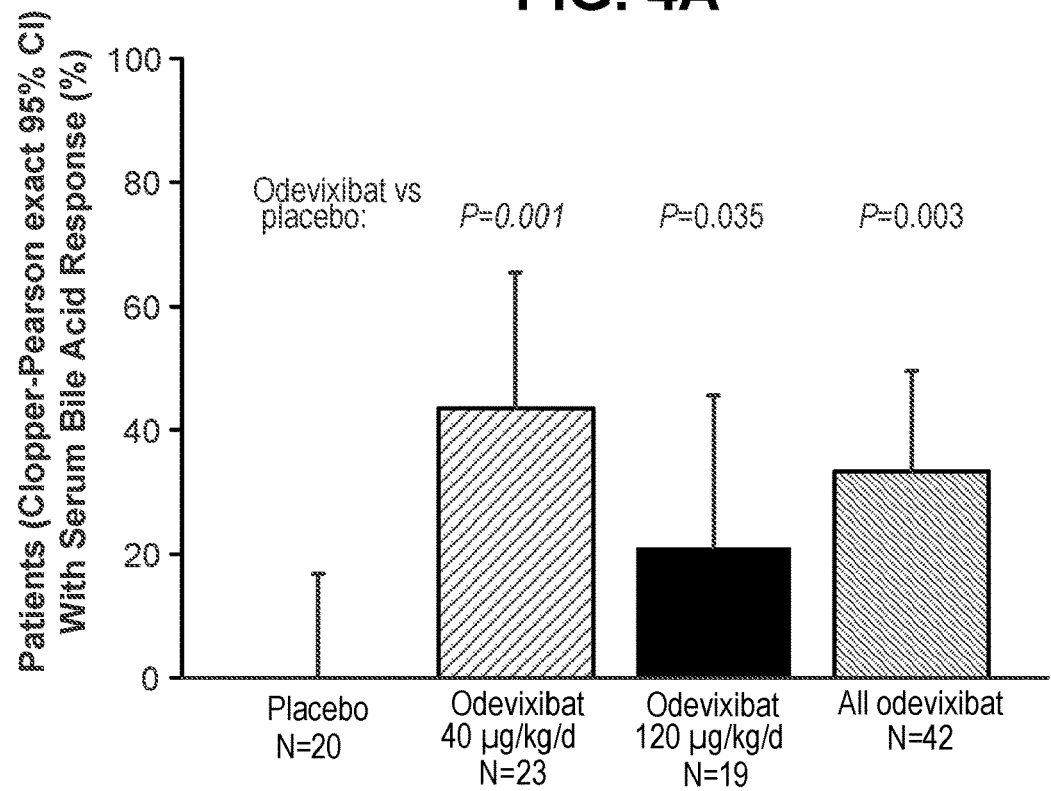
FIG. 4B is a bar graph showing the rate of serum bile acid response at the patient level following 24 weeks of treatment with odevixibat. Serum bile acid response was defined as serum bile acids ≤70 μmol/L at week 24 or a reduction from baseline to week 24 of ≥70%.

After 24 weeks of treatment, the rate of serum bile acid response was also significantly higher in the all-odevixibat group compared with placebo (P=0.003; FIG. 4B). The

TABLE 1A

Patient Demographics and Baseline Characteristics

| | Placebo, N = 20 | Odevixibat 40 µg/kg/day, N = 23 | Odevixibat 120 µg/kg/day, N = 19 | Odevixibat, all doses, N = 42 |
|---|---|---|---|---|
| Age, median (range), yr | 2.8 (0.5-15) | 3.2 (0.6-16) | 4.9 (1-13) | 3.2 (0.6-16) |
| Age category, n (%) | | | | |
| 0.5-5 years | 16 (80) | 17 (74) | 14 (74) | 31 (74) |
| 6-12 years | 3 (15) | 5 (22) | 4 (21) | 9 (21) |
| 13-≤18 years | 1 (5) | 1 (4) | 1 (5) | 2 (5.0) |
| Female, no. (%) | 8 (40) | 12 (52) | 11 (58) | 23 (55) |
| Race, no. (%) | | | | |
| White | 17 (85) | 18 (78) | 17 (90) | 35 (83) |
| Black | 0 | 2 (9) | 0 | 2 (5) |
| Asian | 1 (5) | 0 | 1 (5) | 1 (2) |
| Other | 2 (10) | 3 (13) | 1 (5) | 4 (10) |
| Height, mean (SD), cm | 89.0 (24.4) | 92.3 (20.2) | 98.5 (22.8) | 95.1 (21.4) |
| Weight, mean (SD), kg | 14.5 (9.8) | 15.5 (9.8) | 17.6 (9.6) | 16.4 (9.6) |
| PFIC type, no. (%) | | | | |
| PFIC1 | 5 (25) | 7 (30) | 5 (26) | 12 (29) |
| PFIC2 | 15 (75) | 16 (70) | 14 (74) | 30 (71) |
| Use of UDCA at baseline, no. (%) | 18 (90) | 19 (83) | 13 (68) | 32 (76) |
| Use of rifampicin at baseline, no. (%) | 17 (85) | 13 (57) | 11 (58) | 24 (57) |
| Serum bile acids, median (range), µmol/L[a, b] | 255 (57-435) | 228 (76-605) | 189 (36-600) | 221 (36-605) |
| Pruritus score, median (range)[c] | 3.0 (1.9-4.0) | 3.0 (2.0-4.0) | 2.9 (1.6-3.4) | 3.0 (1.6-4.0) |
| Serum ALT, median (range), U/L[d] | 56 (19-236) | 83 (21-798) | 59 (16-314) | 70 (16-798) |
| Total bilirubin, mean (range), mg/dL[e] | 1.8 (0.3-11.4) | 2.8 (0.3-12.7) | 1.5 (0.2-18.6) | 2.2 (0.2-18.6) |

[a]Normal reference range: 0-10 µmol/L.
[b]Baseline measurements differed from criteria used to determine eligibility (i.e., to be eligible, patients must have a serum bile acid level ≥100 µmol/L based on the average of two samples taken during screening visits; the baseline serum bile acid level was calculated by averaging the last two values prior to the first dose of study drug [value prior to treatment on day 1 and the second screening value]).
[c]Baseline measurements differed from criteria used to determine eligibility (i.e., to be eligible, patients' worst daily pruritus score as observed by caregivers had to be ≥2 in the two weeks prior to randomization; baseline pruritus score was calculated as the average of AM and PM scores in the 14 days prior to the first dose of study drug).
[d]Normal reference range varies by age and sex, but typical values for pediatrics are in the range of 1-35 U/L.
[e]Normal reference range: ≤1.2 mg/dL.
ALT, alanine aminotransferase; PFIC, progressive familial intrahepatic cholestasis; UDCA, ursodeoxycholic acid.

Efficacy

Primary Endpoints

The study met both primary endpoints. Significant improvements in pruritus were observed with odevixibat mean proportion of patients achieving a serum bile acid response was 33% in all patients who received odevixibat (including 44% and 21% of patients in the odevixibat 40 and 120 µg/kg/day groups, respectively), whereas no patients receiving placebo met this response threshold.

Other Efficacy Endpoints

Figure 5A:
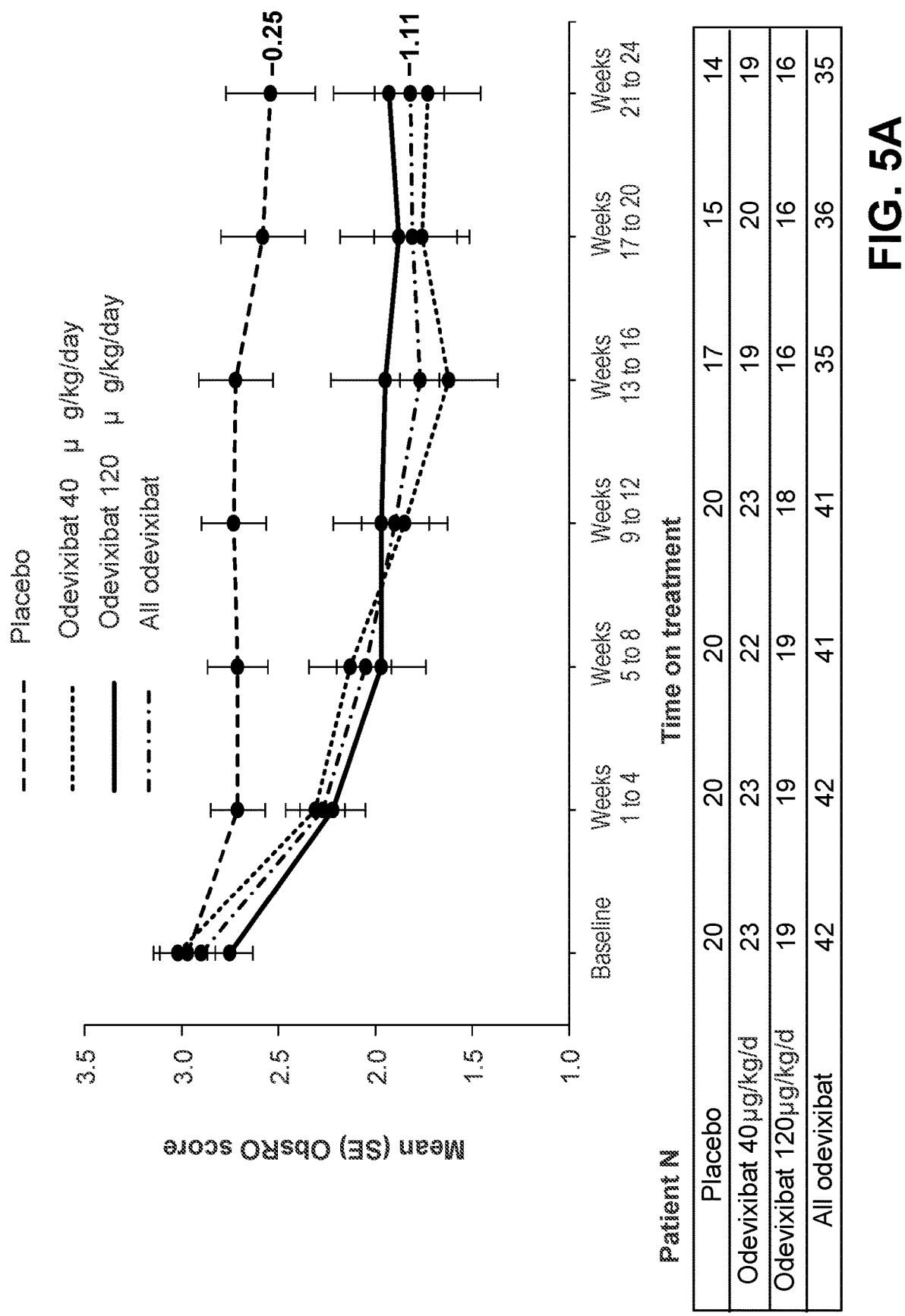
FIG. 5A is a line graph showing the mean pruritus score change from baseline to end of treatment. A clinically meaningful change in pruritus score is defined as a ≥1-point decrease in ObsRO scratching score. The green and blue values depict the mean changes from baseline in the odevixibat and placebo groups, respectively, at the last time point assessed. ObsRO, observer-reported outcome.
Figure 5B:
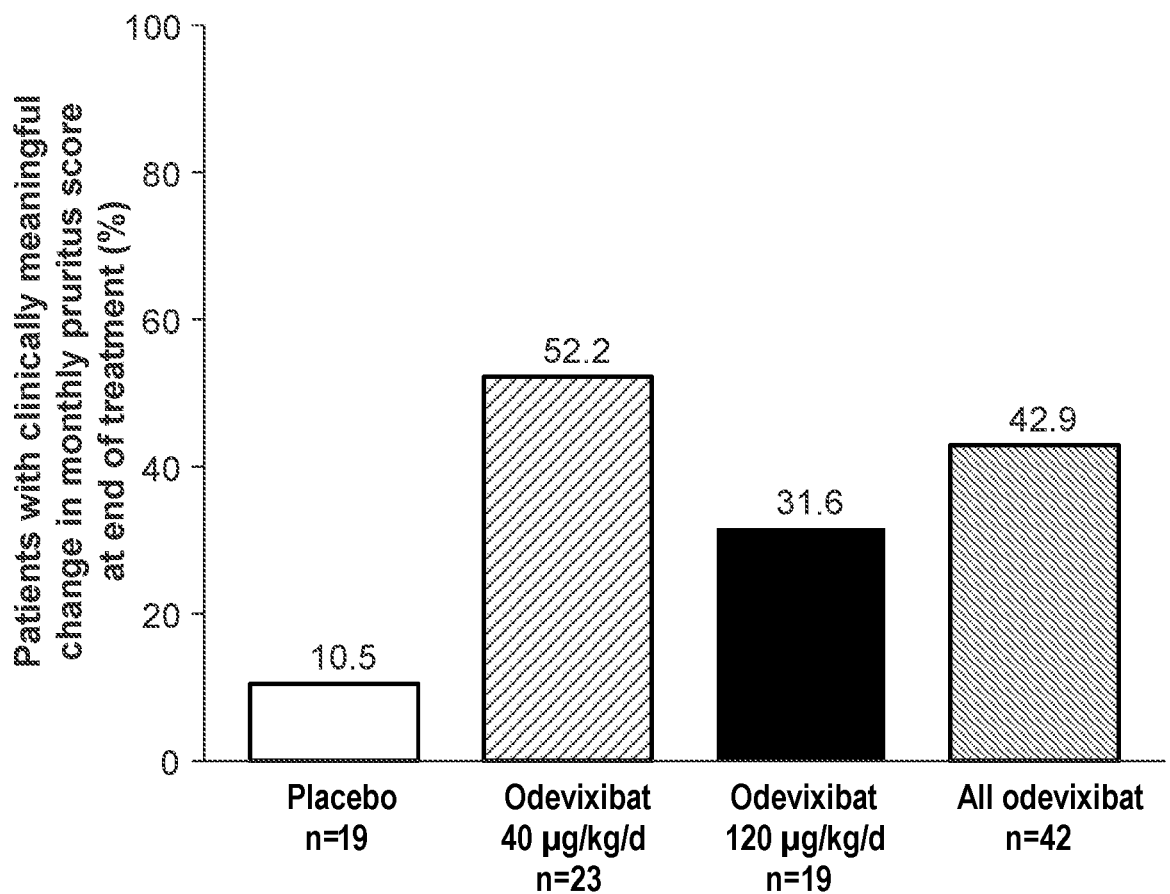
FIG. 5B is a bar graph showing the proportion of patients with clinically meaningful change in monthly pruritus score at the end of treatment. A clinically meaningful change in pruritus score is defined as a ≥1-point decrease in ObsRO scratching score.

Improvement in pruritus among odevixibat-treated patients based on mean monthly ObsRO scratching score was observed by week 4 of treatment; the mean (SE) change from baseline to weeks 21 through 24 in ObsRO pruritus score was −1.11 (0.2) with odevixibat versus −0.25 (0.2) with placebo (FIG. 5A). Additionally, a greater proportion of patients treated with odevixibat had a clinically meaningful change in pruritus at week 24 based on mean monthly score than did patients treated with placebo (43% vs 11%, respectively; FIG. 5B).

Figure 6:
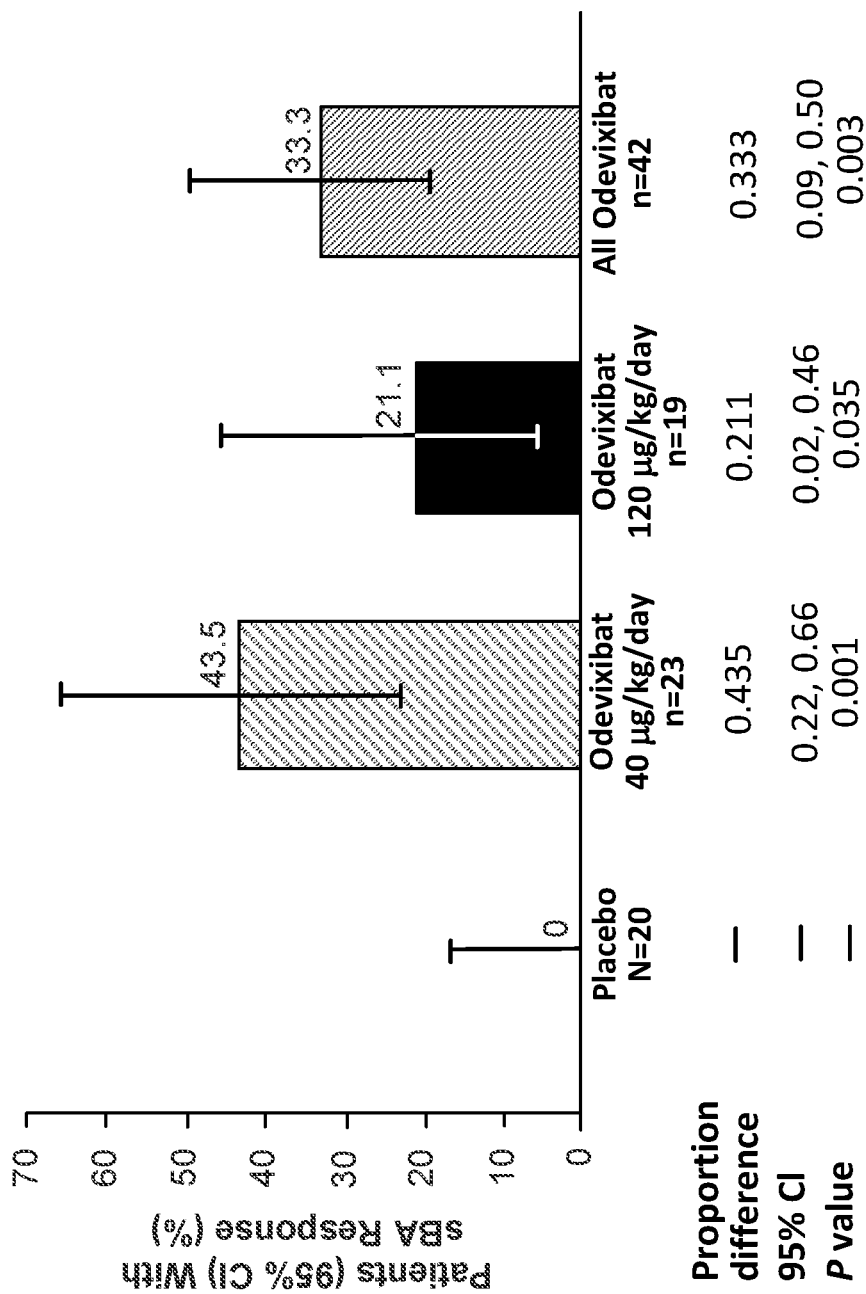
FIG. 6 is a bar graph showing the serum bile acid (sBA) response following 24 weeks of treatment with odevixibat. sBA response is defined as sBAs ≤70 μmol/L at week 24 or a reduction from baseline to week 24 of ≥70%.
Figure 7:
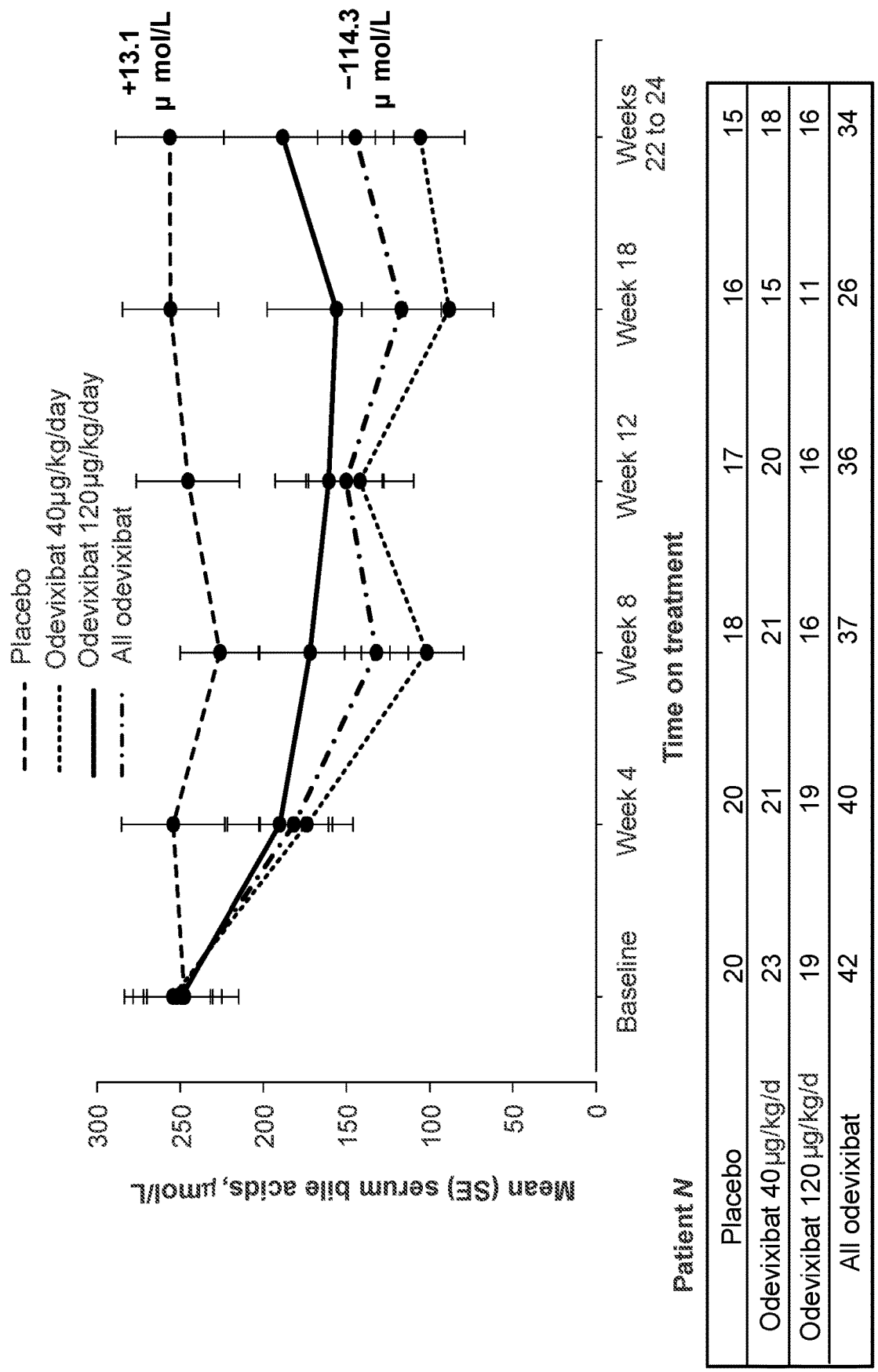
FIG. 7 is a line graph of the mean fasting serum bile acid (sBA) concentration (μmol/L) over time. The green and blue values depict the mean changes from baseline in the odevixibat and placebo groups, respectively, at the last time point assessed. ObsRO, observer-reported outcome.

For serum bile acids, significantly higher percentages of patients achieved a sBA response with odevixibat vs placebo (FIGS. 6 and 7). Changes from baseline in serum bile acids were also observed as early as week 4 of odevixibat treatment; at weeks 22 through 24, mean serum bile acid levels decreased by 114.3 μmol/L in the all odevixibat group and increased by 13.1 μmol/L with placebo (FIG. 7). The mean percentage difference in patients who met the serum bile acid reduction endpoint between odevixibat 40 μg/kg/day and placebo was 44.1% (95% CI 23.6, 64.6; one-sided P=0.0015) and between odevixibat 120 μg/kg/day and placebo was 21.6% (one-sided P=0.0174). Mean sBAs were reduced with odevixibat (−114.3 μmol/L) vs increased with placebo (13.1 μmol/L) at end of treatment.

Figures 8A, 8B:
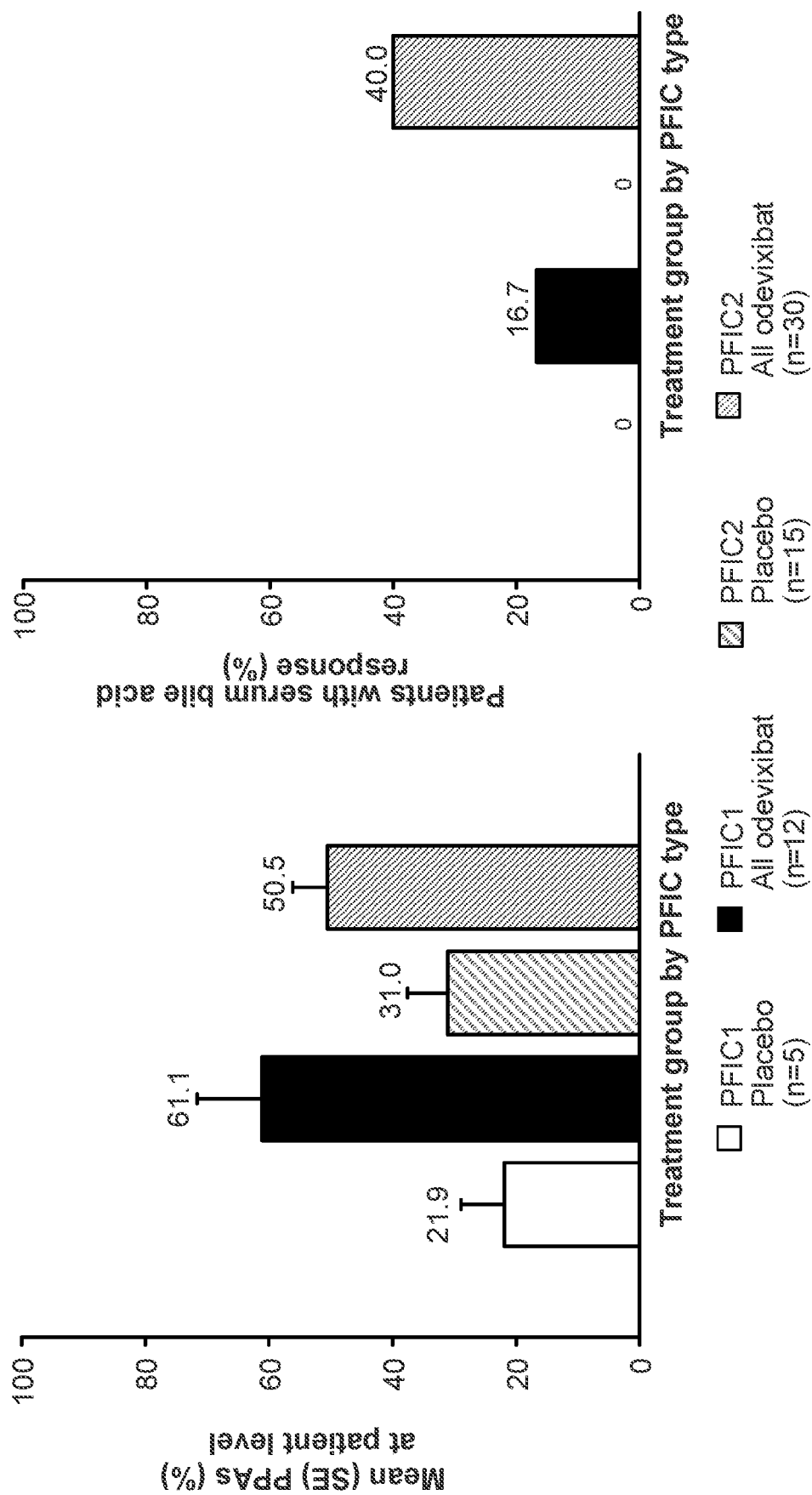
FIG. 8A and FIG. 8B illustrate the magnitude of treatment effects (FIG. 8A: pruritus and FIG. 8B: serum bile acid) across PFIC subtypes. A positive pruritus assessment (PPA) was defined as a scratching score of ≤1 or a ≥1-point drop from baseline on the ObsRO instrument. Serum bile acid response was defined as serum bile acids ≤70 μmol/L at week 24 or a reduction from baseline to week 24 of ≥70%.

Subgroup analyses were performed to assess treatment responses in patients with PFIC1 or PFIC2. For both pruritus and sBA, the magnitude of treatment effects were similar in patients with PFIC1 or PFIC2 (FIG. 8A; FIG. 8B). The mean proportion of positive pruritus assessments in odevixibat-treated patients with PFIC1 during 24 weeks of treatment was higher than that in patients with PFIC1 treated with placebo; similar effects were observed for odevixibat-versus placebo-treated patients with PFIC2 (FIG. 8A). The proportions of odevixibat-treated patients with PFIC1 and PFIC2 who met serum bile acid response criteria at week 24 were 17% and 40%, respectively, whereas no placebo-treated patients in either subgroup achieved a serum bile acid response (FIG. 8B).

Treatment with odevixibat led to reductions from baseline in standard liver-associated tests: at week 24, mean (SE) changes in serum ALT were −26.7 (14.0) U/L with odevixibat and 3.7 (5.0) U/L with placebo; changes in additional hepatic parameters, biochemical markers of bile acid synthesis, and measures of liver pathology are presented in Table 1B. None of the 62 patients underwent surgical interruption of the enterohepatic circulation or liver transplantation during the study.

TABLE 1B

Summary of Change From Baseline to Week 24 in Hepatic Parameters, Biochemical Markers of Bile Acid Synthesis, and Measures of Liver Pathology

| | Placebo, N = 20 | | Odevixibat 40 μg/kg/day, N = 23 | | Odevixibat 120 μg/kg/day, N = 19 | | Odevixibat, all doses, N = 42 | |
|---|---|---|---|---|---|---|---|---|
| | n | Mean (SE) | n | Mean (SE) | n | Mean (SE) | n | Mean (SE) |
| Total bilirubin, mg/dL | | | | | | | | |
| Baseline | 20 | 3.1 (0.8) | 23 | 3.1 (0.6) | 19 | 3.3 (1.1) | 42 | 3.2 (0.6) |
| Change to week 24 | 11 | −0.6 (0.9) | 17 | −1.4 (0.6) | 15 | −1.1 (0.8) | 32 | −1.3 (0.5) |
| Serum AST, U/L | | | | | | | | |
| Baseline | 20 | 90 (12) | 23 | 114 (17) | 19 | 96 (16) | 42 | 106 (12) |
| Change to week 24 | 11 | 5 (6) | 17 | −37 (12) | 15 | −27 (19) | 32 | −32 (11) |
| GGT, U/L | | | | | | | | |
| Baseline | 20 | 17 (1) | 23 | 20 (2) | 19 | 19 (2) | 42 | 19 (1) |
| Change to week 24 | 11 | 2 (1) | 17 | −3 (2) | 15 | −1 (1) | 32 | −2 (1) |
| Autotaxin, ng/mL | | | | | | | | |
| Baseline | 16 | 2294 (282) | 19 | 2915 (347) | 15 | 2191 (272) | 34 | 2595 (233) |
| Change to week 24 | 12 | −59 (227) | 14 | −1698 (486) | 12 | −1018 (375) | 26 | −1384 (315) |
| C4, ng/mL | | | | | | | | |
| Baseline | 16 | 5.7 (1.6) | 18 | 4.3 (0.9) | 14 | 5.2 (1.2) | 32 | 4.7 (0.7) |
| Change to week 24 | 12 | 4.9 (4.6) | 15 | 15.7 (5.2) | 12 | 15.8 (9.2) | 27 | 15.7 (4.9) |
| APRI | | | | | | | | |
| Baseline | 15 | 0.5 (0.1) | 21 | 0.5 (0.1) | 13 | 0.7 (0.1) | 34 | 0.6 (0.1) |
| Change to week 24 | 8 | 0.0 (0.1) | 15 | −0.1 (0.1) | 8 | 0.0 (0.2) | 23 | −0.1 (0.1) |
| FIB-4 | | | | | | | | |
| Baseline | 15 | 0.1 (0.0) | 21 | 0.1 (0.0) | 13 | 0.2 (0.1) | 34 | 0.1 (0.0) |
| Change to week 24 | 8 | 0.0 (0.0) | 15 | 0.0 (0.0) | 8 | 0.1 (0.1) | 23 | 0.0 (0.0) |
| PELD/MELD | | | | | | | | |
| Baseline | 20 | −0.8 (1.7) | 22 | −2.9 (1.4) | 19 | 0.2 (1.9) | 41 | −1.5 (1.1) |
| Change to week 24 | 11 | −0.7 (1.1) | 15 | −2.4 (1.0) | 14 | −1.1 (1.2) | 29 | −1.8 (0.8) |

APRI, AST to platelet ratio index; AST, aspartate aminotransferase; C4, 7alpha-hydroxy-4-cholesten-3-one; FIB-4, Fibrosis-4; GGT, gamma glutamyl-transferase; PELD/MELD, Pediatric End-Stage Liver Disease/Model for End-Stage Liver Disease.

Table 1C presents the results of the comparison of the key efficacy results in this study between odevixibat and placebo.

TABLE 1C

Comparison of Key Efficacy Results for odevixibat vs Placebo Over the 24-Week Treatment Period in Patients with PFIC

| Efficacy Endpoint | Placebo (n = 20) | odevixibat 40 μg/kg/day (n = 23) | odevixibat 120 μg/kg/day (n = 19) | Total (N = 42) |
|---|---|---|---|---|
| Proportion of Positive Pruritus Assessments Over the Treatment Period | | | | |
| Mean (SE) | 28.74 (5.209) | 58.31 (6.205) | 47.69 (8.110) | 53.51 (5.006) |
| Mean Difference vs Placebo (95% CI)[a] | | 28.23 (9.182) (9.83, 46.64) | 21.71 (9.892) (1.87, 41.54) | 24.97 (8.240) (8.45, 41.49) |
| One-sided p-value[b] | — | 0.0019 | 0.0163 | 0.0019 |
| Proportion of Patients with Reduction in Serum Bile Acids at End of Treatment | | | | |
| n (%) | 0 | 10 (43.5) | 4 (21.1) | 14 (33.3) |
| (95% CI) | (0.00, 16.84) | (23.19, 65.51) | (6.05, 45.57) | (19.57, 49.55) |
| % Difference vs Placebo (95% CI) | | 0.441 (0.2361, 0.6464) | 0.216 (−0.0050, 0.4380) | 0.307 (0.1260, 0.4879) |
| One-sided p-value[c] | | 0.0015 | 0.0174 | 0.0015 |

[a]Based on least squares means
[b]Based on analysis of covariance model with daytime and nighttime baseline pruritus scores as covariates and treatment group and stratification factors (PFIC Type and age category) as fixed effects. P-values for the dose groups were adjusted for multiplicity.
[c]Based on Cochran Mantel Haenszel test stratified by PFIC Type and age category. P-values for the dose groups were adjusted for multiplicity.

Mean (SE) changes from baseline to end of treatment in height z-scores were 0.29 (0.106) and 0.15 (0.124) in the odevixibat 40 and 120 μg/kg/day groups, respectively, and 0.10 (0.102) in the placebo group. Treatment with odevixibat over 24 weeks improved growth relative to placebo. Mean (SE) change from baseline to week 24 in height Z-score was 0.0 (0.1) for patients treated with odevixibat and −0.2 (0.1) for patients receiving placebo. Mean (SE) change from baseline to week 24 in weight Z-score was 0.2 (0.1) for patients treated with odevixibat and 0.1 (0.1) for patients receiving placebo.

Consistent with improvements observed with pruritus, treatment with odevixibat improved sleep parameters for patients based on caregiver-reported information. Odevixibat reduced the percentage of days the patient required soothing, and patients less often required help falling asleep and had fewer days needing to sleep with a caregiver (mean [SE] changes from baseline to end of treatment in the percentage of days with help falling asleep were −51.8 [9.86], −32.6 [14.57] and −3.2 [2.89] for 40 μg/kg/day, 120 μg/kg/day and placebo), respectively; in percentage of days requiring soothing were −51.5% [10.32], −34.9% [13.37] and −7.6% [6.18], respectively; and in percentage of days sleeping with the caregiver were −49.4% [10.47], −33.1% [11.80] and −5.5% [4.84], respectively.

At baseline, patients typically needed help falling asleep (percentage of days: odevixibat overall, 82%; placebo, 74%), needed soothing (84%; 73%), or slept with their caregiver (73%; 58%) based on caregiver report. During the treatment period, mean reductions from baseline in these sleep parameters were larger (i.e., more improved) with odevixibat versus placebo; changes from baseline with placebo were minimal. For example, by weeks 21 to 24 of treatment, mean changes from baseline for odevixibat versus placebo were −43% versus −3% for percentage of days needing help falling asleep; −44% versus −8% for percentage of days with soothing; and −42% versus −6% for percentage of days sleeping with the caregiver.

Additionally, caregivers rated patients' daytime tiredness using a 5-point scale that ranged from 0 ("not tired at all") to 4 ("very, very tired"). At baseline, all patients had moderate daytime tiredness (mean score: odevixibat overall, 2.3; placebo, 2.7). A greater mean reduction (i.e., improvement) from baseline to weeks 21 to 24 was observed with odevixibat compared with placebo (−0.99 versus −0.49, respectively). On the sleep outcomes of percentage of days seeing blood due to scratching, number of awakenings, or percentage of days taking medications to induce sleep, no clear differences were noted between treatment groups. For these parameters, there was wide variability in both baseline and end-of-treatment values.

Mean (SE) changes from baseline to end of treatment in ALT were −27.9 (17.97) U/L and −25.3 (22.47) U/L for odevixibat 40 and 120 μg/kg/day, and 3.7 (4.95) U/L for placebo.

Safety

Overall, 35 (83%) of the 42 patients receiving odevixibat experienced at least one treatment ending adverse event (TEAE); a similar rate was observed in patients receiving placebo (17/20; 85%; Table 2). The overall rate of TEAEs was similar between odevixibat dose groups. Most TEAEs were mild or moderate in severity. The most commonly reported TEAEs (occurring in ≥10% of patients overall) were diarrhea/frequent bowel movements (odevixibat vs placebo: 31% vs 10%), fever (29% vs 25%), upper respiratory tract infection (19% vs 15%), vomiting (17% vs 0%), ALT increase (14% vs 5%), and serum bilirubin increase (12% vs 10%).

In total, 33.3% of TEAEs with odevixibat and 15.0% with placebo were considered related to study drug by the investigator. Treatment-related AEs of diarrhea or frequent bowel movement occurred in 9.5% of odevixibat-treated patients and 5.0% of placebo-treated patients. No deaths, treatment-related serious AEs, or TEAEs related to liver decompensation occurred. One patient in the odevixibat 120 μg/kg/day arm discontinued due to an AE of diarrhea. See Table 2.

TABLE 2

Safety

| Patients, n (%) | Placebo n = 20 | Odevixibat 40 µg/kg/day n = 23 | Odevixibat 120 µg/kg/day n = 19 | Odevixibat, All doses n = 42 |
|---|---|---|---|---|
| Any TEAE | 17 (85.0) | 19 (82.6) | 16 (84.2) | 35 (83.3) |
| Mild | 6 (30.0) | 11 (47.8) | 8 (42.1) | 19 (45.2) |
| Moderate | 9 (45.0) | 7 (30.4) | 6 (31.6) | 13 (31.0) |
| Severe | 2 (10.0) | 1 (4.3) | 2 (10.5) | 3 (7.1) |
| Drug-related TEAE | 3 (15.0) | 7 (30.4) | 7 (36.8) | 14 (33.3) |
| Serious TEAEs | 5 (25.0) | 0 | 3 (15.8) | 3 (7.1) |
| TEAEs leading to discontinuation | 0 | 0 | 1 (5.3) | 1 (2.4) |
| Liver-related TEAEs | 4 (20.0) | 5 (21.7) | 6 (31.6) | 11 (26.2) |
| Drug-related TEAEs occurring in 2 or more patients in a group, by preferred term | | | | |
| ALT increased | 1 (5.0) | 2 (8.7) | 2 (10.5) | 4 (9.5) |
| AST increased | 1 (5.0) | 2 (8.7) | 1 (5.3) | 3 (7.1) |
| Blood bilirubin increased | 1 (5.0) | 2 (8.7) | 2 (10.5) | 4 (9.5) |
| Diarrhea/frequent bowel movements | 1 (5.0) | 2 (8.7) | 2 (10.5) | 4 (9.5) |

CONCLUSIONS

Treatment with odevixibat at doses of 40 and 120 µg/kg/day led to statistically significant reductions in pruritus symptoms and sBAs over 24 weeks compared with placebo in children with PFIC1 or PFIC2. These improvements occurred rapidly and were sustained during continued treatment. Odevixibat at doses of 40 and 120 µg/kg/day was well tolerated over 24 weeks with most TEAEs being mild to moderate in severity and not dose limiting. The safety profile of odevixibat was comparable in the 40 and 120 µg/kg/day dose groups. Overall, this phase 3 study suggests that odevixibat has the potential to provide significant treatment benefits in a disease with high unmet medical needs.

Two potentially serious features of PFIC are cholestasis leading to progressive hepatic damage and unrelenting pruritus. Excess retained intrahepatic bile acids (reflected in elevated serum bile acids) have been associated with, and are thought to contribute to, the progressive hepatic damage seen in these children. Surgical interruption of the enterohepatic circulation can reduce serum bile acids and pruritus, as well as improve other clinical outcomes; importantly, patients who achieved lower serum bile acids following such diversion surgery have extended survival with their native livers. However, the response to biliary diversion can wane over time, and many patients experience recurring cholestasis or pruritus post-surgery. Liver transplantation is considered when patients with PFIC have end-stage liver disease, hepatocellular carcinoma, or pruritus unresponsive to off-label medical therapy or biliary diversion surgery. However, liver transplantation may not be curative in all patients.

In the present study, odevixibat-associated reductions in pruritus were clinically meaningful. Interestingly, odevixibat also reduced levels of autotaxin, a proposed pruritogen, by approximately half with 24 weeks of treatment. In addition, to the extent that accumulation of bile acids contributes to ongoing liver damage, reduction of bile acid levels by odevixibat could also result in improved hepatic health and delay of liver transplantation; this potential is also supported by the improvement in hepatic biochemical parameters observed in patients receiving odevixibat. Therefore, odevixibat may have the potential to delay, or even prevent, liver transplantation in this patient population.

The findings on pruritus should be considered in light of general limitations associated with subjective measures; however, these study results are strengthened by several factors, namely: inclusion of a placebo control and positive findings on two primary endpoints, with one based on subjective measurement of symptoms and the other based on a biologic parameter. In addition, due to the study's eligibility criteria (i.e., exclusion of patients with extreme perturbations in hepatic parameters), these study findings may not be fully generalizable to all patients with PFIC with these characteristics.

Although part of this study was conducted during the COVID-19 pandemic, no patient was lost to follow-up during this time. Overall, most patients (79%) completed the treatment period, with 18% rolling over early to the ongoing long-term extension study, PEDFIC 2. PEDFIC 2 includes patients from PEDFIC 1 and new patients with any type of PFIC; at the planned interim data cut, 69 patients had received open-label treatment with odevixibat (median exposure: 36 weeks), which was generally well tolerated, with sustained clinical benefits observed.

Odevixibat, administered as once-daily oral capsules, represents a nonsurgical, pharmacologic option to interrupt the enterohepatic circulation in patients with PFIC. In the PEDFIC 1 study, both primary efficacy endpoints were met and odevixibat 40 or 120 µg/kg/day improved pruritus and reduced serum bile acids relative to placebo. In addition, treatment effects with odevixibat were observed in patients with PFIC1 or PFIC2. There were no unexpected TEAEs observed, and odevixibat was generally well tolerated. Overall, these data suggest that odevixibat has the potential to improve the standard of care in patients with PFIC and provide significant treatment benefits in a disease group with high unmet medical needs.

Example 2—Long-Term Efficacy and Safety of Odevixibat, an Ileal Bile Acid Transporter Inhibitor in Children with Progressive Familial Intrahepatic Cholestasis: Interim Results from PEDFIC 2, an Open-Label Phase 3 Trial After treatment in the first trial (Example 1), patients were eligible to enroll in a second trial, a 72-week open-label extension trial. In this ongoing 72-week open-label extension trial, PFIC patients were treated with odevixibat 120 µg/kg/day. The 69 patients (PFIC1 (26%), PFIC2 (65%) or PFIC3 (7%)) treated with 120 µg/kg/day for up to 48 weeks experienced a durable effect on serum bile acids reduction and improvement in growth velocity based on review of z scores for height, weight and BMI, and improvement in ALT, AST and total bilirubin. The effects were maintained for patients treated for 18 months or longer. The example details the interim analysis through 24 weeks of treatment.

Study Population

Cohorts

Eligible patients were enrolled into 1 of 2 cohorts, based on the following criteria:

Cohort 1: patients who completed 24 weeks of treatment in PEDFIC 1 (or patients who withdrew early from PEDFIC 1 due to intolerable symptoms after a minimum of 12 weeks of treatment in PEDFIC 1). These patients had been previously treated with either odevixibat (40 or 120 µg/kg/day) or placebo in PEDFIC 1 and were designated as "P1O" and "P1P," respectively.

Cohort 2: patients who either did not meet eligibility criteria for PEDFIC 1 or were eligible to enroll in PEDFIC 1 after that study's recruitment had closed; these were newly enrolled patients.

Patients in both the P1P and cohort 2 groups were treatment-naive to odevixibat at the start of this study.

Key Eligibility Criteria

In both cohorts, eligible patients were those with genetically confirmed PFIC, elevated serum bile acids (sBAs; ≥100 µmol/L), and history of significant pruritus (i.e., itching or scratching score of ≥2 per patient/caregiver report using the PRUCISION© instrument).

Those with no functional ABCB11 protein (i.e., bile salt export pump) were excluded.

In addition, patients rolling over from PEDFIC 1 (i.e., cohort 1) must have had a diagnosis of PFIC1 or PFIC2 and must have been between the ages of 0.5-18 years at the start of PEDFIC 1; for patients newly enrolled into PEDFIC 2 (i.e., cohort 2), there were no age or PFIC subtype restrictions.

Study Design

Figure 9:
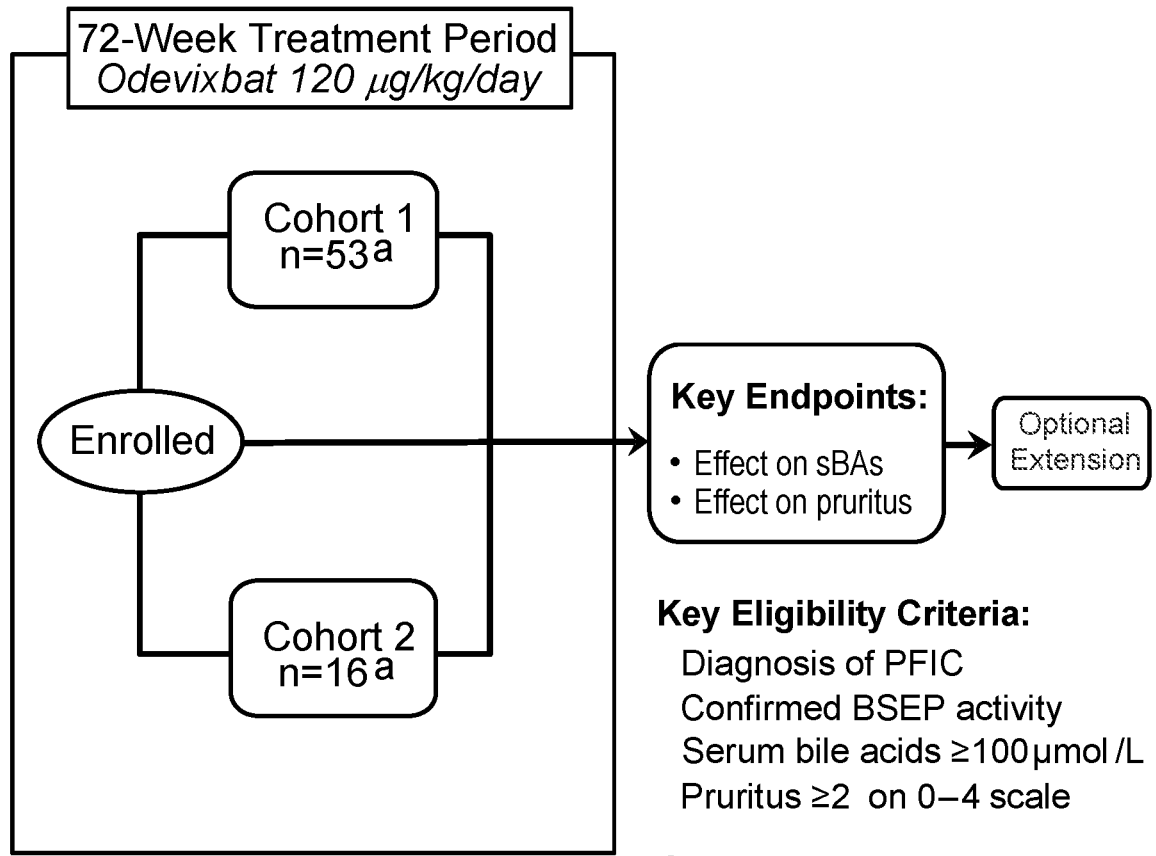
FIG. 9 is a schematic of the study design for PEDFIC2. [a]Patient numbers refer to the number of patients in the interim analysis. BSEP, bile salt export pump; PFIC, progressive familial intrahepatic cholestasis; sBAs, serum bile acids.

This phase 3 study included a screening period (for newly enrolled patients [i.e., cohort 2] only) and a 72-week treatment period (FIG. 9) in which all patients received oral, once-daily odevixibat 120 µg/kg.

Patients returned to the clinic 4 and 12 weeks after the first dose of odevixibat and then approximately every 10 to 12 weeks thereafter.

Following the 72-week treatment period, patients either enrolled in an optional extension for continued treatment or returned for a follow-up visit 4 weeks after ending study drug.

Outcomes, Assessments, and Statistical Analysis

The primary efficacy outcomes were to assess the effects of odevixibat on sBAs and pruritus, including mean changes and proportion of patients meeting response criteria.

sBA responders were defined as patients who achieved a normalization of sBAs or reduction of ≥70%.

Pruritus responders were defined as patients who achieved a ≥1-point drop on the pruritus assessment.

Secondary outcomes included characterizing the long-term safety and tolerability of odevixibat, as well as the effects of odevixibat on growth, biliary diversion and/or liver transplantation, and markers of cholestasis and liver disease.

For the P1O and P1P groups, there were 2 baselines (PEDFIC 1 baseline and PEDFIC 2 baseline); for those in cohort 2, baseline refers to the value prior to initiation of odevixibat in PEDFIC 2.

This interim analysis focuses on data collected after 24 weeks of treatment in PEDFIC 2.

T tests were used to calculate P values for primary outcomes in the P1O group only; other outcomes were summarized descriptively.

Results

Disposition

A total of 69 patients have received treatment in PEDFIC 2 as of the data cut-off date, including 53 patients who rolled over from PEDFIC 1 and 16 newly enrolled patients (i.e., cohort 2)

Overall, 35 patients who entered this study were treatment naive (19 in P1P; 16 in cohort 2).

Most patients were ongoing on treatment (65/69, 92%).

Four patients discontinued treatment as of the data cut-off date: 3 patients in P1O (1 due to withdrawal of consent, 1 due to an adverse event [AE] of cholestasis and subsequent surgical biliary diversion, and 1 due to liver transplantation) and 1 patient in cohort 2 (due to withdrawal of consent and acute pancreatitis).

Demographics & Baseline Characteristics

Table 3 displays patient demographics and characteristics at PEDFIC 1 baseline (for cohort 1) and at PEDFIC 2 baseline (for both cohorts 1 and 2).

At PEDFIC 2 baseline, the median age of all 69 patients was 4.1 years (ranging from 1 to 19.5 years), and more than half of the patients had PFIC2 (n=45, 65%); additionally, 18 patients (16%) had PFIC1, 5 patients (7%) had PFIC3, and 1 patient had a MYO5B PFIC variant.

TABLE 3

Patient Demographics and Baseline Characteristics

| | PEDFIC 1 Baseline | | PEDFIC 2 Baseline | | |
|---|---|---|---|---|---|
| | P1O n = 42 | P1P n = 20 | P1O n = 34 | P1P n = 19 | Cohort 2 n = 16 |
| Age, mean (SD), years[a] | 4.5 (3.9) | 3.8 (3.9) | 4.6 (3.6) | 4.3 (4.0) | 7.9 (5.9) |
| Female, n (%) | 23 (54.8) | 8 (40.0) | 18 (52.9) | 7 (36.8) | 9 (56.3) |
| Race, n (%) | | | | | |
| White | 35 (83.3) | 17 (85.0) | 29 (85.3) | 16 (84.2) | 15 (93.8) |
| Black | 2 (4.8) | 0 | 1 (2.9) | 0 | 0 |
| Asian | 1 (2.4) | 1 (5.0) | 1 (2.9) | 1 (5.3) | 0 |
| Other | 0 | 0 | 3 (8.8) | 2 (10.5) | 1 (6.3) |
| Height, mean (SD), cm | 95.1 (21.3) | 89.0 (24.4) | 96.6 (19.0) | 92.6 (23.6) | 115.1 (24.6) |
| Weight, mean (SD), kg | 16.4 (9.6) | 14.5 (9.8) | 16.6 (8.3) | 15.9 (11.2) | 25.2 (16.2) |

TABLE 3-continued

Patient Demographics and Baseline Characteristics

| | PEDFIC 1 Baseline | | PEDFIC 2 Baseline | | |
|---|---|---|---|---|---|
| | P1O<br>n = 42 | P1P<br>n = 20 | P1O<br>n = 34 | P1P<br>n = 19 | Cohort 2<br>n = 16 |
| PFIC type, n (%) | | | | | |
| PFIC1 | 12 (28.6) | 5 (25.0) | 10 (30.3) | 5 (26.3) | 3 (18.8) |
| PFIC2 | 30 (71.4) | 15 (75.0) | 24 (70.6) | 14 (73.7) | 7 (43.8) |
| PFIC3 | — | — | — | — | 5 (31.3) |
| Other[b] | — | — | — | — | 1 (6.3) |
| Use of UDCA at baseline, n (%) | 32 (76.2) | 18 (90) | 23 (67.6) | 17 (89.5) | 13 (81.3) |
| Use of rifampicin at baseline, n (%) | 24 (57.1) | 17 (85.0) | 15 (44.1) | 17 (89.5) | 7 (43.8) |
| Serum bile acids, mean (range), μmol/L | 252.1 (36-605) | 247.5 (56.5-435) | 127.4 (1-439) | 270.8 (11-528) | 221.5 (10.5-465) |
| Pruritus score[c], mean (range) | 2.9 (2-4) | 3.0 (2-4) | 2.0 (0-4) | 2.7 (1.3-4) | 2.9 (2-4) |
| Serum ALT, mean (range), U/L | 110.2 (16.0-798.0) | 76.9 (19.0-236.0) | 73.9 (9.0-352.0) | 71.3 (14.0-193.0) | 69.8 (14.0-231.0) |
| Serum AST, mean (range), U/L | 106.0 (37-405) | 90.2 (32-219) | 98.4 (37-320) | 82.1 (17-210) | 96.6 (31-251) |
| Total bilirubin, mean (range), mg/dL | 3.2 (0.2-18.6) | 3.1 (0.3-11.4) | 1.7 (0.1-12.3) | 3.1 (0.2-19.8) | 2.5 (0.7-7.0) |
| APRI, mean (SE) | 0.6 (0.1) | 0.5 (0.1) | 0.5 (0.1) | 0.5 (0.1) | 1.0 (0.3) |
| PELD/MELD, mean (SE) | −1.5 (1.2) | −0.8 (1.7) | −4.0 (1.3) | −1.5 (1.9) | 0.4 (1.7) |

[a]Data at PEDFIC 1 baseline are for all patients in PEDFIC 1;
[b]For patients from France and Germany, only birth year is collected on the case report form, and age is calculated based on collected age months and years from the external file;
[c]MYO5B deficiency;
[d]AM and PM scores.
ALT, alanine aminotransferase; APRI, aspartate aminotransferase-to-platelet ratio index; AST, aspartate aminotransferase; cohort 2, newly enrolled patients in PEDFIC 2; P1O, PEDFIC 2 participants who received odevixibat (combined 120 and 40 μg/kg/day dose groups) in the preceding PEDFIC 1 study; P1P, PEDFIC 2 participants who received placebo in the preceding PEDFIC 1 study; PELD/MELD, pediatric end-stage liver disease/model for end-stage liver disease; UDCA, ursodeoxycholic acid.

Figure 10:
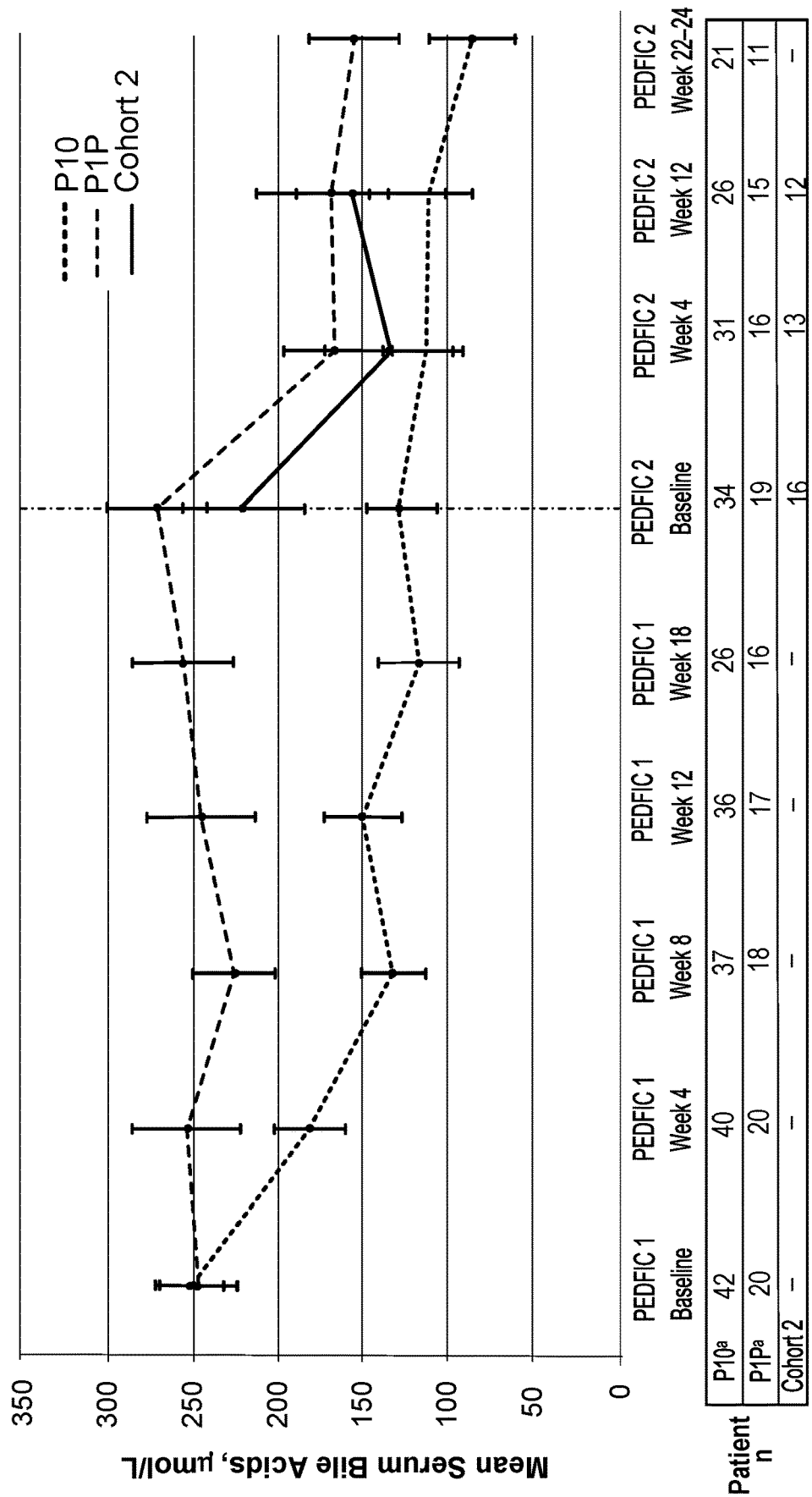
FIG. 10 is a line graph showing the change in serum bile acids during PEDFIC1 and through PEDFIC2 week 24. [a]Values shown for PEDFIC 1 timepoints represent all patients from PEDFIC1 (treated with odevixibat in PEDFIC 1, n=42; treated with placebo in PEDFIC1, n=20); values shown for PEDFIC 2 timepoints represent only the patients in PEDFIC2 (P1O, n=34; P1P, n=19; cohort 2, n=16). [b]Data not shown for n≤10. Cohort 2, newly enrolled patients in PEDFIC2; P1O, PEDFIC2 participants who received odevixibat (combined 120 and 40 μg/kg/day dose groups) in the preceding PEDFIC1 study; P1P, PEDFIC2 participants who received placebo in the preceding PEDFIC1 study.
Figure 11:
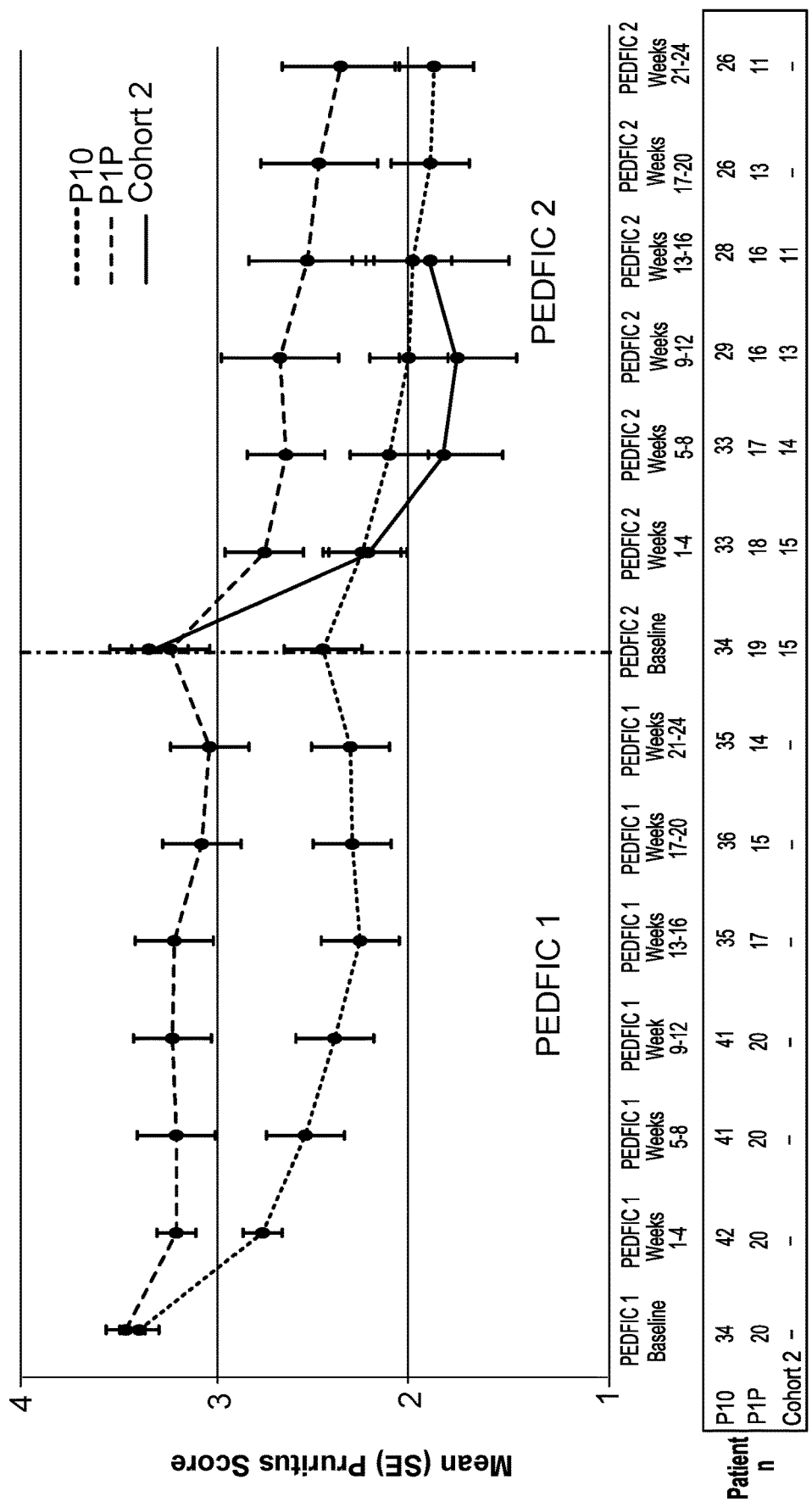
FIG. 11 is a line graph showing the change in pruritus score during PEDFIC1 and through PEDFIC2 week 24. [a]Values shown for PEDFIC1 timepoints represent all patients from PEDFIC1 (treated with odevixibat in PEDFIC1, n=42; treated with placebo in PEDFIC1, n=20); values shown for PEDFIC2 timepoints represent only the patients in PEDFIC2 (P1O, n=34; P1P, n=19; cohort 2, n=16). [b]Data not shown for n≤10. Cohort 2, newly enrolled patients in PEDFIC2; P1O, PEDFIC2 participants who received odevixibat (combined 120 and 40 μg/kg/day dose groups) in the preceding PEDFIC1 study; P1P, PEDFIC2 participants who received placebo in the preceding PEDFIC1 study.

Efficacy
Serum Bile Acids
  In the P1O group across the time period from PEDFIC1 baseline to PEDFIC2 week 24, which represents ~48 weeks of cumulative odevixibat exposure in most of these patients, mean sBAs fell from 251.8 μmol/L to 85.1 μmol/L (P<0.0001; FIG. 10).
  Over the course of PEDFIC2, reductions in sBAs were also observed in the P1P group (270.8 μmol/L to 155.6 μmol/L; FIG. 10).
  For patients in cohort 2, mean sBAs changed from a baseline value of 221.5 to 157.0 at week 12 of PEDFIC 2 (where data were available for ≥10 patients), a change of −73.1 μmol/L (FIG. 10).
Pruritus
  Across the time period from PEDFIC1 baseline to PEDFIC2 week 24, mean monthly pruritus scores dropped from 3.0 to 1.4 (P<0.0001) in the P1O group.
  FIG. 11 shows that pruritus scores improved with odevixibat exposure in all groups.
  By week 24 in PEDFIC2, nearly all P1O sBA responders were also pruritus responders (Table 4)

TABLE 4

Bile Acid and Pruritus Responders Among P1O Patients During PEDFIC 1 and Through PEDFIC 2 Week 24

| Population,<br>n (%) | Bile Acid<br>Responders[a] | Pruritus<br>Responders[b] | Bile Acid or<br>Pruritus<br>Responders | Both Bile Acid<br>and Pruritus<br>Responders[c] |
|---|---|---|---|---|
| PFIC1 | 3/12 (25.0) | 7/12 (58.3) | 7/12 (58.3) | 3/12 (25.0) |
| PFIC2[c] | 15/28 (53.6) | 20/30 (66.7) | 21/30 (70.0) | 14/28 (50.0) |

[a]Defined as a serum bile acid level of ≤65 or ≤102 μmol/L for patients with PFIC1 or PFIC2, respectively.
[b]Defined as ≥1-point drop on pruritus assessment.
P1O, PEDFIC 2 participants who received odevixibat (combined 120 and 40 μg/kg/day dose groups) in the preceding PEDFIC 1 study; PFIC, progressive familial intrahepatic cholestasis.

Growth
  Mean height Z scores improved from −1.6 to −0.5 for P1O from PEDFIC1 baseline through week 24 of PEDFIC2; similarly, those who were odevixibat naive at PEDFIC 2 baseline also experienced improvements in height Z score with odevixibat in PEDFIC 2 (FIG. 12(A)).
  Mean weight Z scores in P1O normalized over 48 weeks (−0.9 to 0.2); weight improvements were also observed for those in the P1P and cohort 2 groups over time following odevixibat initiation (FIG. 12(B)).
Subgroup Analysis
  Similar changes were observed across PFIC subtypes.
    Patients who were odevixibat naive at PEDFIC 2 baseline had mean reductions in sBAs through PEDFIC 2 week 12 regardless of PFIC diagnosis (mean change from baseline: −31.7 [n=5], −120.8 [n=17], and −107.5 [n=3] for those with PFIC1, 2, and 3, respectively)
Additional Outcomes
  There were 2 patients (3%), both in the P1P group, who underwent surgical biliary diversion or had a liver transplant from the period spanning PEDFIC 1 baseline through week 24 of PEDFIC 2
  Patients experienced improvements in several sleep parameters over the course of the study (data not shown).
  Other effects on markers of cholestasis and liver disease are depicted in Table 5.

TABLE 5

Effects of Odevixibat on Markers of Cholestasis and Liver Disease Through Week 24 of PEDFIC 2

| | P1O | | P1P | | Cohort 2 | |
|---|---|---|---|---|---|---|
| | n | Mean Change From Baseline (SE) | n | Mean Change From Baseline (SE) | n | Mean Change From Baseline (SE) |
| Serum ALT, mean (SE), U/L | 21 | −26.9 (22.6) | 9 | 16.3 (20.7) | 4 | −9.8 (31.1) |
| Serum AST, mean (SE), U/L | 20 | −14.6 (10.0) | 9 | −1.7 (5.6) | 4 | −7.8 (16.2) |
| Total bilirubin, mean (SE), mg/dL | 21 | −0.2 (0.1) | 9 | −1.6 (1.3) | 4 | −0.2 (0.5) |
| APRI, mean (SE) | 18 | −0.0 (0.1) | 9 | 0.1 (0.1) | 4 | 0.1 (0.2) |
| PELD/MELD, mean (SE) | 17 | −0.2 (0.3) | 9 | −1.4 (1.2) | 2 | 1.7 (5.8) |

ALT, alanine aminotransferase; APRI, aspartate aminotransferase-to-platelet ratio index; AST, aspartate aminotransferase; Cohort 2, newly enrolled patients in PEDFIC 2; P1O, PEDFIC 2 participants who received odevixibat (combined 120 and 40 µg/kg/day dose groups) in the preceding PEDFIC 1 study; NA, not available in ≥10 patients; P1P, PEDFIC 2 participants who received placebo in the preceding PEDFIC 1 study; PELD/MELD, pediatric end-stage liver disease/model for end-stage liver disease.

Safety

Odevixibat was generally well tolerated through week 24 of PEDFIC 2 (Table 6).
  Incidence of diarrhea was low (occurring in 7 patients [10.1%] overall).
  Treatment-emergent AEs (TEAEs) were mostly mild or moderate; of 50 patients overall with any TEAE, 45 reported mild/moderate TEAEs.
  The rate of discontinuations due to TEAEs was low (<3%).
Additionally, no deaths or drug-related serious TEAEs occurred.

TABLE 6

Summary of TEAEs During the PEDFIC 2 Treatment Period

| Patients, n (%) | P1O n = 34 | P1P n = 19 | Cohort 2 n = 16 |
|---|---|---|---|
| Any TEAE | 28 (82.4) | 14 (73.7) | 8 (50.0) |
| Mild | 17 (50.0) | 6 (31.6) | 2 (12.5) |
| Moderate | 10 (29.4) | 7 (36.8) | 3 (18.8) |
| Severe | 1 (2.9) | 1 (5.3) | 3 (18.8) |
| Drug-related TEAEs | 10 (29.4) | 5 (26.3) | 5 (31.3) |
| Serious TEAEs | 0 | 3 (15.8) | 1 (6.3) |
| TEAEs leading to discontinuation | 0 | 1 (5.3) | 2 (12.5) |
| Drug-related TEAEs occurring in 6 or more patients overall, by preferred term (listed in alphabetical order) | | | |
| Blood bilirubin increased | 4 (11.8) | 2 (10.5) | 3 (18.8) |
| Cough | 8 (23.5) | 2 (10.5) | 0 |
| Diarrhea | 6 (17.6) | 1 (5.3) | 0 |
| INR increased | 2 (5.9) | 2 (10.5) | 2 (12.5) |
| Pruritus | 4 (11.8) | 2 (10.5) | 0 |
| Pyrexia | 7 (20.6) | 4 (21.1) | 2 (12.5) |
| URTI | 9 (26.5) | 5 (26.3) | 0 |

AE, adverse event; ALT, alanine aminotransferase; cohort 2, newly enrolled patients in PEDFIC2; INR, international normalized ratio; P1O, PEDFIC2 participants who received odevixibat (combined 120 and 40 µg/kg/day dose groups) in the preceding PEDFIC1 study; P1P, PEDFIC2 participants who received placebo in the preceding PEDFIC1 study; TEAE, treatment-emergent adverse event; URTI, upper respiratory tract infection.

No clinically significant changes or safety signals were noted in mean serum chemistry, hematology, urinalysis, or international normalized ratio values based on laboratory assessments
There were no new or worsening fat-soluble vitamin deficiencies that were refractory to clinically recommended vitamin supplementation

CONCLUSIONS

Data from this ongoing, long-term study demonstrate the continued effect of odevixibat treatment for up to 48 weeks on key parameters including sBAs, pruritus, growth, and hepatic parameters.
  Long-term odevixibat treatment improved aspects of cholestasis in patients with PFIC (eg, reduced sBAs, serum ALT, and total bilirubin).
Importantly, average sBAs in patients treated for 48 weeks fell below the published threshold for PFIC2 disease modification (van Wessel D B E, et al. *J Hepatol.* 2020; 73:84-93).
In addition, efficacy was observed across all PFIC subtypes studied, and odevixibat had a favorable safety profile.
Overall, odevixibat has the potential to provide long-term treatment benefits in patients with PFIC.

REFERENCES

1. Bull L N, Thompson R J. *Clin Liver Dis.* 2018; 22:657-69.
2. Baker A, et al. *Clin Res Hepatol Gastroenterol.* 2019; 43:20-36.
3. European Association for the Study of the Liver. *J Hepatol.* 2009; 51:237-67.
4. Kamath B M, et al. *Liver Int.* 2020; 40:1812-22.
5. Gillberg P G, et al. *J Pediatr Gastroenterol Nutr.* 2019; 69(suppl 2):5113.
6. Sturm et al. *Hepatology.* 66(suppl 1):646A-7A.
7. van Wessel D B E, et al. *J Hepatol.* 2020; 73:84-93.

Example 3—Preparation of the Formulation (Small Scale)

Microcrystalline cellulose spheres were coated with one of two different coating suspensions of odevixibat, as indicated in Table 7 below, to obtain particles containing either 0.5% w/w or 1.5% w/w odevixibat.

TABLE 7

| Ingredient | Amount (g/batch) | Amount (g/batch) |
|---|---|---|
| Core: | | |
| Microcrystalline cellulose spheres 700 (Vivapur ® MCC sphere 700) | 1500 | 1500 |
| Coating: | 7.5 | 22.5 |
| Odevixibat | 30.0 | 90.0 |
| Hypromellose 3 mPa · s (Methocel ® E3 premium) | | |
| Purified water[a] | 337.5 | 1012.5 |
| Total (coated particles) | 1537.5 | 1612.5 |

[a] Purified water is removed during the coating and drying process.

Crystalline odevixibat was used. Typical values for the particle size distribution of the crystalline material were $d_{10}=0.9$ μm, $d_{50}=4$ μm and $d_{90}=20$ μm, wherein $d_{10}$, $d_{50}$ and $d_{90}$ are defined as the diameters where 10%, 50% and 90%, respectively, of the particle population lies below these values.

Coating Suspension

The coating suspension containing odevixibat drug substance was prepared in three steps:
a) Odevixibat suspension: odevixibat drug substance was sieved through a 0.5 mm sieve, followed by wetting in a small amount of the water using a homogenizer (Ultra Turrax T25; 15 minutes at approximately 6600-7000 rpm). The resulting wetted odevixibat drug substance was then dispersed in water by means of a colloid mill (IKA Magic Lab MKO or MK modules, 14600 rpm for 20 minutes, gap size 1.5 rotation) until the level of agglomerates met the in-process control acceptance limits.
b) Hypromellose dispersion: Hypromellose (3 mPa·s) was dispersed in hot water with mixing, and the resultant dispersion was cooled to room temperature.
c) Odevixibat coating suspension: The hypromellose dispersion was added to the odevixibat suspension in the colloid mill and the suspension was mixed for 4 minutes at 10000 rpm. Final mixing was continued at low speed using a magnetic stirrer. The odevixibat coating suspension was filtered through a 0.5 mm sieve before use in the coating process.

The dispersion of odevixibat in the coating suspension was monitored by optical microscopy, using a method based on European Pharmacopoeia 9.0, monograph 2.9.37, which was adjusted to be applicable for the odevixibat coating suspension. A Leica DMLB microscope equipped with a Leica DMC 2900 digital camera was used, and an objective with 10× magnification.

Samples were prepared by placing a small droplet of the coating suspension (using a Pasteur pipette) on a blank objective glass on top of a grid counting chamber of 4×4 test fields. A cover glass (about 18×18 mm, the same size as the grid) was placed on the droplet and slightly pressed on the centre to get a thin, even sample. The diameter of the sample was comparable with the size of the cover glass.

The objective was set with magnification ×10 and the scale bar was adjusted to 100 μm. Five replicates were scanned. The size of any agglomerates was checked by comparing them against the scale bar in four predetermined test fields for each replicate. The total number of agglomerates was calculated from 5 replicates×4 test fields, i.e. in total 20 test fields. The coating suspension was accepted if the 20 test fields did not contain more than 5 agglomerates ≥50 μm, and no agglomerates ≥200 μm.

Coating Process

Microcrystalline cellulose (MCC) spheres were coated using the odevixibat coating suspension in a fluid bed coater with Wurster insert. The amount of coating suspension on the MCC spheres is determined by weighing. The coated particles were sieved through a 0.5 mm and 1.25 mm sieve, respectively, in order to remove fine particles as well as twins. The particles were then transferred to bulk containers and handled as a drug product intermediate.

Capsule Filling

The calculated amount of particles required for each unit dose were filled into hard hydroxypropyl methylcellulose (HPMC) capsules (Size 0 or Size 3) using an automatic capsule filler, to provide four different strengths: 200, 400, 600 and 1200 μg.

The 200 and 600 μg strengths are Size 0 white capsules containing 40 mg of particles having an odevixibat concentration of 0.5% w/w and 1.5% w/w, respectively. These strengths will be used for patients with a weight range of 5.0 kg to <19.5 kg in the low- (40 μg/kg) and high- (120 μg/kg) dose groups of the Phase 3 clinical studies. The Size 0 capsules are designed to be opened so that the contents can be sprinkled onto a food vehicle for administration. They are not intended to be swallowed intact.

The 400 μg and 1200 μg strengths are Size 3 white capsules containing 80 mg of particles having an odevixibat concentration of 0.5% w/w and 1.5% w/w, respectively. These strengths will be used for patients with a weight range of 19.5 kg to >55.5 kg in the low- (40 μg/kg) and high- (120 μg/kg) dose groups of the Phase 3 clinical studies. The Size 3 capsules are intended to be swallowed intact.

The fill weight, the amounts of odevixibat and other ingredients and the capsule size for the different capsule strengths are shown in Table 8 below.

TABLE 8

| | Strength | | | |
|---|---|---|---|---|
| COMPONENT | 200 μg | 400 μg | 600 μg | 1200 μg |
| odevixibat concentration of particles | 0.5% w/w | | 1.5% w/w | |
| Fill weight (mg) (theoretical) | 40 | 80 | 40 | 80 |
| Particles | | | | |
| Microcrystalline cellulose spheres 700 (Vivapur ® MCC sphere 700) | 39 | 78 | 37 | 74 |

TABLE 8-continued

|  | Strength | | | |
| --- | --- | --- | --- | --- |
| Odevixibat | 0.200 | 0.400 | 0.600 | 1.200 |
| Hypromellose 3 mPa · s (Methocel ® E3 Premium) | 0.8 | 1.6 | 2.4 | 4.8 |
| Capsule | | | | |
| Hypromellose capsule, white (Vcaps ® Plus) | Size 0 | Size 3 | Size 0 | Size 3 |

Example 4—Preparation of the Formulation (Larger Scale)

Microcrystalline cellulose spheres were coated with one of two different coating suspensions of odevixibat, as indicated in Table 9 below, to obtain particles containing either 0.5% w/w or 1.5% w/w odevixibat.

TABLE 9

| Ingredient | Amount (kg/batch) | Amount (kg/batch) |
| --- | --- | --- |
| Core: | | |
| Microcrystalline cellulose spheres 700 (Vivapur ® MCC sphere 700) | 14.625 | 13.875 |
| Coating: | | |
| Odevixibat | 0.075 | 0.225 |
| Hypromellose 3 mPa · s (Methocel ® E3 premium) | 0.300 | 0.900 |
| Purified water[a] | 3.375 | 10.125 |
| Total (coated particles) | 15.000 | 15.000 |

[a]Purified water is removed during the coating and drying process.

Crystalline odevixibat was used. Typical values for the particle size distribution of the crystalline material were $d_{10}$=0.9 μm, $d_{50}$=4 μm and $d_{90}$=20 μm, wherein $d_{10}$, $d_{50}$ and $d_{90}$ are defined as the diameters where 10%, 50% and 90%, respectively, of the particle population lies below these values.

Coating Suspension

The coating suspension containing odevixibat drug substance was prepared in three steps:
  a) odevixibat suspension: odevixibat drug substance was wetted in a small amount of the water using a homogenizer (Ultra Turrax T25; 15 minutes at approximately 6600-7000 rpm). The resulting wetted odevixibat drug substance was then dispersed in water by means of a colloid mill (IKA Magic Lab MKO or MK modules, 14600 rpm for 20 minutes, gap size 1.5 rotation) until the level of agglomerates met the in-process control acceptance limits, i.e. $d_{90}$<12 μm (as determined by low-angle laser light scattering (LALLS)).
  b) hypromellose dispersion: Hypromellose (3 mPa·s) was dispersed in hot water with mixing, and the resultant dispersion was cooled to room temperature.
  c) odevixibat coating suspension: The hypromellose dispersion was added to the odevixibat suspension and the suspension was mixed. Final mixing was continued at low speed using a stirrer. The odevixibat coating suspension was filtered through a 0.5 mm sieve before use in the coating process.

Coating Process

The obtained odevixibat coating suspension was used for coating microcrystalline cellulose (MCC) spheres in accordance with the coating process described in Example 1.

Capsule Filling Capsules were prepared in accordance with Example 1. The fill weight, the amounts of odevixibat and other ingredients and the capsule size for the different capsule strengths were as presented in Table 5 above.

Example 5—Preparation of Crystal Modification 1

Absolute alcohol (100.42 kg) and crude odevixibat (18.16 kg) were charged to a 250-L GLR with stirring under nitrogen atmosphere. Purified water (12.71 kg) was added and the reaction mass was stirred under nitrogen atmosphere at 25±5° C. for 15 minutes. Stirring was continued at 25±5° C. for 3 to 60 minutes, until a clear solution had formed. The solution was filtered through a 5.0μ SS cartridge filter, followed by a 0.2μ PP cartridge filter and then transferred to a clean reactor. Purified water (63.56 kg) was added slowly over a period of 2 to 3 hours at 25±5° C., and the solution was seeded with crystal modification 1 of odevixibat. The solution was stirred at 25±5° C. for 12 hours. During this time, the solution turned turbid. The precipitated solids were filtered through centrifuge and the material was spin dried for 30 minutes. The material was thereafter vacuum dried in a Nutsche filter for 12 hours. The material was then dried in a vacuum tray drier at 25±5° C. under vacuum (550 mm Hg) for 10 hours and then at 30±5° C. under vacuum (550 mm Hg) for 16 hours. The material was isolated as an off-white crystalline solid. The isolated crystalline material was milled and stored in LDPE bags.

An overhydrated sample was analyzed with XRPD and the diffractogram is shown in FIG. 2 of WO 2019/245449. Another sample was dried at 50° C. in vacuum and thereafter analyzed with XRPD. The diffractogram of the dried sample is shown in FIG. 1 of v.

The diffractograms for the drying of the sample are shown in FIGS. 3 and 4 of WO 2019/245449 for 20 ranges 5-13° and 18-25°, respectively (overhydrated sample at the bottom and dry sample at the top).

Example 6—Preparation of Crystal Modification 2 from Ethanol and Water 105.9 mg of odevixibat were weighed into a 1 mL Chromacol vessel. A magnetic stir bar and 1.0 mL of an ethanol:water 70:30% v/v mixture were added and the vessel was closed with a crimped cap. The resulting slurry was then left stirred at 25° C. for 1 week.

The wet sample was analyzed with XRPD and the diffractogram is shown in FIG. 5 of WO 2019/245449. Upon drying of the sample, it transformed into crystal modification 1.

Abbreviations
DMF dimethylformamide
DMSO dimethyl sulfoxide
EtOH ethanol
MeOH methanol RH relative humidity
2-PrOH 2-propanol

EXPERIMENTAL METHODS

X-Ray Powder Diffraction (XRPD) Analysis

Analyses were performed at 22° C. on a PANalytical X'Pert Pro diffractometer equipped with a Cu long fine focus X-ray tube and a PIXcel detector. Automatic divergence and anti-scatter slits were used together with 0.02 rad Soller slits and a Ni-filter. Dry samples were smeared onto cut Silicon Zero Background Holders (ZBH) and analysed between 2-40° in 2-theta with an analysis time of 17 minutes. All slurry samples were dripped on tempered porous Alumina filter substrates and analysed twice as they dried, first with a one minute 16-second scan (2-30° in 2-theta) and then a 7-minute scan (2-30° in 2-theta). A final 17-minute scan was performed when the sample had dried for several hours.

The samples were spun during analysis in order to increase the randomness of the samples. The following experimental settings were used:
Tube tension and current: 40 kV, 50 mA
Wavelength alpha1 (CuKα1): 1.5406 Å
Wavelength alpha2 (CuKα2): 1.5444 Å
Wavelength alpha1 and alpha2 mean (CuKα): 1.5418 Å

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realise that the relative intensities of peaks may vary according to the orientation of the sample under the test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry," John Wiley & Sons, 1996).

Differential Scanning calorimetry (DSC)

Experiments were performed using a TA Instruments Q2000 Differential Scanning calorimeter. The DCS crucible used was a TZero aluminum pan with pinhole (diameter ≥0.2 mm) in the lid. A dry nitrogen purge at a constant flow rate of 50 mL/min was maintained in the DSC cell throughout the measurement.

Example 7—Pooled Analysis of Data from the Phase 3 PEDFIC 1 (P1; NCT03566238) and PEDFIC 2 (P2; NCT03659916) Studies This example describes key outcomes with odevixibat in children with PFIC1 (familial intrahepatic cholestasis 1 [FIC1] deficiency) or PFIC2 ((bile salt export pump [BSEP] deficiency) based on pooled analysis of data from the phase 3 PEDFIC 1 (P1; NCT03566238) and PEDFIC 2 (P2; NCT03659916) studies. This pooled analysis covers up to 48 weeks of odevixibat treatment from P1 and through the planned P2 interim data cut. The following outcomes are described: change in serum bile acids (sBAs), change in pruritus score (measured using the PRUCISION scale; range: 0-4), evaluation of growth and sleep parameters, and safety monitoring. Mean changes in autotaxin (linked to cholestatic pruritus intensity) and plasma 7α-hydroxy-4-cholesten-3-one (p-C4; marker of bile acid synthesis) levels were also summarized.

Across the P1 and P2 studies, 77 patients received odevixibat. This included 19 who received oral placebo in P1 and rolled into P2, 42 who received odevixibat in P1 (of these, 34 rolled into P2), and 16 newly enrolled patients in P2. At baseline, mean sBAs and pruritus scores were 250 μmol/L (n=77) and 2.9 (n=76), respectively. Four weeks after starting odevixibat, the mean decrease in sBAs was −88 μmol/L (n=68); over the first 4-week period, the mean change in pruritus score was −0.7 (n=75). At the end of the analysis period, mean change from baseline in sBAs was −213 μmol/L in patients with available data (n=24); mean change in pruritus score was −1.4 (n=32). Mean height Z scores improved from −1.9 at baseline (n=75) to −0.8 at week 48 (n=20), a mean change of 0.5. Similar improvements were observed for mean weight Z scores (baseline: −1.1 [n=75]; week 48: −0.0 [n=21]). Odevixibat-treated patients had mean changes from baseline to weeks 37-48 in observer-reported percentage of days seeing blood due to scratching [−25%], needing help falling asleep [−52%], needing soothing [−51%], and sleeping with caregiver [−40%]). Overall, drug-related treatment-emergent adverse events (TEAEs) were reported in 32 of 77 (42%) patients, but no drug-related serious TEAEs were reported. Four patients had TEAEs leading to treatment discontinuation.

Figure 13A:
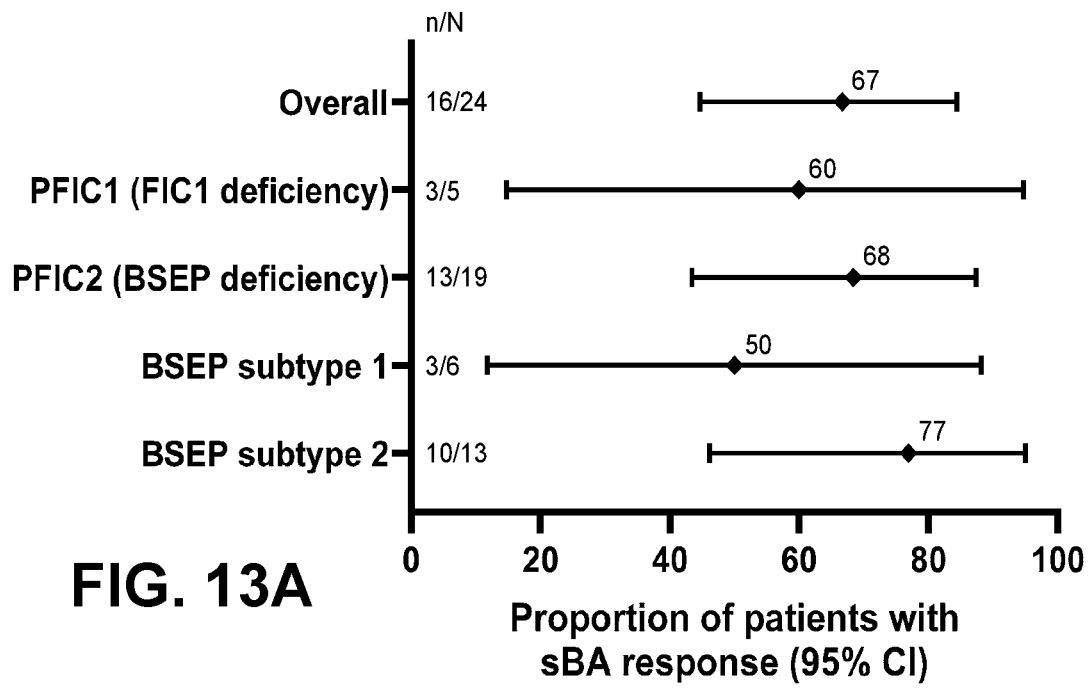
FIG. 13A shows the proportion of patients with a serum bile acid response (95% CI) in different PFIC subgroups.
Figure 13B:
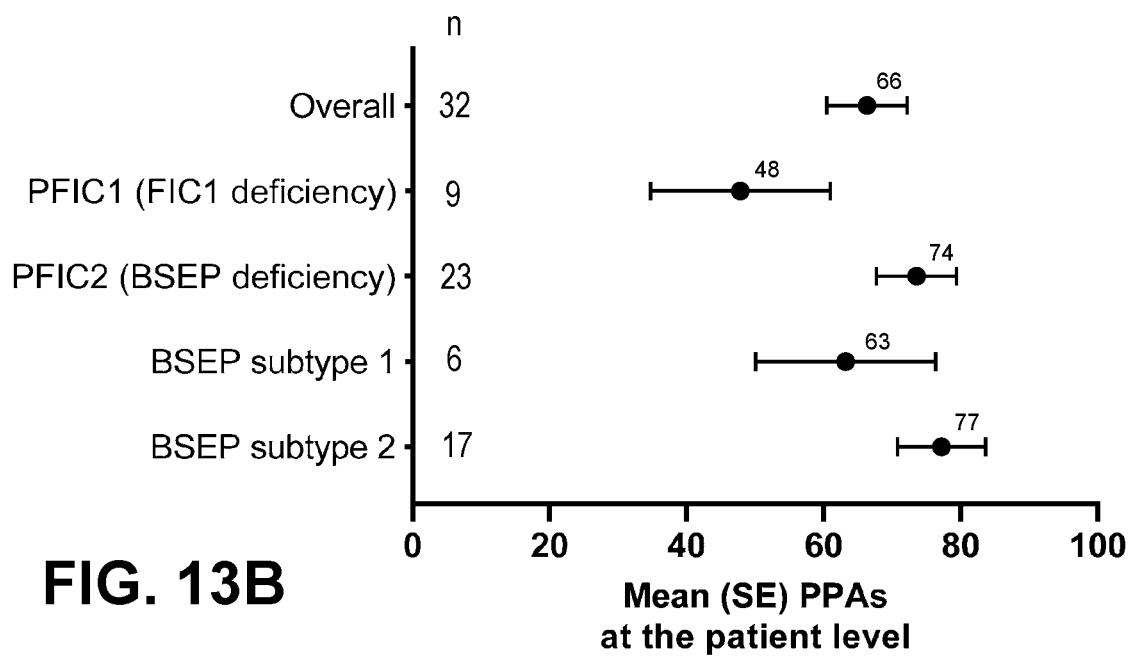
FIG. 13B shows the mean (SE) of positive pruritus assessments at the patient level in different PFIC subgroups.
Figures 14A, 14B:
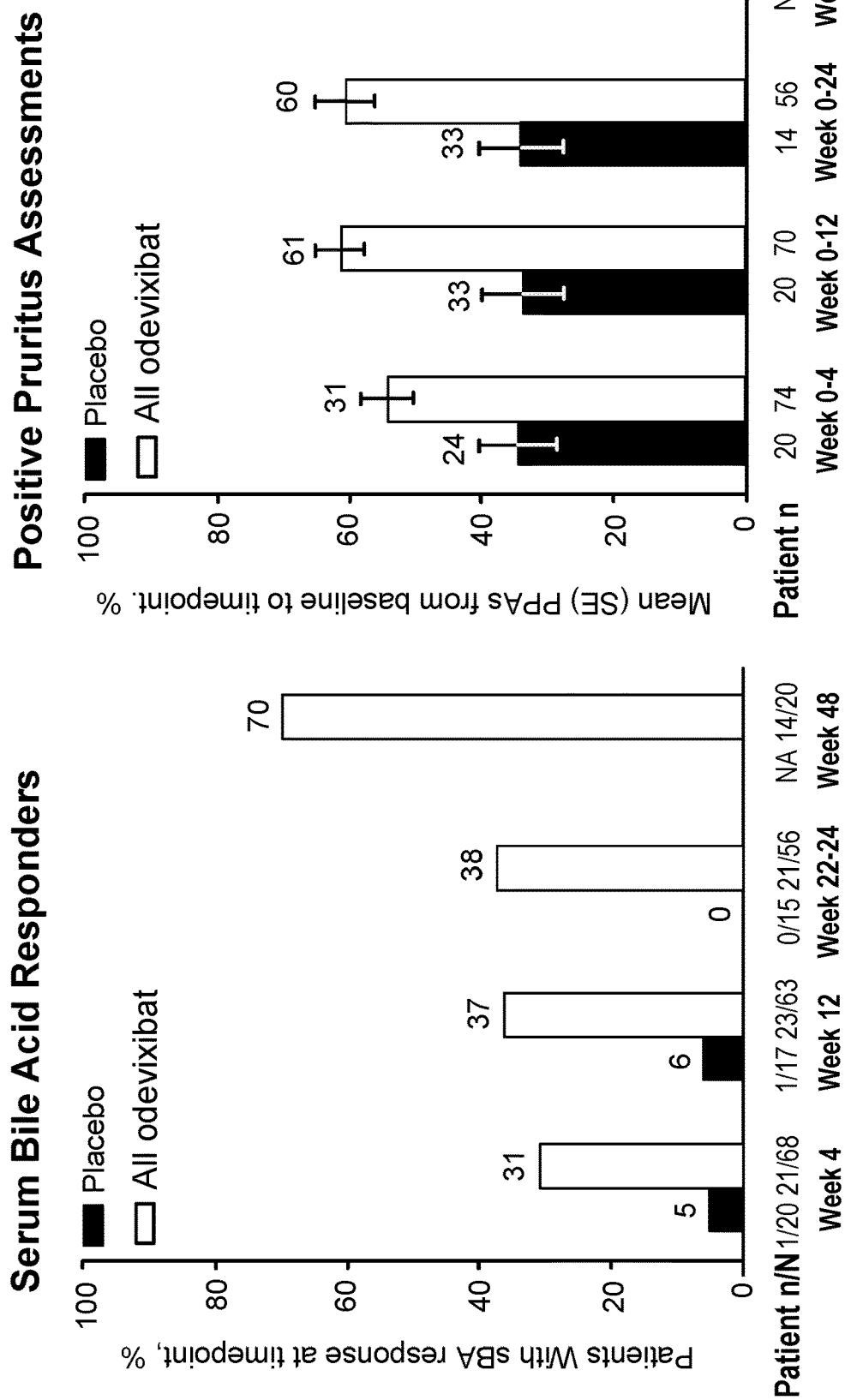

Of the 77 patients who received odevixibat, 20 had PFIC1 (26%), 51 (66%) had PFIC2, 5 had PFIC3 (7%), and 1 had MYO5B (1%). BSEP subtype 1 or 2 were present in 13 (26%) and 36 (71%) patients with PFIC2, respectively (2 additional patients with BSEP subtype 3 were not included in this analysis). During the analysis period, ≥50% of patients met sBA response criteria, regardless of genotype (FIG. 13A). Mean PPAs were above 60% for patients with PFIC2 (including BSEP subtypes 1 and 2); mean PPAs for patients with PFIC1 were 48% (FIG. 13 B). Incidence of TEAEs in odevixibat-treated patients with PFIC1 or PFIC2 (80% each) and BSEP subtype 1 and 2 (77% and 86%, respectively) in the pooled population was comparable to that of placebo-treated patients in P1 (85%). Most TEAEs were mild or moderate, self-limiting, and considered by the investigator as not related to study drug. Patients with PFIC1 or PFIC2 had substantial benefits with odevixibat treatment, including reductions in sBAs and improvement in pruritus symptoms. Long-term treatment with odevixibat was well tolerated, regardless of PFIC classification or BSEP subtype.

FIG. 14A-14D show that treatment with odevixibat was associated with rapid improvement in sBAs, pruritus, autotaxin, and p-C4 levels (i.e., by week 1-4), with clinical benefits sustained through 48 weeks of treatment. Overall, 61 of 77 patients (79%) experienced any TEAE, incidence comparable to that in patients treated with placebo in P1 ($^{17}/_{20}$ [85%]). Eight patients reported severe TEAEs, and none had serious adverse events deemed related to treatment.

Patient sleep was evaluated based on caregiver report using the PRUCISION scale and via the clinician- or caregiver-reported Global Impression of Change (CGIC or CaGIC, respectively) sleep scales. Treatment response was defined as an sBA response (sBAs <65 or <102 μmol/L for patients with PFIC1 and PFIC2, respectively) or a pruritus response (a ≥1-point drop from baseline in pruritus score).

Mean decreases in caregiver-reported percentage of days with scratching associated with bleeding, needing help falling asleep, and needing soothing were greater among Rs vs NRs (Table 10). At week 48, clinicians and caregivers reported that ≥88% of Rs had moderately or very much better sleep since starting odevixibat (Table 10).

TABLE 10

|  | sBA or Pruritus Response | | | |
|---|---|---|---|---|
|  | Yes (n = 48) | | No (n = 28) | |
| Change from baseline to weeks: | n | Mean | n | Mean |
| % Days with scratching associated with bleeding | | | | |
| 1-4 | 47 | −16.8 | 28 | −6.5 |
| 21-24 | 34 | −30.9 | 22 | 3.2 |
| 45-48 | 18 | −41.5 | 2 | 12.5 |
| % Days needing help falling asleep | | | | |
| 1-4 | 47 | −23.1 | 28 | −10.4 |
| 21-24 | 34 | −56.1 | 22 | −4.9 |
| 45-48 | 18 | −73.0 | 2 | −1.8 |
| % Days needing soothing | | | | |
| 1-4 | 47 | −22.5 | 28 | −6.0 |
| 21-24 | 34 | −58.8 | 22 | 7.8 |
| 45-48 | 18 | −74.6 | 2 | 4.2 |
| % days sleeping with caregiver | | | | |
| 1-4 | 47 | −23.1 | 28 | −3.1 |
| 21-24 | 34 | −48.5 | 22 | 3.1 |
| 45-48 | 18 | −69.1 | 2 | 0.0 |
| Number of awakenings | | | | |
| 1-4 | 47 | −3.1 | 28 | 1.3 |
| 21-24 | 34 | −1.9 | 22 | 1.5 |
| 45-48 | 18 | −11.0 | 2 | −4.3 |

TABLE 10-continued

|  | sBA or Pruritus Response | | | |
|---|---|---|---|---|
|  | Yes (n = 48) | | No (n = 28) | |
| Change from baseline to weeks: | n | Mean | n | Mean |
| Value at timepoint: CGIC, moderately or very much better, % | | | | |
| 4 | 42 | 57.1 | 26 | 30.8 |
| 24 | 32 | 59.4 | 21 | 33.3 |
| 48 | 18 | 88.9 | 4 | 25.0 |
| CaGIC, moderately or very much better, % | | | | |
| 4 | 39 | 48.7 | 28 | 25.0 |
| 24 | 27 | 70.4 | 21 | 23.8 |
| 48 | 15 | 93.3 | 3 | 33.3 |

Using pooled data from these studies, changes in parameters of cholestasis, pruritus, and hepatic laboratory markers in patients who responded to odevixibat treatment (Rs) vs treatment nonresponders (NRs). Two responder definitions were examined: 1) sBA response (i.e., sBAs <65 or <102 µmol/L for PFIC1 and PFIC2, respectively) and 2) sBA response or pruritus response (i.e., a ≥1-point drop from baseline in PRUCISION score).

Rates of sBA Rs and sBA or pruritus Rs were 31% and 57%, respectively, at weeks 0-24, 48% and 60% at weeks 25-36, and 59% and 65% at weeks 37-48. Among all odevixibat-treated patients, mean change from baseline (CFB) to week 48 in alanine aminotransferase (ALT) and total bilirubin was −82 U/L and −18 µmol/L, respectively. In general, Rs had greater mean CFB (i.e., improvements) vs NRs in these hepatic laboratory parameters with long-term odevixibat treatment (Table 11A) that started as early as week 4 and increased over time.

TABLE 11A

|  | sBA Response | | | | sBA or Pruritus Response | | | |
|---|---|---|---|---|---|---|---|---|
| Liver Enzyme | Yes | | No | | Yes | | No | |
| Levels | n (%[a]) | Mean (SE) | m | Mean (SE) | n (%[a]) | Mean (SE) | m | Mean (SE) |
| ALT, U/L | | | | | | | | |
| Baseline | 24 (39) | 124 (33) | 38 | 82 (12) | 48 (63) | 104 (18) | 28 | 69 (11) |
| CFB→wk 4 | 23 (39) | −28 (37) | 36 | 21 (16) | 43 (61) | −2 (24) | 27 | 9 (4) |
| CFB→wk 24 | 19 (40) | −67 (42) | 28 | −10 (11) | 31 (62) | −56 (27) | 19 | 5 (8) |
| CFB→wk 48 | 15 (63) | −112 (57) | 9 | −32 (22) | 18 (75) | −108 (48) | 6 | −5 (15) |
| Total bilirubin, µmol/L | | | | | | | | |
| Baseline | 24 (39) | 27 (7) | 38 | 74 (12) | 48 (63) | 42 (6) | 28 | 67 (16) |
| CFB→wk 4 | 23 (39) | −8 (4) | 36 | −10 (9) | 43 (61) | −6 (4) | 27 | −14 (11) |
| CFB→wk 24 | 19 (40) | −23 (8) | 28 | −19 (10) | 31 (62) | −19 (7) | 19 | −23 (13) |
| CFB→wk 48 | 15 (63) | −25 (11) | 9 | −6 (14) | 18 (75) | −25 (9) | 6 | 1 (20) |

[a]Responder rate ([n/(n + m)]*100).

In children with PFIC, odevixibat treatment for up to 48 weeks was well tolerated and associated with clinically meaningful effects on sBAs, pruritus, growth, and sleep parameters. Treatment was associated with rapid control of biochemical and clinical markers of cholestasis, with durable effects over time. Patients who responded to odevixibat treatment had sustained improvements in key clinical signs related to PFIC and hepatic laboratory parameters that were not observed to the same extent in treatment nonresponders. Patients with PFIC and odevixibat treatment response had substantial improvements in caregiver- and clinician-reported sleep. These effects occurred rapidly and continued over time. The improvement in sleep is likely linked to the improved pruritus observed in patients who responded to odevixibat.

Example 8—Pretreatment Serum Bile Acid Parameters and Predictability of Response to Odevixibat, an Ileal Bile Acid Transporter Inhibitor, in Children with PFIC This analysis included children with PFIC aged 0.5-18 years with elevated sBAs and history of significant pruritus who were treated with odevixibat 40 µg/kg/day (n=23) or 120 µg/kg/day (n=19) in PEDFIC 1. Pretreatment sBA composition was analyzed using liquid chromatography-tandem mass spectrometry, quantifying serum concentrations of total BAs and primary (cholate, chenodeoxycholate) and secondary (deoxycholate, lithocholate) BAs. sBA concentrations are presented below including and excluding the contribution from ursodeoxycholate (UDCA). Pretreatment serum concentrations of 7α-hydroxy-4-cholesten-3-one (C4) were also quantified. Pretreatment parameters were analysed in treatment responders (Rs; i.e., patients with sBAs ≤70 µmol/L or reduced ≥70% and/or a ≥1-point drop in observer-reported pruritus score from baseline to end of treatment) vs nonresponders (NRs).

The proportion of Rs was $^{16}/_{23}$ and $^{8}/_{19}$, respectively, in the 40 and 120 µg/kg/day dose groups; groups were combined for analysis (overall Rs, $^{24}/_{42}$ [57%]). Before starting odevixibat, Rs and NRs had comparable mean serum concentrations of total BAs (267.4 and 275.4 µmol/L, respectively), primary BAs (203.0 and 213.6 µmol/L), and secondary BAs (64.5 and 61.8 µmol/L) when the contribution of UDCA was considered. Results were similar for Rs and NRs when the UDCA was excluded (total BAs, 203.6 and 214.2 µmol/L; primary BAs, 203.0 and 213.6 µmol/L; secondary BAs, 0.6 and 0.5 µmol/L). Mean serum C4 concentrations before treatment were 4.8 ng/mL in Rs and 4.5 ng/mL in NRs.

Response to odevixibat treatment in PFIC1 or PFIC2 patients was not associated with pretreatment serum concentrations of total, primary, or secondary BAs or of C4, a marker for BA synthesis rate. Interestingly, the low pretreatment concentrations of secondary BAs, indicators of intestinal metabolism and reabsorption, relative to primary BAs apparently did not preclude subsequent response to odevixibat in these patients.

In another analysis, pretreatment variations in serum bile acids and pruritus were assessed to avoid any potential confounding due to perceived or actual effects during treatment. Standard deviations (SDs) for each patient (i.e., intraindividual variation) for serum bile acid levels and pruritus scores prior to first dose of study drug were summarized, with SDs first calculated across all predose values at the patient level prior to calculation of summary statistics. SD values for serum bile acids are from 2 screening visits, the baseline visit, and any other unscheduled assessments before randomization. The median (range) age of patients at PEDFIC 1 start was 3.2 (0.5-16) years, and half of patients were female. Overall, 17 patients (27%) had PFIC1 and 45 (73%) had PFIC2. All patients had elevated serum bile acids and significant pruritus at baseline, consistent with the PEDFIC 1 study enrollment criteria.

In general, patients with PFIC1 had somewhat less intraindividual variation in pretreatment serum bile acid levels than did patients with PFIC2. Patients with PFIC1 or PFIC2 exhibited a similar extent of intraindividual variation in pretreatment pruritus scores.

Before study start in the overall population, the median (range) of per-patient SDs across all pretreatment measurements was 42 (5-183) µmol/L for serum bile acids and 0.6 (0-1.2) for pruritus scores (Table 11B). These summary data also show that median pretreatment intraindividual variation in serum bile acids was lower in patients with PFIC1 versus patients with PFIC2, whereas median pretreatment intraindividual variation in pruritus scores was similar for patients with PFIC1 or PFIC2 (Table 11B).

TABLE 11B

| | Summary Statistics of Standard Deviation* of Pretreatment Serum Bile Acid Concentrations or Pruritus Scores | | |
|---|---|---|---|
| Summary Measure | Overall, N = 62 | PFIC1, n = 17 | PFIC2, n = 45 |
| Pretreatment Standard Deviation of Serum Bile Acid Concentrations, µmol/L | | | |
| Mean | 58 | 39 | 65 |
| SD | 46 | 27 | 49 |
| Median | 42 | 33 | 53 |
| Range | 5.0, 183 | 5.0, 94 | 6.8, 183 |
| Q1 | 26 | 16 | 27 |
| Q3 | 85 | 50 | 103 |
| Pretreatment Standard Deviation of Pruritus Scores | | | |
| Mean | 0.6 | 0.6 | 0.6 |
| SD | 0.3 | 0.3 | 0.3 |
| Median | 0.6 | 0.6 | 0.7 |

TABLE 11B-continued

Summary Statistics of Standard Deviation* of Pretreatment
Serum Bile Acid Concentrations or Pruritus Scores

| Summary Measure | Overall, N = 62 | PFIC1, n = 17 | PFIC2, n = 45 |
|---|---|---|---|
| Range | 0, 1.2 | 0, 1.2 | 0, 1.1 |
| Q1 | 0.4 | 0.5 | 0.4 |
| Q3 | 0.8 | 0.7 | 0.8 |

*SD was first calculated at a patient level before the summary statistics were calculated.

Prior to the start of PEDFIC1, patients with PFIC1 and PFIC2 had considerable variations in serum bile acids and also had variations in pruritus scores.

Example 9—Improved Quality of Life in Children with PFIC Following 24 Weeks of Treatment with Odevixibat: Results from the Phase 3 PEDFIC 1 Study As described herein, in the randomized, placebo-controlled, phase 3 PEDFIC 1 trial, odevixibat reduced serum bile acids and improved pruritus and several sleep parameters in children with PFIC1 and PFIC2. In the Phase 3 study, both primary endpoints of PEDFIC 1 were met, including least squares mean proportion of positive pruritus assessments (PPAs) was 55.1% with all odevixibat doses vs 30.1% with placebo (P=0.004), and the percentage of serum bile acid responders was 33.3% with all odevixibat doses vs 0% with placebo (P=0.003). In this example, the effect of odevixibat treatment on quality of life (QoL) was assessed as an exploratory outcome in the PEDFIC 1 trial.

Study design and eligibility was as follows. In PEDFIC 1, patients were randomized 1:1:1 to receive oral, once-daily placebo, odevixibat 40 μg/kg/day, or odevixibat 120 μg/kg/day for 24 weeks; patients who completed 24 weeks of treatment could enroll in an open-label extension. Patients between the ages of 6 months and 18 years with a diagnosis of PFIC1 or PFIC2 were eligible for the study if they had elevated serum bile acid levels (defined as ≥100 μmol/L averaged from 2 samples taken prior to randomization, ≥7 days apart) and significant pruritus as reported by caregivers (average score ≥2 on a scale of 0-4 in the 2 weeks prior to randomization using an observer-reported outcome instrument).

For outcomes and assessments, two different primary endpoints were evaluated in PEDFIC 1: proportion of PPAs (defined as a scratching score of ≤1 or at least a 1-point reduction from baseline, using the observer-reported outcome instrument) over 24 weeks and proportion of patients with a serum bile acid response (defined as a ≥70% reduction from baseline in fasting serum bile acids or a serum bile acid level ≤70 μmol/L) at week 24.

A change from baseline to week 24 for the Pediatric QoL Inventory (PedsQL) questionnaire was assessed as an exploratory endpoint. Caregivers of patients ≥2 years old completed the PedsQL questionnaire, which assessed patient functioning in physical, emotional, social, and school domains; the output is a score between 0 and 100, where higher scores indicate better functioning and a higher change from baseline indicates an improvement in QoL. In addition, caregivers completed the PedsQL Family Impact Module, which assesses physical, emotional, social, and cognitive functioning as well as communication, worry, daily activities, and family relationship domains, also on a scale of 0 to 100. Total scores at baseline and at week 24 for all treatment groups as well as mean changes in scores from baseline to week 24 are presented for both odevixibat doses combined vs placebo; these are summarized descriptively.

The primary safety analysis for PEDFIC 1 was based on incidence of treatment-emergent adverse events (TEAEs).

Results

A total of 62 patients were randomized in PEDFIC 1, and 49 (79%) completed the 24-week treatment period; 11 patients discontinued treatment due to patient or caregiver judgment of no improvement or intolerable symptoms and rolled over into the long-term extension study prior to completing 24 weeks of treatment. Additionally, 1 patient treated with odevixibat 40 μg/kg/day discontinued due to noncompliance and inability to travel to the clinic, and 1 patient treated with odevixibat 120 μg/kg/day discontinued early due to a TEAE of diarrhea. Baseline demographics and characteristics are shown in Table 12.

TABLE 12

Baseline Demographics and Characteristics

| | Placebo n = 20 | Odevixibat 40 pg/kg/day n = 23 | Odevixibat 120 pg/kg/day n = 19 | Odevixibat, All Doses n = 42 |
|---|---|---|---|---|
| Age, mean (SD), y | 3.8 (3.9) | 3.9 (3.7) | 5.2 (4.2) | 4.5 (3.9) |
| Sex, female, n (%) | 8 (40) | 12 (52) | 11 (58) | 23 (55) |
| PFIC type, n (%) | | | | |
| PFIC1 | 5 (25) | 7 (30) | 5 (26) | 12 (29) |
| PFIC2 | 15 (75) | 16 (70) | 14 (74) | 30 (71) |
| UDCA at baseline, n (%) | 18 (90) | 19 (83) | 13 (68) | 32 (76) |

TABLE 12-continued

| Baseline Demographics and Characteristics | | | | |
|---|---|---|---|---|
| | Placebo n = 20 | Odevixibat 40 pg/kg/day n = 23 | Odevixibat 120 pg/kg/day n = 19 | Odevixibat, All Doses n = 42 |
| baseline, n (%) Serum bile acids, mean (range), μmol/L | 248 (57-435) | 254 (76-605) | 249 (36-600) | 252 (36-605) |
| Pruritus score, mean (range) | 3.0 (1.9-4.0) | 3.0 (2.0-4.0) | 2.8 (1.6-3.4) | 2.9 (1.6-4.0) |
| Serum ALT, mean (range), U/L | 77 (19-236) | 128 (21-798) | 89 (16-314) | 110 (16-798) |
| Total serum bilirubin, mean (range), mg/dL | 3.1 (0.3-11.4) | 3.1 (0.3-12.7) | 3.3 (0.2-18.6) | 3.2 (0.2-18.6) |

ALT, alanine aminotransferase; PFIC, progressive familial intrahepatic cholestasis; SD, standard deviation; UDCA, ursodeoxycholic acid.

Quality of Life

Figure 15:
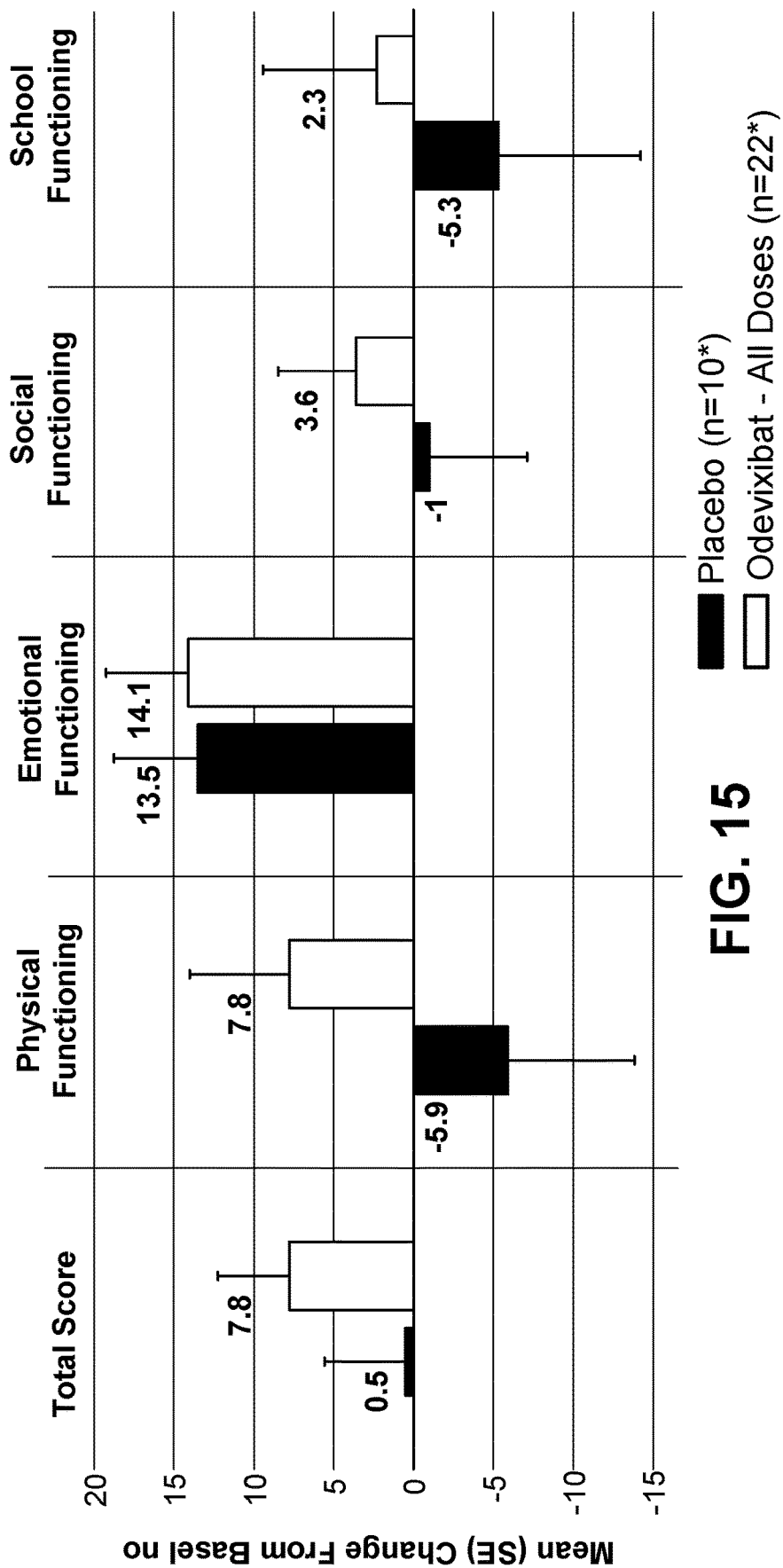
FIG. 15 is a graph of the mean (SE) change from baseline to week 24 in the PedsQL total and domain scores (physical functioning, emotional functioning, social functioning, and school functioning) for placebo (n=10) and Odevixibat (n-22). For school functioning, n=6 for placebo and n=15 for odevixibat—all doses. n, number of patients with available assessments; PedsQL, Pediatric Quality of Life Inventory; SE, standard error.

PedsQL total scores showed improved QoL with odevixibat vs placebo (mean change from baseline to week 24, 7.8 vs 0.5, respectively) (FIG. 15 and Table 13). Among PedsQL domains, improvements in mean changes from baseline to week 24 were observed with odevixibat, whereas with placebo, 3 of 4 domains showed worsening. (Physical: 7.8 with odevixibat vs −5.9 with placebo; Emotional: 14.1 vs 13.5; Social: 3.6 vs −1.0; and school functioning: 2.3 vs −5.3).

Figure 16:
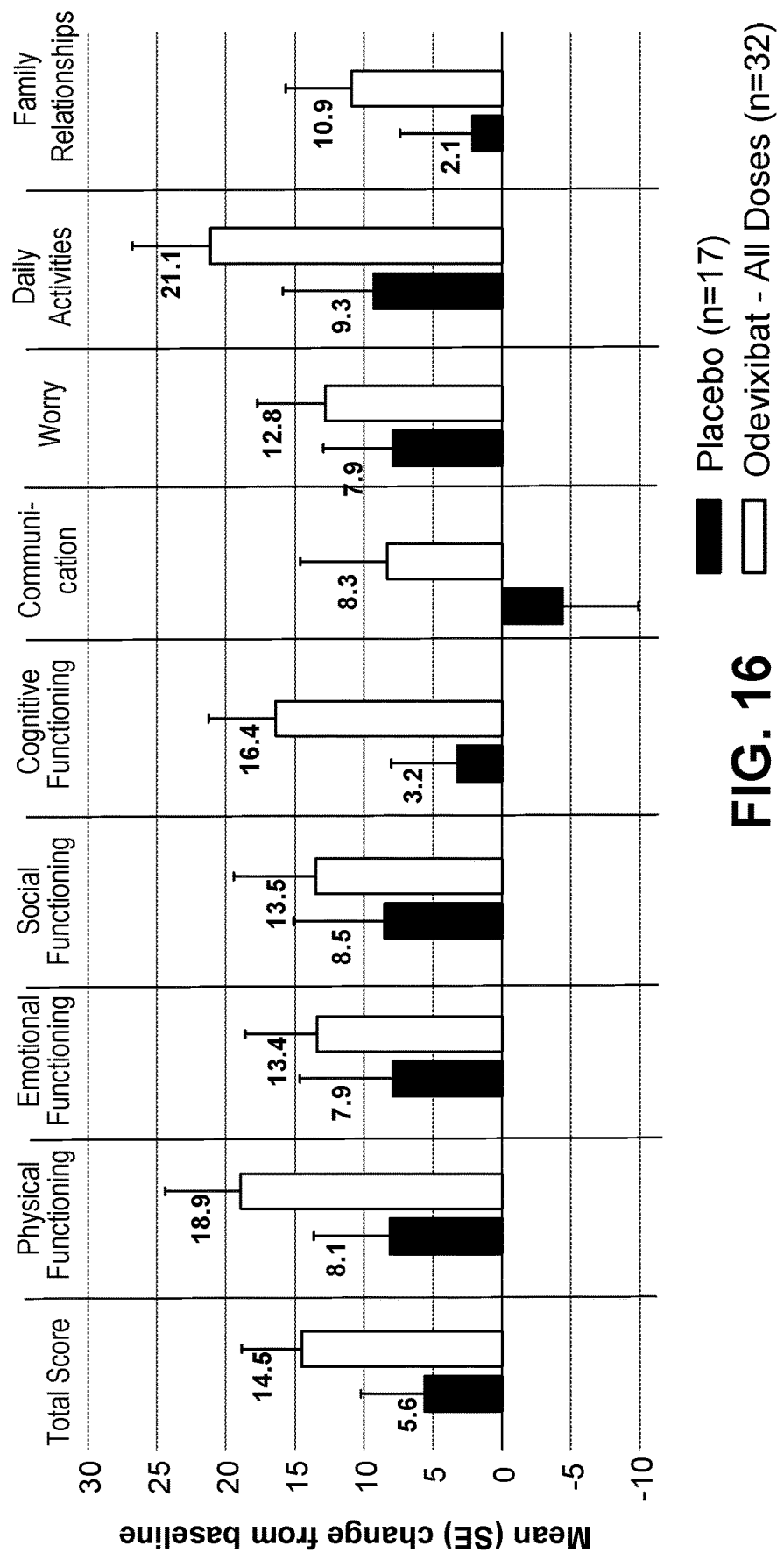
FIG. 16 is a graph of the mean (SE) change from baseline to week 24 in the PedsQL family impact module total and domain scores (Physical functioning, Emotional functioning, Social functioning, Cognitive functioning, Communication, Worry, Daily activities, Family relationships) for placebo (n=17) and Ocevixibat (n=32). n, number of patients with available assessments; PedsQL, Pediatric Quality of Life Inventory; SE, standard error.

Larger mean improvements in mean change from baseline to week 24 were observed with odevixibat vs placebo in Family Impact Module total score and other key domain scores (FIG. 16 and Table 14). Total: 14.5 with odevixibat vs 5.6 with placebo, Physical: 18.9 vs 8.1; Emotional: 13.4 vs 7.9; Social: 13.5 vs 8.5; Cognitive: 16.4 vs 3.2; Communication: 8.3 vs −4.4; Worry: 12.8 vs 7.9; Daily activities: 21.1 vs 9.3; and Family relationships: 10.9 vs 2.1.

TABLE 13

PedsQL Total and Domain Scores at Baseline and Week 24

| | Placebo | | Odevixibat 40 μg/kg/day | | Odevixibat 120 μg/kg/day | | Odevixibat, All Doses | |
|---|---|---|---|---|---|---|---|---|
| | Baseline | Week 24 | Baseline | Week 24 | Baseline | Week 24 | Baseline | Week 24 |
| Total score | | | | | | | | |
| n | 12 | 10 | 16 | 13 | 10 | 11 | 26 | 24 |
| Mean (SE) | 56.7 (4.1) | 57.9 (5.0) | 52.4 (3.8) | 56.8 (4.0) | 50.6 (4.5) | 60.7 (7.0) | 51.7 (2.8) | 58.6 (3.8) |
| Physical functioning | | | | | | | | |
| n | 12 | 10 | 16 | 13 | 10 | 11 | 26 | 24 |
| Mean (SE) | 58.3 (5.8) | 55.6 (7.8) | 52.2 (4.8) | 56.3 (4.0) | 49.1 (8.9) | 56.8 (8.7) | 51.0 (4.4) | 56.5 (4.4) |
| Emotional functioning | | | | | | | | |
| n | 12 | 10 | 16 | 13 | 10 | 11 | 26 | 24 |
| Mean (SE) | 45.0 (6.5) | 58.5 (7.8) | 46.9 (4.7) | 54.6 (4.7) | 36.0 (3.4) | 59.6 (6.9) | 42.7 (3.3) | 56.9 (4.0) |
| Social functioning | | | | | | | | |
| n | 12 | 10 | 16 | 13 | 10 | 11 | 26 | 24 |
| Mean (SE) | 67.1 (5.8) | 64.0 (5.0) | 63.1 (5.5) | 63.1 (6.4) | 61.0 (7.9) | 65.9 (8.6) | 62.3 (4.5) | 64.4 (5.1) |
| School functioning | | | | | | | | |
| n | 7 | 7 | 11 | 9 | 7 | 10 | 18 | 19 |
| Mean (SE) | 60.0 (6.0) | 55.5 (7.5) | 45.6 (4.4) | 53.2 (5.2) | 59.3 (8.7) | 63.3 (7.6) | 50.9 (4.5) | 58.5 (4.7) | n, number of patients with available assessments; PedsQL, Pediatric Quality of Life Inventory; SE, standard error.

TABLE 14

PedsQL Family Impact Module Total and Domain Scores at Baseline and 24 Weeks

| Score, Mean (SE) | Placebo Baseline (n = 19) | Placebo Week 24 (n = 17) | Odevixibat 40 μg/kg/day Baseline (n = 23) | Odevixibat 40 μg/kg/day Week 24 (n = 19) | Odevixibat 120 μg/kg/day Baseline (n = 16) | Odevixibat 120 μg/kg/day Week 24 (n = 15) | Odevixibat, All Doses Baseline (n = 39) | Odevixibat, All Doses Week 24 (n = 34) |
|---|---|---|---|---|---|---|---|---|
| Total score | 53.3 (4.0) | 57.5 (5.6) | 47.7 (4.0) | 58.4 (4.7) | 43.4 (3.3) | 63.5 (5.3) | 45.9 (2.7) | 60.6 (3.5) |
| Physical functioning | 48.5 (3.8) | 54.4 (6.6) | 42.6 (4.4) | 57.0 (5.7) | 41.4 (4.8) | 63.3 (5.6) | 42.1 (3.2) | 59.8 (4.0) |
| Emotional functioning | 46.3 (5.9) | 55.3 (6.5) | 46.3 (5.1) | 55.8 (5.6) | 41.3 (3.7) | 63.0 (5.9) | 44.2 (3.3) | 59.0 (4.1) |
| Social functioning | 60.2 (6.2) | 64.7 (7.0) | 53.3 (6.4) | 61.8 (6.4) | 44.1 (4.8) | 64.6 (7.6) | 49.5 (4.3) | 63.1 (4.8) |
| Cognitive functioning | 62.4 (4.9) | 62.7 (5.9) | 51.5 (5.1) | 65.3 (4.9) | 45.9 (3.7) | 67.7 (6.2) | 49.2 (3.4) | 66.3 (3.8) |
| Communication | 62.7 (6.8) | 59.8 (5.6) | 54.4 (5.7) | 57.0 (5.6) | 53.1 (6.8) | 68.9 (5.6) | 53.9 (4.3) | 62.3 (4.1) |
| Worry | 39.0 (5.7) | 48.2 (5.8) | 36.3 (4.7) | 47.9 (5.3) | 34.1 (4.4) | 52.0 (5.8) | 35.4 (3.3) | 49.7 (3.9) |
| Daily activities | 40.8 (6.8) | 47.1 (7.7) | 31.9 (4.9) | 50.9 (6.1) | 34.4 (4.6) | 54.4 (8.1) | 32.9 (3.4) | 52.5 (4.9) |
| Family relationships | 67.6 (4.5) | 66.5 (6.8) | 64.1 (5.5) | 68.7 (5.9) | 53.4 (5.3) | 72.7 (5.6) | 59.7 (3.9) | 70.4 (4.1) |

PedsQL FI, Pediatric Quality of Life Family Inventory; SE, standard error.

Safety

Overall, most TEAEs were mild to moderate in severity and assessed as unrelated to study treatment. There were no deaths or treatment-related serious adverse events in the study. One patient receiving odevixibat 120 μg/kg/day discontinued treatment due to a TEAE of diarrhea.

In conclusion, Odevixibat improved patient and family QoL, in parallel with improvements in clinical signs and symptoms of the underlying disease in the PEDFIC 1 study. In addition to overall improvement in QoL with odevixibat, this study identified improvements in school functioning consistent with previously published findings from children with PFIC following surgical interruption of the enterohepatic circulation (see, e.g., Yang, et al., *J. Pediatr Gastroenterol Nutr.*, 2009, 49:216-21). Overall, odevixibat, which is a pharmacologic approach to diverting the enterohepatic circulation away from the liver, is a noninvasive treatment option for patients with PFIC.

Example 10—the ASSERT Study: A Phase 3 Double-Blind, Randomized, Placebo-Controlled Study of the Safety and Efficacy of Odevixibat in Patients with Alagille Syndrome Alagille syndrome (ALGS) is a rare, inherited cholestatic liver disease typically presenting within the first 3 months of life. Clinical features of ALGS can include mild to end-stage liver disease and pruritus, with up to 88% of patients presenting with pruritus and up to 45% having severe pruritus. No approved medical therapy is currently available for the treatment of ALGS. Odevixibat can be used to reduce systemic bile acids, improve liver function, and decrease pruritus in patients with ALGS. The ASSERT study evaluates odevixibat as a potential treatment for pruritus in ALGS.

This double-blind, randomized, placebo-controlled, multicenter phase 3 trial (ClinicalTrials.gov identifier: NCT04674761) will enroll approximately 63 patients, including approximately 45 patients aged <18 years and an additional exploratory cohort of up to 18 patients aged ≥18 years. To be included, patients must have a genetically confirmed diagnosis of ALGS, history of significant pruritus, and elevated serum bile acid levels at 2 screening visits. Exclusion criteria include presence or medical history of other types of liver disease, inflammatory bowel disease, and chronic kidney disease; serum alanine aminotransferase levels >10-fold above the upper limit of normal (ULN) or total bilirubin levels >15-fold above the ULN at screening; and biliary diversion surgery in the 6 months prior to study start or liver transplantation planned within 6 months following randomization. Eligible patients are randomized 2:1 to receive either 120 μg/kg/day odevixibat or placebo capsules for oral administration once daily for 24 weeks. The primary efficacy endpoint is change from baseline scratching score to month 6 (weeks 21-24) as measured by the observer-reported outcome pruritus instrument. The key secondary endpoint is change in serum bile acid levels from baseline to the average of weeks 20 and 24. Additional secondary endpoints include changes in patient- and observer-reported pruritus as well as xanthomatosis, sleep parameters, and quality of life, in addition to monitoring of liver function. Safety and tolerability are assessed by analyzing treatment-emergent adverse events, as well as physical examination, vital signs, laboratory tests, liver ultrasound, and liver elastography. Following study completion, patients will be eligible to receive odevixibat through an open-label extension study.

By reducing bile acid load, odevixibat could provide a new medical intervention option for patients with ALGS to reduce pruritus and improve hepatic outcomes.

Example 11—Efficacy and Safety of Odevixibat in Children with Progressive Familial Intrahepatic Cholestasis with Prior Partial External Biliary Diversion One surgical treatment option for patients with PFIC is partial external biliary diversion (PEBD), which can be used to reduce bile acid levels in patients with medically refractory pruritus. However, PEBD is not successful in all patients. As described herein, odevixibat treatment reduced serum bile acids (sBAs) and improved pruritus in patients with PFIC. This post hoc subgroup analysis evaluated the safety and efficacy of odevixibat in patients enrolled in the PEDFIC studies who had PEBD surgery prior to study entry.

In the double-blind PEDFIC 1 study, children with PFIC1 or PFIC2 were randomized to placebo or 40 or 120 μg/kg/day odevixibat for 24 weeks. In PEDFIC 2, an ongoing, open-label extension study, patients from PEDFIC 1 or newly enrolled patients with any PFIC subtype receive odevixibat 120 μg/kg/day. In both PEDFIC 1 and PEDFIC 2, eligible patients had elevated sBAs and significant pruritus at screening. Changes over time in sBA levels and observer-reported pruritus (range: 0-4; higher scores indicate worse symptoms), sleep parameters, and quality of life (QoL; assessed with the Pediatric Quality of Life Inventory [PedsQL]) were evaluated in the subgroup of patients from PEDFIC 1 and/or PEDFIC 2 with a medical history of PEBD surgery performed prior to study enrollment.

A total of 10 patients with prior PEBD surgery (median [range] age, 8 [3.5-12 years) were enrolled (Table 15). All patients had elevated sBAs and pruritus scores prior to the first dose of odevixibat, indicating that prior PEBD surgery was unsuccessful or only partially successful. In 9 patients, the approximate mean time from PFIC diagnosis to surgery was 1 year; the other patient underwent surgery approximately 2 years before receiving a diagnosis. Of these 10 patients, 8 enrolled in PEDFIC 1 and continued into PEDFIC 2, and 2 additional patients were newly enrolled in PEDFIC 2. With odevixibat treatment, 7 patients had reductions in pruritus score and 4 met criteria for pruritus response (ie, ≥1-point drop in pruritus score). Overall, 5 patients had reductions in sBA levels; 1 patient, who also met pruritus response criteria, met criteria for sBA response (ie, sBAs reduced by ≥70% or levels ≤70 μmol/L) at last assessment (Table 15). Of the 9 patients with post-baseline QoL assessments, 6 had improved observer-reported PedsQL total scores, including all 4 pruritus and/or sBA responders. The 4 pruritus and/or sBA responders also had reductions from baseline to last assessment in percentage of days with bleeding associated with scratching, needing soothing or help falling asleep, and sleeping with caregivers. Treatment-emergent adverse events (TEAEs) were observed in 9 (90%) patients in the subgroup of patients with prior PEBD; all TEAEs were mild to moderate in severity, and no patients discontinued due to a TEAE. As of the data cutoff, 9 of the 10 patients were continuing in the study; 1 patient discontinued with a reason of "other" (due to lack of treatment effect).

Improvements were observed in sBA levels, pruritus, QoL, and sleep parameters in some patients enrolled in the PEDFIC 1 and PEDFIC 2 studies who had prior PEBD surgery. These improvements were observed despite elevated sBAs and pruritus in these patients at baseline, suggesting that some patients with poor response to PEBD could potentially respond to odevixibat treatment. Odevixibat was generally well tolerated in these patients.

TABLE 15

Treatment Effects in Patients with Prior Partial External Biliary Diversion Surgery

| Patient | PEDFIC 1 Treatment | PEDFIC 2 Treatment | PFIC Type | Age, years | Total Odevixibat Exposure, weeks | Baseline Pruritus Score | Change From Baseline in Pruritus Score | Pruritus Responder?[a] | Baseline sBAs, μmol/L | Change From Baseline in sBAs, μmol/L | sBA Responder?[b] |
|---|---|---|---|---|---|---|---|---|---|---|---|
| 1 | Placebo | Odevixibat 120 μg/kg/d | 2 | 8 | 42 | 1.9 | 0.1 | N | 172 | −18 | N |
| 2 | Placebo | Odevixibat 120 μg/kg/d | 1 | 4.6 | 35 | 3.8 | −0.9 | N | 225 | −69.5 | N |
| 3 | Odevixibat 40 μg/kg/d | Odevixibat 120 μg/kg/d | 1 | 8 | 44 | 3.0 | −2.1 | Y | 193 | 197 | N |
| 4 | Odevixibat 40 μg/kg/d | Odevixibat 120 μg/kg/d | 1 | 3.5 | 55 | 3.0 | −1.5 | Y | 163 | −53.5 | N |
| 5 | Odevixibat 120 μg/kg/d | Odevixibat 120 μg/kg/d | 2 | 12 | 53 | 2.8 | 0.3 | N | 156.5 | −11.5 | N |
| 6 | Odevixibat 120 μg/kg/d | Odevixibat 120 μg/kg/d | 2 | 5 | 44 | 3.0 | 0.0 | N | 237 | 103 | N |
| 7 | Odevixibat 120 μg/kg/d | Odevixibat 120 μg/kg/d | 2 | 4.4 | 54[c] | 2.9 | −0.3 | N | 208 | 178 | N |
| 8 | Odevixibat 120 μg/kg/d | Odevixibat 120 μg/kg/d | 1 | 10.2 | 47 | 2.0 | −2.1 | Y | 188.5 | 61.5 | N |
| 9 | NA | Odevixibat 120 μg/kg/d | 1 | 11 | 25 | 2.0 | −0.5 | N | 139.5 | 8.5 | N |
| 10 | NA | Odevixibat 120 μg/kg/d | 2 | 8.1 | 35 | 2.5 | −1.5 | Y | 79.5 | −70.5 | Y |

[a] ≥1-point drop in pruritus score at last assessment:
[b] sBAs reduced ≥70% or levels ≤70 μmol/L at last assessment:
[c] Patient 7 discontinued the study, but the date of discontinuation is not available.
N, no; NA, not applicable; PFIC, progressive familial intrahepatic cholestasis; sBA, serum bile acid; Y, yes.

Example 12—Efficacy and Safety of Odevixibat Therapy with Concomitant UDCA or Rifamicin in Children with Progressive Familial Intrahepatic Cholestasis: Date from the PEDFIC 1 and PEFIC 2 Trials Current pharmacologic treatment options for PFIC include ursodeoxycholic acid (UDCA) and rifampicin, but these do not have proven long-term benefits in patients with PFIC. The phase 3 PEDFIC 1 and PEDFIC 2 studies evaluated the safety and efficacy of odevixibat in pediatric patients with PFIC; in both studies, odevixibat treatment reduced serum bile acids, improved pruritus, and was generally well tolerated. In an analysis of pooled data from PEDFIC 1 and PEDFIC 2, it was evaluated whether the observed effects regarding efficacy and safety were related to concomitant treatment with UDCA and/or rifampicin.

Methods: In the double-blind PEDFIC 1 study, children with PFIC1 or PFIC2 were randomized to placebo or odevixibat 40 or 120 μg/kg/day for 24 weeks. In PEDFIC 2, an ongoing, open label extension study, patients from PEDFIC 1 or new patients with any PFIC subtype received odevixibat 120 μg/kg/day. Concomitant UDCA and/or rifampicin were allowed if the patient was on a stable dose. This pooled analysis includes up to 48 weeks of odevixibat treatment from PEDFIC 1 and through the PEDFIC 2 interim data cut (37 weeks; range: 1-108 weeks). Pre-specified subgroup analyses evaluated the following outcomes based on use of UDCA and/or rifampicin: serum bile acid response (i.e., ≥70% reduction from baseline or serum bile acid levels ≤70 μmol/L after 48 weeks), proportion of positive pruritus assessments (PPAs) at the patient level (i.e., scratching score ≤1 or a ≥1-point drop from baseline on the validated PRUCISION instrument) over the 48-week treatment period, and treatment-emergent adverse events (TEAEs).

Results: Of the 77 patients who received odevixibat, 67 (87%) were receiving UDCA and/or rifampicin at baseline, including 62 (81%) using UDCA and 48 (62%) using rifampicin. After 48 weeks of odevixibat treatment, percentages of patients meeting criteria for serum bile acid response were similar among patients using vs not using UDCA and/or rifampicin (both 67%); these proportions were 74% and 40% in patients using vs not using UDCA, respectively, and 54% and 82% in patients using vs not using rifampicin. Mean proportions of PPAs were similar in patients using vs not using UDCA (65% vs 72%, respectively) and in patients using vs not using UDCA and/or rifampicin (66% vs 69%), but mean proportion of PPAs was somewhat lower in patients using rifampicin (56%) vs not using rifampicin (81%). Incidence of TEAEs was similar in patients using vs not using UDCA and/or rifampicin (78% vs 90%, respectively), as well as in patients using vs not using UDCA (77% vs 87%) and rifampicin (75% vs 86%).

Conclusion: In the PEDFIC 1 and PEDFIC 2 studies, children with PFIC receiving odevixibat treatment experienced reductions in serum bile acids and improvements in pruritus with and without concomitant UDCA and/or rifampicin use. Safety and tolerability were comparable in patients using vs not using UDCA and/or rifampicin with odevixibat.

Example 13—Efficacy and Safety of Odevixibat Therapy with Concomitant UDCA or Rifamicin in Children with Progressive Familial Intrahepatic Cholestasis: Date from the PEDFIC 1 and PEFIC 2 Trials Patients with PFIC frequently have elevated serum bile acids, fat soluble vitamin deficiency, debilitating pruritus that can lead to considerable sleep disturbance, and progressive liver damage. Although not well understood, higher levels of serum bile acids correlate with worsening symptoms of pruritus. PEDFIC1 and PEDFIC2 are phase 3 interventional studies of odevixibat, in patients with PFIC. To improve the understanding of the relationships between serum bile acid levels, pruritus, and sleep parameters, these aspects of disease were investigated using pooled data from the PEDFIC studies.

Methods: PEDFIC 1 was a randomized, double-blind study in children with PFIC1 or PFIC2; patients received either once-daily placebo, odevixibat 40 μg/kg, or odevixibat 120 μg/k g for 24 weeks. PEDFIC 2 is an ongoing, 72 week extension study in patients with any type of PFIC in which all patients receive odevixibat 120 μg/kg/day. In both PEDFIC 1 and PEDFIC 2, eligible patients had elevated serum bile acids and significant pruritus at screening. Here, patient pruritus and sleep-related data (including tiredness during the day) were included, which were evaluated twice daily by caregivers using the validated PRUCISION scale via an electronic diary. Pruritus and tiredness responses range from 0 to 4, with higher scores indicating worse symptoms; other sleep assessments include questions with Yes/No response s. Correlations between percentage change from baseline in serum bile acids and change from baseline in observer-reported diary data (pruritus, sleep characteristics) were assessed as post hoc analyses and are summarized with Pearson coefficient s (r).

Results: Prior to starting treatment, the median age of the 84 patients included in this analysis was 3.6 years. Overall, 22 patients (26%) had PFIC1, 56 (67%) had PFIC2, 5 (6%) had PFIC3 (MDR3 deficiency), and 1 (1%) had PFIC6 (MYO5B deficiency). Patients had mean (SE) serum bile acid levels of 246 (14) μmol/L, mean (SE) pruritus scores of 2.8 (0.1), mean (SD) ALT levels of 92 U/L (104), mean (SD) AST levels of 97 U/L (67), and mean (SD) total bilirubin levels of 2.9 mg/dL (3.5) prior to the first dose of odevixibat (see Table 16A and Table 16B) for these and other data summarized below). At the data cutoff date, median exposure to odevixibat was 53 weeks and nearly one-third of patients (31%) had received odevixibat for ≥76 weeks. Most patients (66/84) were still on treatment at the data cutoff date. Over the treatment interval with odevixibat, patients had mean decreases in serum bile acid levels and experienced improvements in pruritus scores and several sleep parameters. Mean percentage change in serum bile acids from baseline to weeks 49-72 was significantly correlated with mean change in pruritus scores during that interval (r=0.58; P<0.001). Moderate correlations were also observed between percentage change in serum bile acids from baseline to weeks 49-72 and changes during that interval in caregiver-reported percentage of days where patients had bleeding associated with scratching, needed soothing or help falling asleep, and were sleeping with caregivers (all r≥0.44; P<0.05). While 71 patients (85%) reported treatment-emergent adverse event (TEAE), most (90%) were mild or moderate in severity. No serious drug-related TEAEs or deaths occurred. The overall incidence of any event of diarrhea was 21% (occurring in 18/84 patients); all instances were mild to moderate in severity and resolved, most without intervention.

TABLE 16A

Correlation of Change From Baseline in Pruritus and Sleep Parameters With Percentage Change in Serum Bile Acid Levels

| | Baseline | | Change From Baseline to Weeks 49-72 | | Correlation With Percentage Change in Serum Bile Acid Level From Baseline to Weeks 49-72, $r^a$ | P value |
|---|---|---|---|---|---|---|
| | n | Mean (SE) | n | Mean (SE) | | |
| Serum bile acids, μmol/L | 84 | 246 (14) | 32 | −53% (9%) | NA | NA |
| Pruritus score | 82 | 2.8 (0.1) | 34 | −1.5 (0.2) | 0.58 | <0.001 |
| Days with scratching associated with bleeding, % | 82 | 38 (4) | 34 | −21 (7) | 0.62 | <0.001 |
| Days patient needed help falling asleep, % | 82 | 78 (4) | 34 | −55 (8) | 0.50 | 0.005 |
| Days patient needed soothing, % | 82 | 75 (4) | 34 | −48 (9) | 0.61 | <0.001 |
| Days patient slept with caregiver, % | 82 | 67 (5) | 34 | −38 (8) | 0.44 | 0.01 |
| Number of awakenings | 82 | 8 (1) | 34 | −7 (3) | 0.33 | 0.08 |
| Days taking medications to induce sleep, % | 82 | 24 (4) | 34 | −3 (4) | 0.15 | 0.43 |
| Tiredness score | 82 | 2.3 (0.1) | 34 | −1.2 (0.2) | 0.27 | 0.14 |

$^a$Correlation data available for n = 30.

NA, not applicable, r, Pearson coefficient.

TABLE 16B contains the baseline characteristics of treatment responders and nonresponders.

| | All | Serum bile acid response[1] | | Serum bile acid and/or Pruritus Response[2] | |
|---|---|---|---|---|---|
| | Odevixibat N = 84 | Responder N = 30 | Nonresponder N = 51 | Responder N = 49 | Nonresponder N = 35 |
| Age, mean (SD), years | 5.0 (4.8) | 4.3 (4.5) | 5.8 (5.0) | 4.8 (4.5) | 5.5 (5.2) |
| Female, n (%) | 41 (49) | 20 (67) | 21 (41) | 28 (57) | 13 (37) |
| PFIC type, n (%) | | | | | |
| PFIC1 (FIC1 deficiency) | 22 (26) | 3 (10) | 19 (37) | 11 (22) | 11 (31) |
| PFIC2 (BSEP deficiency) | 56 (67) | 24 (80) | 29 (57) | 34 (69) | 22 (63) |
| PFIC3 (MDR3 deficiency) | 5 (6) | 2 (7) | 3 (6) | 3 (6) | 2 (6) |
| Other (MYO5B deficiency) | 1 (1) | 1 (3) | 0 | 1 (2) | 0 |
| Pruritus score, mean (SE) | 2.8 (0.1) | 2.8 (0.1) | 2.9 (0.1) | 2.8 (0.1) | 2.8 (0.1) |
| Serum bile acids, mean (SE) | 246 (14) | 226 (26) | 261 (17) | 237 (20) | 259 (20) |
| UDCA at baseline, n (%) | 64 (76) | 24 (80) | 39 (77) | 38 (78) | 26 (74) |
| Rifampicin at baseline, n (%) | 51 (61) | 14 (47) | 35 (69) | 27 (55) | 24 (69) |
| ALT, mean (SD), U/L | 92 (104) | 113 (147) | 81 (70) | 105 (126) | 75 (58) |
| AST, mean (SD), U/L | 97 (67) | 91 (55) | 102 (74) | 100 (66) | 94 (68) |
| Total bilirubin, mean (SD), mg/dL | 2.9 (3.5) | 1.6 (2.0) | 3.8 (4.0) | 2.2 (2.1) | 4.0 (4.7) |

[1]70% reduction in serum bile acids or serum bile acids ≤70 μmol/L;

[2]pruritus score reduction of ≥1 point from baseline

Conclusions: With up to 72 weeks of odevixibat treatment, significant correlations were observed between reductions in serum bile acids and reductions in pruritus and most sleep disturbance scores. In addition, odevixibat was generally well tolerated.

Figure 17A:
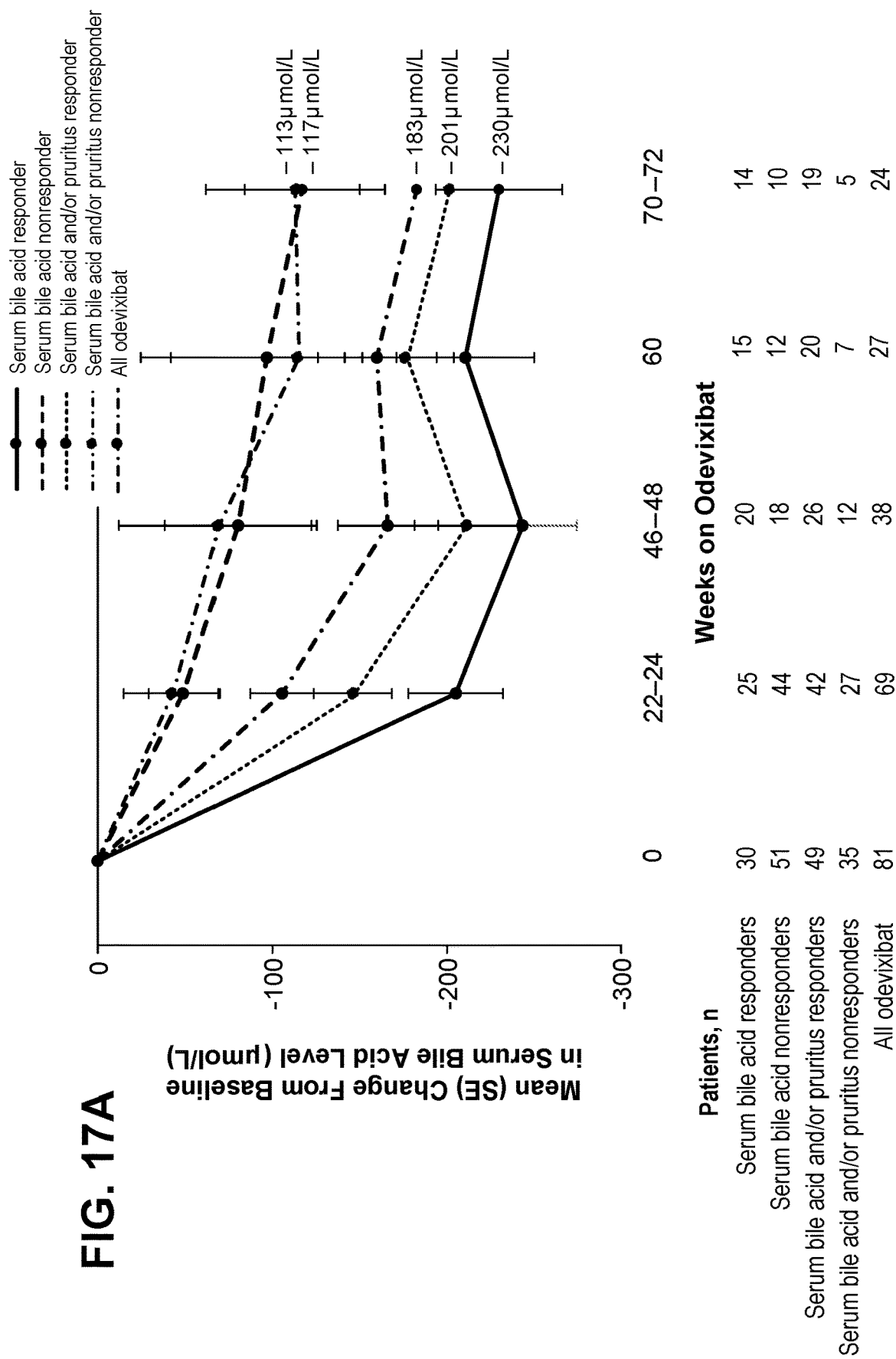
FIG. 17A is a graph of the change from baseline in serum bile acid levels over time in treatment responders and nonresponders and among all Odevixibat-treated patients.
Figure 17B:
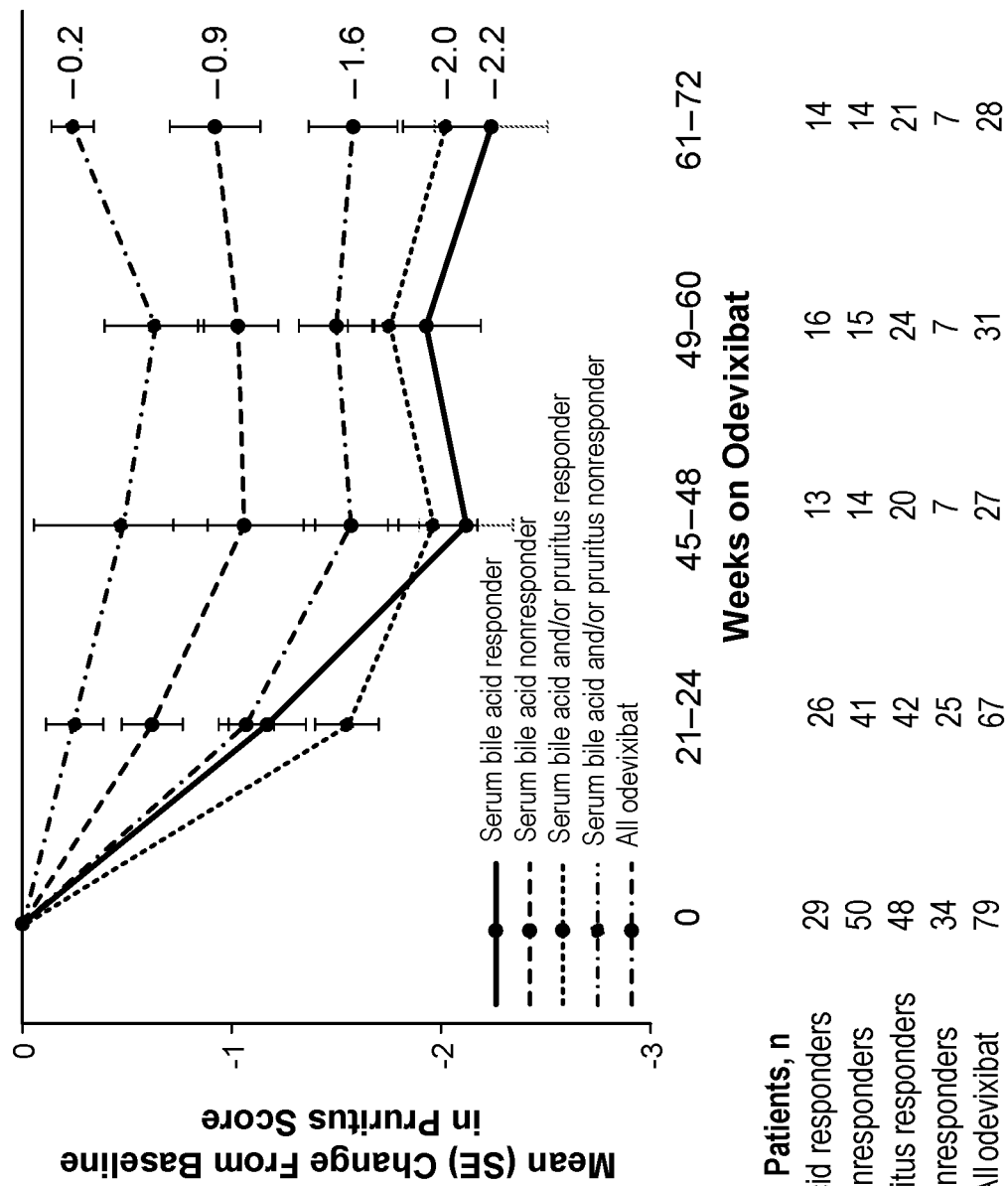
FIG. 17B is a graph of the change from baseline in pruritus scores over time in treatment responders and non-responders and among all Odevixibat-treated patients.

In addition, approximately 40% of patients met criteria for serum bile acid response during odevixibat treatment. When treatment response was defined by serum bile acid and/or pruritus criteria, approximately 60% of patients treated with odevixibat achieved a treatment response. From the start of odevixibat treatment to the end of the assessment period, responders had greater mean changes from baseline in serum bile acid levels and pruritus scores than nonresponders. See, FIGS. 17A and 17B. From baseline to week 72, both the overall population of odevixibat-treated patients and odevixibat responders had mean improvements (i.e., reductions) in transaminase and total bilirubin levels. Patients who were nonresponders had more pronounced growth deficits at baseline; however, with treatment, mean height and weight Z scores increased in the overall population of odevixibat-treated patients and in both responders and nonresponders. Responders and nonresponders had similar sleep characteristics at baseline. After 72 weeks of treatment, the overall population of odevixibat-treated patients as well as odevixibat responders had large decreases (i.e., improvements) in several caregiver-reported sleep parameters; increases or smaller changes were observed in nonresponders. Among all patients, 85% had any TEAE; this was similar across responders and nonresponders (83%-87%). Most TEAEs were mild or moderate in severity, regardless of treatment response. The most common TEAEs in odevixibat-treated patients were pyrexia, upper respiratory tract infections, and diarrhea. All serious TEAEs, regardless of treatment response, were assessed as unrelated to study drug.

Odevixibat treatment for up to 72 weeks in patients with PFIC was associated with improvement in hepatic health, quality of sleep, and growth, with greater improvement observed in responders compared with nonresponders. Patients with PFIC who responded to odevixibat had considerable reductions in mean serum bile acids and pruritus scores, with improvements sustained over time. Serum bile acid responders had larger improvements in pruritus than serum bile acid nonresponders. Odevixibat was generally well tolerated in both responders and nonresponders.

Example 14—Relationships Between Changes in Autotaxin, Pruritus, and Serum Bile Acids after Odevixibat Treatment in Patients with PFIC: Data from a Pooled Analysis This example assessed the relationship between changes in levels of autotaxin, pruritus, and serum bile acids in patients with PFIC treated with odevixibat in the phase 3 PEDFIC 1 and PEDFIC 2 studies. As described herein, PFIC is characterized by chronic cholestasis (high serum bile acids, severe pruritus) and progressive liver disease. Autotaxin is involved in the production of lysophosphatidic acid, and both are possible pruritic mediators. See, e.g., Thebaut, et al. *Clin Res Hepatol Gastroenterol.* 2018; 42:103-109. While some studies have shown a correlation between cholestatic pruritus and peripheral blood autotaxin levels, 3, 4 others have not 5, See, e.g, Kremer, et al., *Hepatology.* 2012; 56:1391-400; Kremer, et al., *J Pediatr Gastroenterol Nutr.* 2016; 62:530-5; and Fujino, et al., *BMC Gastroenterology.* 2019; 19:169.

Phase 3 study data of 77 patients treated with odevisibat was pooled from the PEDFIC 1 and PEDFIC 2 studies. In PEDFIC 1, patients received placebo or odevixibat 40 or 120 μg/kg/day for 24 weeks; in PEFFIC 2, patients were enrolled in an ongoing extension study, with all patients receiving 120 μg/kg/day. At the data cutoff, 77 patients had received odevixibat. The median length of odevixibat treatment was 37 weeks, with a range of 1-108 weeks. Most patients (88%) were continuing on treatment. Characteristics of patients with available data at weeks 25-48 who were included in the current analyses were generally similar to the overall study population. See Table 17.

TABLE 17

Demographics and Baseline Characteristics

| | Odevixibat Any dose N = 77 | Patients analyzed in correlations analyses, N = 44 |
|---|---|---|
| Age, mean (SD), years | 5.2 (4.3) | 3.9 (3.5) |
| Sex, female, n (%) | 39 (51) | 21 (48) |
| PFIC type, n (%) | | |
| PFIC1 | 20 (26) | 13 (30) |
| PFIC2 | 51 (66) | 31 (70) |
| PFIC3 | 5 (7) | 0 |
| Other | 1 (1) | 0 |
| UDCA use at baseline, n (%) | 62 (81) | 35 (80) |
| Rifampicin at baseline, n (%) | 48 (62) | 27 (61) |
| Serum ALT, mean (SD), U/L | 92 (108) | 105 (130) |
| Serum AST, mean (SD), U/L | 98 (69) | 95 (60) |
| Total bilirubin, mean (SD), mg/dl | 3.0 (3.6) | 3.2 (4.4) |

Autotaxin was assessed prior to treatment and throughout PEDFIC 1 and PEDFIC 2. Caregivers evaluated patients' pruritus using the validated PRUCISION scale, where scores range from 0 to 4; higher scores indicate worse symptoms. Serum bile acid measurements were taken at all study visits.

Relationships between changes from baseline to weeks 25-48 in autotaxin, pruritus, and serum bile acid levels were assessed as post hoc analyses. Changes from baseline were summarized descriptively. Pearson coefficients and P values were calculated for correlations. Responders were defined as ≥70% reduction from baseline in serum bile acids or serum bile acids ≤70 μmol/L at last assessment up to week 48 and/or pruritus score reduction of ≥1 point from baseline based on last available monthly or 12-week interval score up to week 48.

During treatment with odevixibat, mean decreases from baseline were observed in autotaxin or serum bile acid levels and pruritus scores. See Table 18. Values are based on last assessment up to week 48. For serum bile acids, this was the average value from weeks 46 and 48 when available; otherwise, the last available assessment in the interval was used. For pruritus, last monthly score was used when available; otherwise, the score from the last 12 weeks was used. For autotaxin, the last assessment within the interval was used.

TABLE 18

Changes in Autotaxin, Pruritis, and Serum Bile Acid Levels

| | Overall study population Baseline | | Patients analyzed in correlation analyses | | | | | |
|---|---|---|---|---|---|---|---|---|
| | | | Baseline | | Change from baseline to weeks 25-48 | | Percentage change from baseline to weeks 25-48 | |
| | N | Mean (SE) | N | Mean (SE) | N | Mean (SE) | N | Mean (SE) |
| Autotaxin ng/ml | 66 | 2289 (164) | 33 | 2938 (255) | 33 | −1696 (266) | 33 | −50% (6%) |
| Pruritus score (range, 0-4) | 75 | 2.9 (0.1) | 44 | 2.9 (0.1) | 44 | −1.4 (0.2) | NA | NA |
| Serum bile acids, μmol/L | 76 | 250 (15) | 44 | 256 (20) | 44 | −140 (25) | 44 | −49% (8%) |

NA—not assessed

Figure 18A:
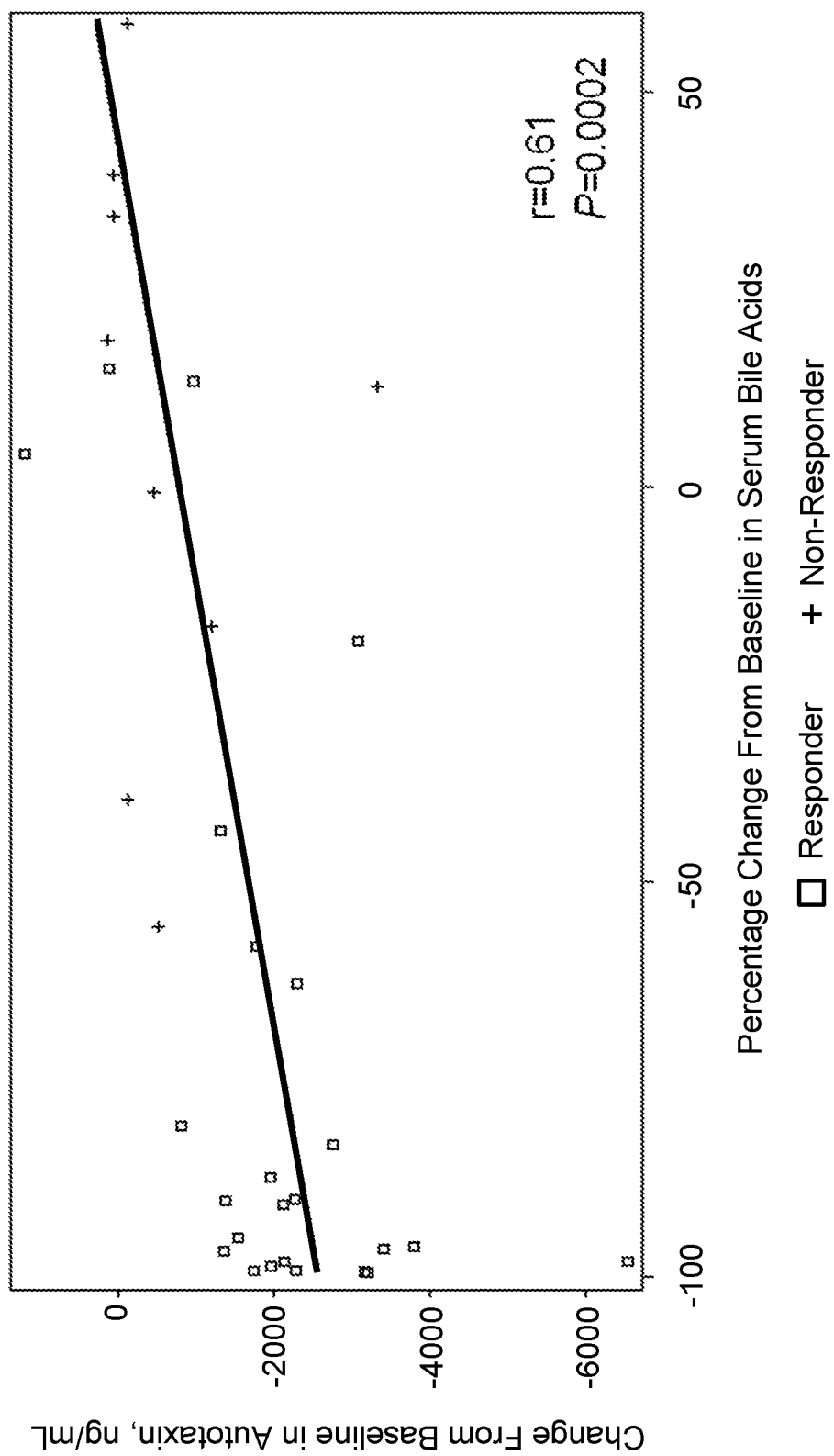
FIG. 18A is a graph of the change in autotaxin vs the percentage change in serum bile acids.
Figure 18B:
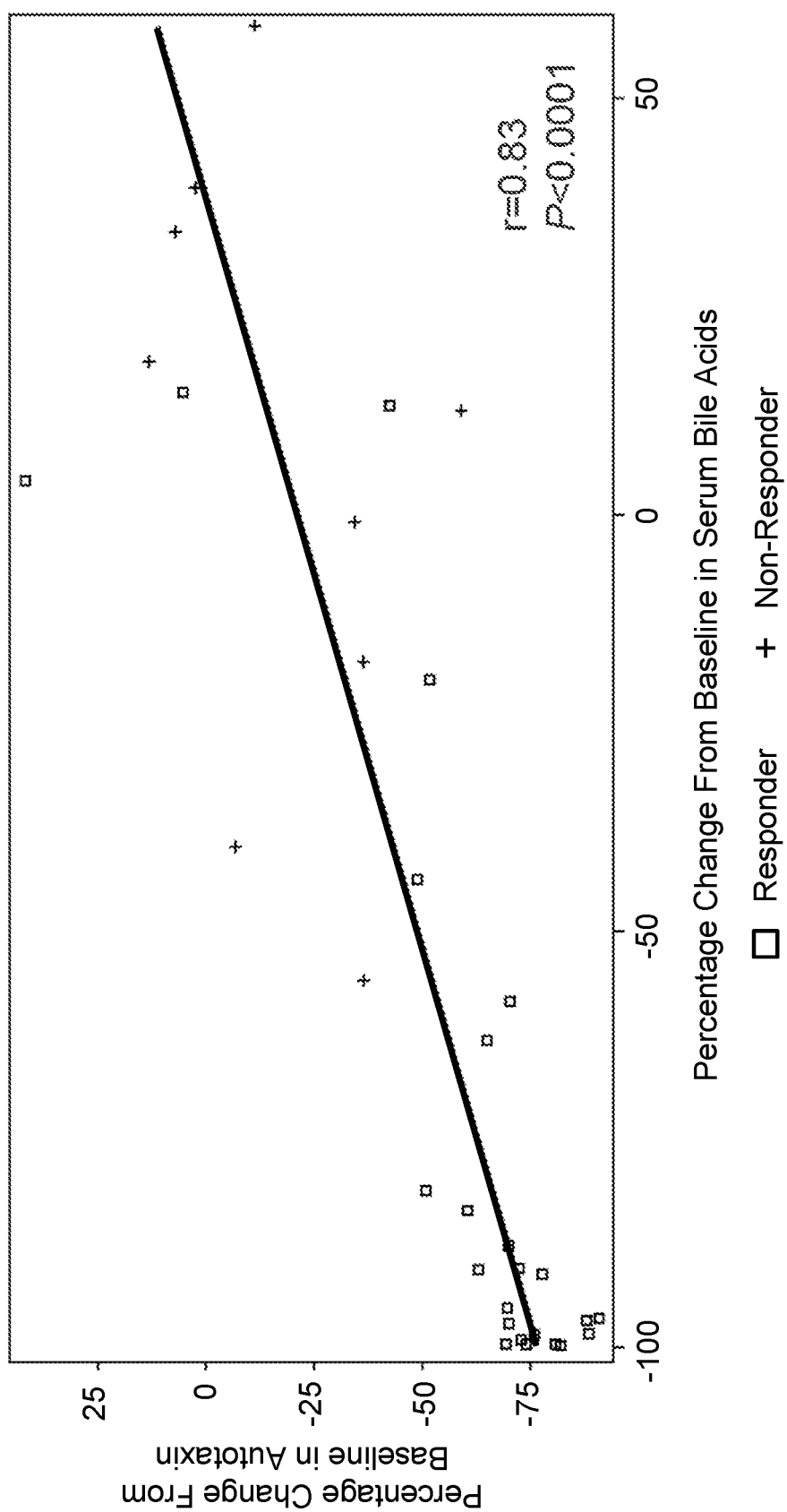
FIG. 18B is a graph of the percentage change in autotaxin vs percentage change in serum bile acids.
Figure 19A:
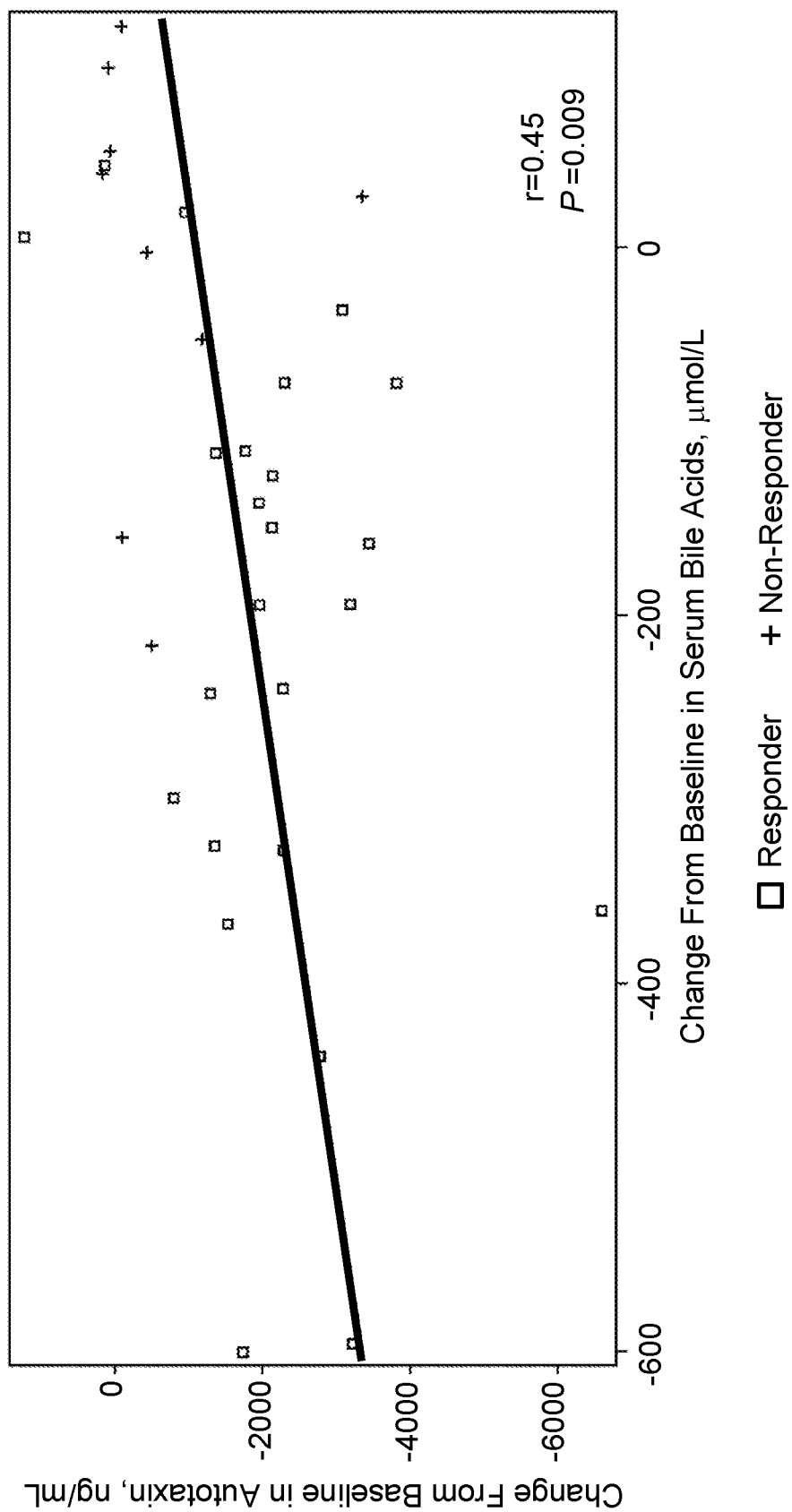
FIG. 19A is a graph of the change in autotaxin vs the change in serum bile acids.
Figure 19B:
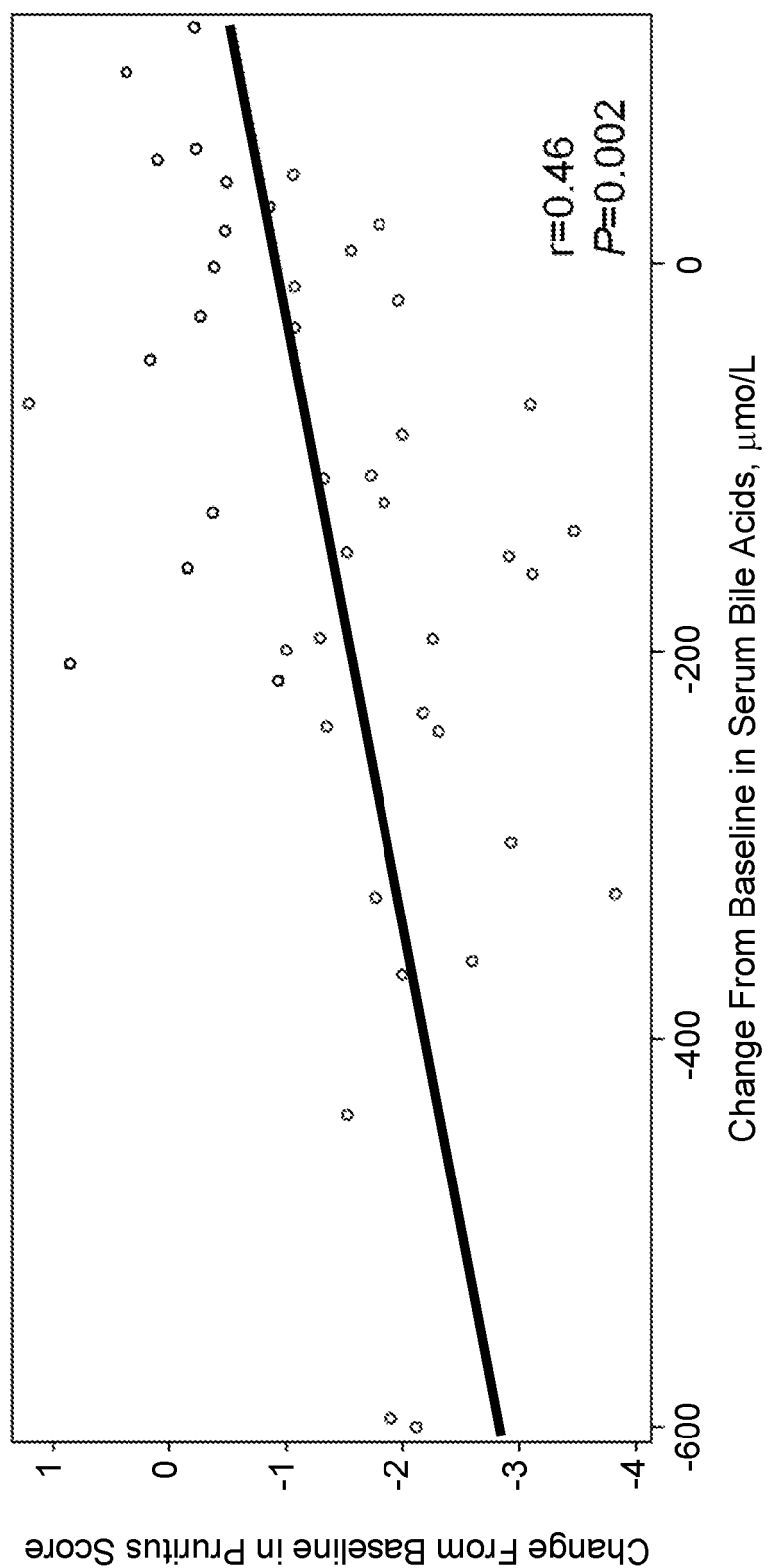
FIG. 19B is a graph of the change in pruritus vs change in serum bile acids.
Figure 19C:
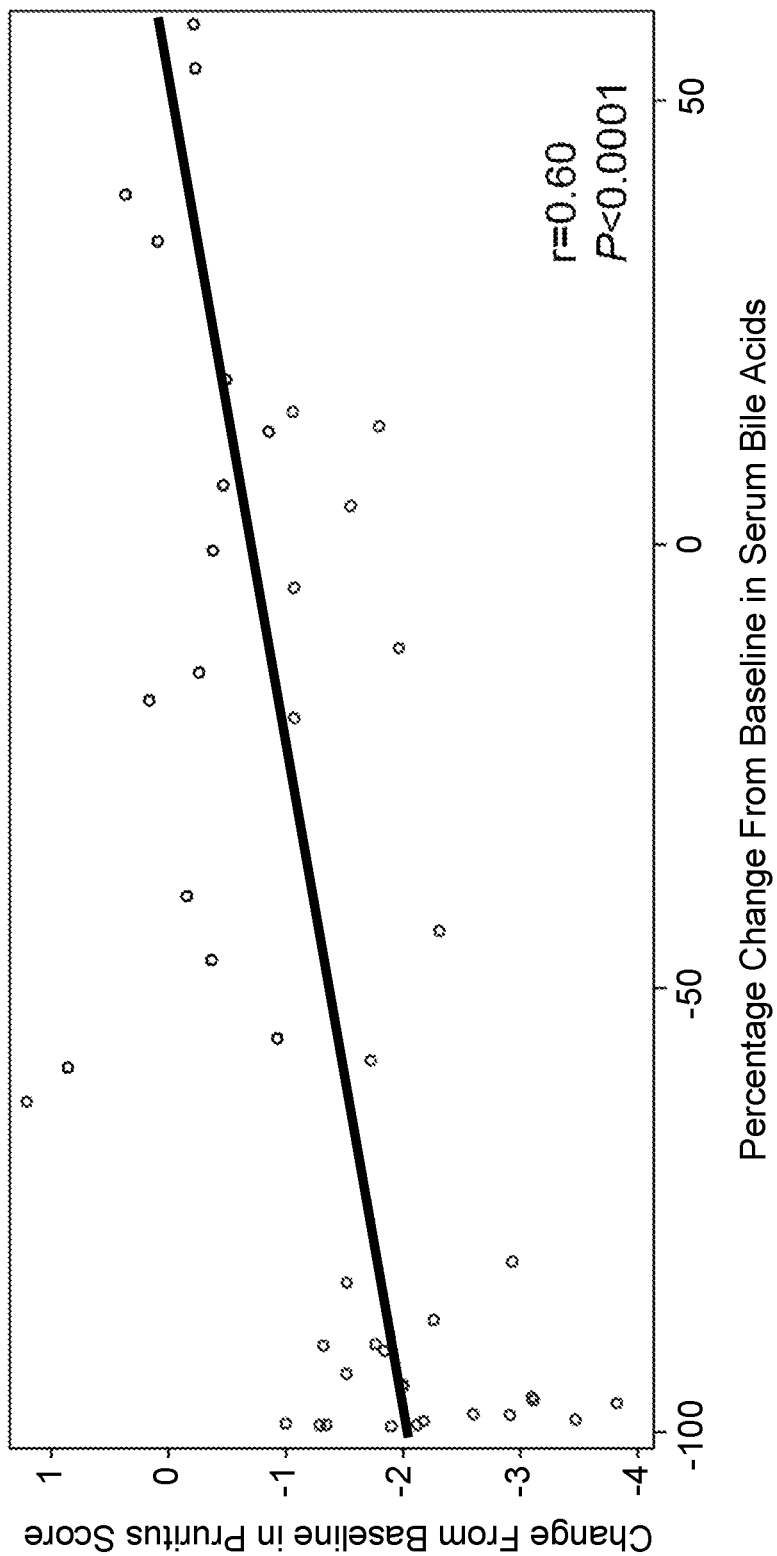
FIG. 19C is a graph of the change in pruritus vs the percentage change in serum bile acids.
Figure 19D:
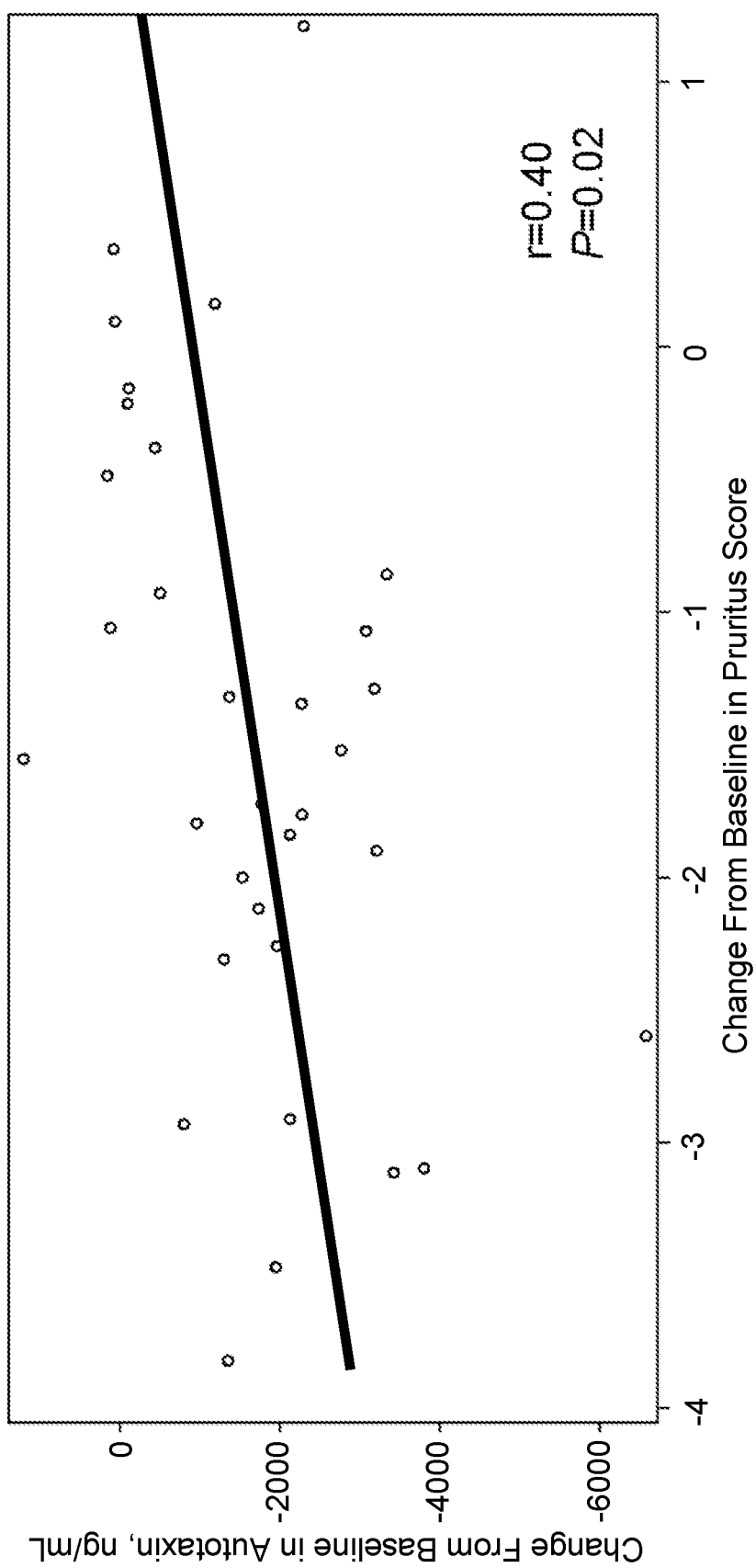
FIG. 19D is a graph of the change in autotaxin vs the change in pruritus.
Figure 19E:
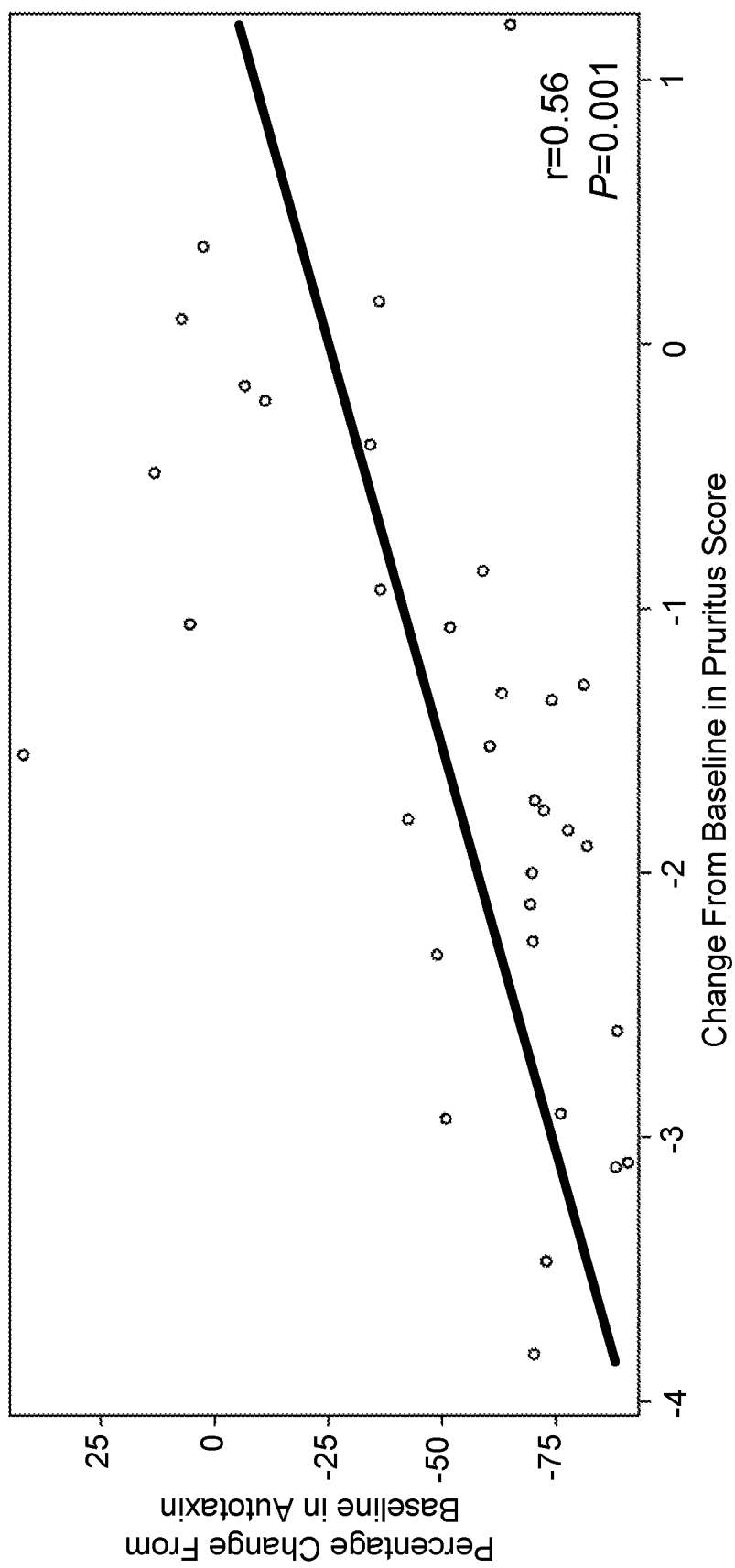
FIG. 19E is a graph of the change in autotaxin vs the change in pruritus.

At weeks 25-48, moderate-to-strong correlations were observed between percentage change from baseline in serum bile acids and absolute or percentage changes from baseline in autotaxin. See, FIGS. 18A and 18B (n=33, r, Pearson coefficient). There were moderate correlations between change from baseline in serum bile acids and autotaxin (FIG. 19A, n=33, r, Pearson coefficient) and moderate correlations between absolute or percentage changes from baseline in serum bile acids and changes from baseline in pruritus scores (FIGS. 19B and 19C, n=44, r, Pearson coefficient) at weeks 25-48. Moderate correlations also were observed between changes from baseline in pruritus scores and absolute or percentage changes from baseline in autotaxin. See, FIGS. 19D and 19E, n=33, r, Pearson coefficient).

Overall, odevixibat treatment reduced autotaxin, pruritus, and serum bile acids in patients with PFIC, and significant correlations were observed between reductions in each pair of these parameters.

Example 15—Efficacy and Safety Outcomes with Odevixibat in Children with PFIC Due to Deficiencies in Multidrug Resistance Protein 3 (PFIC Type 3) or Myson 5B (PFIC Type 6)

In the phase 3, randomized, placebo-controlled PEDFIC 1 study, odevixibat treatment reduced serum bile acids, improved pruritus, and was generally well tolerated in patients with PFIC1 or PFIC2. The ongoing open-label, phase 3 PEDFIC 2 study is assessing the effects of odevixibat in patients with any type of PFIC. In this example, the efficacy and safety outcomes are described for six patients with PFIC types other than PFIC1 and PFIC2. This subset of patients comprises 5 patients with PFIC3 and 1 with PFIC type 6 (PFIC6, resulting from mutation of the gene encoding myosin 5B [MYO5B]).

In PEDFIC 2, eligible patients are enrolled into one of 2 cohorts, based on the following criteria: Cohort 1 includes pediatric patients with PFIC1 or PFIC2 from PEDFIC 1 and cohort 2 includes patients of any age with any PFIC type; these are newly enrolled patients. In both cohorts, eligible patients are those with genetically confirmed PFIC, elevated serum bile acids (≥100 μmol/L), and significant pruritus (i.e., itching or scratching score of ≥2 per patient/caregiver report using the PRUCISION instrument). PEDFIC 2 includes a 72-week treatment period in which all patients receive oral, once-daily odevixibat 120 μg/kg. See also Example 2.

The following outcomes were assessed in patients with PFIC3 or PFIC6:

Change from baseline in serum bile acids, pruritus, hepatic biochemical parameters, growth, and sleep; serum bile acid response (i.e., serum bile acids reduced ≥70% or levels ≤70 μmol/L); proportion of positive pruritus assessments (PPAs) at the patient level (i.e., pruritus score ≤1 or a ≥1-point drop from baseline); and treatment-emergent adverse events (TEAEs). Patient pruritus and sleep were evaluated twice daily by caregivers using the validated PRUCISION scale; pruritus responses range from 0 to 4, with higher scores indicating worse symptom. Table 19 provides the patient demographics, baseline characteristics, and length of Odevixibat exposure. A total of 5 patients with PFIC3 (age range, 3.7-13.3 years) and 1 patient with PFIC6 (aged 12.8 years) were enrolled (Table 19). Mean (range) exposure was 41 (34-54) weeks for the 5 PFIC3 patients and 54 weeks for the 1 PFIC6 patient.

TABLE 19

Patient Demographics, Baseline Characteristics, and Odevixibat Exposure

| | Patient 1 (PFIC3) | Patient 2 (PFIC3) | Patient 3 (PFIC3) | Patient 4 (PFIC3) | Patient 5 (PFIC3) | Patient 6 (PFIC6) |
|---|---|---|---|---|---|---|
| Age, years | 5.0 | 11.2 | 13.3 | 6.1 | 3.7 | 12.8 |
| Sex | F | F | F | F | F | F |
| Serum bile acids, μmol/L | 363 | 168 | 125 | 119 | 288 | 169 |
| Pruritus score | 4.0 | 3.0 | 2.3 | 3.0 | 2.4 | 2.1 |
| Serum ALT, U/L | 115 | 72 | 111 | 94 | 47 | 50 |

TABLE 19-continued

Patient Demographics, Baseline Characteristics, and Odevixibat Exposure

|  | Patient 1 (PFIC3) | Patient 2 (PFIC3) | Patient 3 (PFIC3) | Patient 4 (PFIC3) | Patient 5 (PFIC3) | Patient 6 (PFIC6) |
|---|---|---|---|---|---|---|
| Total bilirubin, mg/dL | 2.6 | 1.7 | 1.7 | 1.7 | 1.1 | 6.0 |
| Odevixibat exposure, weeks | 34 | 54 | 38 | 39 | 41 | 54 |

From baseline to week 36 of odevixibat treatment, mean improvements were observed in serum bile acids, pruritus scores, height and weight Z scores, and most sleep parameters in patients with PFIC3 and PFIC6; mean changes in alanine aminotransferase and total bilirubin were somewhat more variable (see Table 20).

Over the interval from weeks 0-36, PPAs in 5 patients with available data (4 with PFIC3, 1 with PFIC6) were ≥85%; in 1 additional patient with PFIC3 with data over the interval from weeks 0-22, PPAs were 99%.

Odevixibat was generally well tolerated up to the data cutoff in PEDFIC 2 in patients with PFIC3 or PFIC6.

TABLE 20

Effect of Odevixibat Treatment in Patients with PFIC3 and PFIC6

|  | Patients with PFIC3 | | Patient with PFIC6 | |
|---|---|---|---|---|
|  | Mean (SE) baseline value N = 5 | Mean (SE) change from baseline to week 36 N = 4 | Baseline value (n = 1) | Change from baseline to week 36 N = 1 |
| Serum bile acids, μmol/L | 212 (48) | −91 (37) | 169 | −78 |
| Pruritus score | 2.9 (0.3) | −1.6 (0.4)[a] | 2.1 | −1.8[a] |
| Serum ALT, U/L | 88 (13) | 67 (21) | 50 | 89 |
| Total bilirubin, μmol/L | 30 (4) | 18 (13) | 102 | −83 |
| Height Z score | −2.0 (0.5) | 0.2 (0.2) | −2.5 | 0.1 |
| Weight Z score | −1.4 (0.6) | 0.1 (0.4) | −1.0 | 0.5 |
| % of days with bleeding associated with scratching | 18 (14) | 6 (6)[a] | 0 | 0[a] |
| % of days needing help falling asleep | 60 (21) | −29 (24)[a] | 21 | −21[a] |
| % of days needing soothing | 59 (20) | −28 (21)[a] | 36 | −36[a] |
| % of days sleeping with caregiver | 60 (21) | −27 (22)[a] | 0 | 0[a] |

[a]mean change to weeks 34-36

From baseline to last assessment, all patients with PFIC3 or PFIC6 had reductions in serum bile acids and all but 1 patient (PFIC3) had reductions in pruritus score. Three patients, including 2 with PFIC3 and 1 with PFIC6, met criteria for serum bile acid response at the last assessment.

Overall, 5 of 6 patients with PFIC3 or PFIC6 experienced any TEAS (Table 21). Most TEAEs were mild or moderate in severity. There were no serious TEAEs, TEAEs leading to discontinuation, or deaths.

TABLE 21

Summary of TEAEs in Patients with PFIC3 or PFIC6

|  | Patient1 (PFIC3) | Patient 2 (PFIC3) | Patient 3 (PFIC3) | Patient 4 (PFIC3) | Patient 5 (PFIC3) | Patient 6 (PFIC6) |
|---|---|---|---|---|---|---|
| TEAEs | 0 | 3 | 5 | 5 | 3 | 1 |
| Mild | 0 | 1 | 0 | 2 | 3 | 1 |
| Moderate | 0 | 2 | 4 | 0 | 0 | 0 |
| Severe | 0 | 0 | 1 | 3 | 0 | 0 |
| Serious TEAEs | 0 | 0 | 0 | 0 | 0 | 0 |
| TEAEs leading to discontinuation | 0 | 0 | 0 | 0 | 0 | 0 |
| Common TEAEs (occurring in ≥2 patients PFIC3 or PFIC6), by preferred term | | | | | | |
| ALT increased | 0 | 0 | 1 | 1 | 0 | 0 |
| Total bilirubin increased | 0 | 1 | 2 | 0 | 0 | 0 |

TABLE 21-continued

Summary of TEAEs in Patients with PFIC3 or PFIC6

| | Patient1 (PFIC3) | Patient 2 (PFIC3) | Patient 3 (PFIC3) | Patient 4 (PFIC3) | Patient 5 (PFIC3) | Patient 6 (PFIC6) |
|---|---|---|---|---|---|---|
| INR increased | 0 | 1 | 1 | 0 | 0 | 0 |
| Vitamin D deficiency | 0 | 0 | 0 | 1 | 2 | 0 |

Overall, patients with PFIC3 and PFIC6 experienced clinical benefits during up to 54 weeks of odevixibat treatment, including reductions in serum bile acids and improvement in pruritus symptoms, growth, and sleep parameters. Odevixibat treatment was generally well tolerated in patients with PFIC3 and PFIC6.

What is claimed is:

1. A method for treating progressive familial intrahepatic cholestasis (PFIC) in a subject in need thereof, the method comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean monthly pruritus score, and
   wherein the pharmaceutical formulation comprising odevixibat, or a pharmaceutically acceptable salt thereof, comprises a plurality of particles, wherein each particle is between about 0.1 and about 1.5 mm in size and comprises odevixibat, or a pharmaceutically acceptable salt thereof, in an amount of from about 0.1% w/w to about 5.0% w/w based on the total weight of the particle.

2. A method for treating pruritus associated with progressive familial intrahepatic cholestasis (PFIC) in a subject in need thereof, the method comprising orally administering to the subject a therapeutically effective amount of a pharmaceutical formulation comprising odevixibat, or a pharmaceutically acceptable salt thereof, wherein following administration of the pharmaceutical formulation, the subject exhibits a reduction in mean monthly pruritus score, and
   wherein the pharmaceutical formulation comprising odevixibat, or a pharmaceutically acceptable salt thereof, comprises a plurality of particles, wherein each particle is between about 0.1 and about 1.5 mm in size and comprises odevixibat, or a pharmaceutically acceptable salt thereof, in an amount of from about 0.1% w/w to about 5.0% w/w based on the total weight of the particle.

3. A method for reducing mean monthly pruritus score in a subject having progressive familial intrahepatic cholestasis (PFIC), the method comprising orally administering to the subject a therapeutically effective amount of a pharmaceutical formulation comprising odevixibat, or a pharmaceutically acceptable salt thereof, and
   wherein the pharmaceutical formulation comprising odevixibat, or a pharmaceutically acceptable salt thereof, comprises a plurality of particles, wherein each particle is between about 0.1 and about 1.5 mm in size and comprises odevixibat, or a pharmaceutically acceptable salt thereof, in an amount of from about 0.1% w/w to about 5.0% w/w based on the total weight of the particle.

4. The method of claim 1, wherein the reduction in mean monthly pruritus score is at least 0.5, at least 0.6, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, or at least 2.0.

5. The method of claim 1, wherein the reduction in mean monthly pruritus score is about 1.2 to about 2.0.

6. The method of claim 1, wherein the reduction in mean monthly pruritus score is about 1.6.

7. The method of claim 1, wherein the reduction in mean monthly pruritus score occurs following daily administration of the pharmaceutical formulation for at least 4 weeks, at least 8 weeks, at least 12 weeks, at least 16 weeks, at least 20 weeks, or at least 24 weeks.

8. The method of claim 1, wherein the PFIC is PFIC 1.

9. The method of claim 1, wherein the PFIC is PFIC 2.

10. The method of claim 1, wherein the PFIC is PFIC 3.

11. The method of claim 1, wherein the PFIC is PFIC6.

12. The method of claim 1, wherein the subject is a pediatric subject.

13. The method of claim 1, wherein the subject is administered 120 µg/kg/day of odevixibat, or a pharmaceutically acceptable salt thereof.

14. The method of claim 1, wherein the subject is administered 40 µg/kg/day of odevixibat, or a pharmaceutically acceptable salt thereof.

15. The method of claim 1, wherein the subject was odevixibat naive prior to the first administration of the pharmaceutical formulation comprising odevixibat, or a pharmaceutically acceptable salt thereof.

16. The method of claim 1, wherein each particle comprises odevixibat, or a pharmaceutically acceptable salt thereof, in an amount of from about 0.5% w/w to about 2.0% w/w based on the total weight of the particle.

17. The method of claim 16, wherein each particle comprises odevixibat, or a pharmaceutically acceptable salt thereof, in an amount of about 0.5% w/w based on the total weight of the particle.

18. The method of claim 1, wherein each particle comprises odevixibat, or a pharmaceutically acceptable salt thereof, in an amount of about 1.5% w/w based on the total weight of the particle.

19. The method of claim 1, wherein each particle comprises a core and a coating layer surrounding the core.

20. The method of claim 19, wherein the core comprises microcrystalline cellulose.

21. The method of claim 19, wherein the coating layer comprises odevixibat, or a pharmaceutically acceptable salt thereof.

22. The method of claim 19, wherein the coating layer is prepared by spraying onto the score a homogeneous suspension of odevixibat in water.

23. The method of claim 22, wherein the homogenous suspension does not contain agglomerates of odevixibat that are larger than 200 µm.

24. The method of claim 1, wherein the particles are between about 0.1 and about 1.0 mm in size.

25. The method of claim 1, wherein odevixibat is present as a hydrate of odevixibat.

26. The method of claim 25, wherein odevixibat is present as a sesquihydrate.

27. The method of claim 1, wherein each particle of the formulation substantially contains the same amount of odevixibat.

28. The method of claim 21, wherein the coating layer does not contain odevixibat agglomerates having a $d_{90}$ particle size distribution of greater than 15 μm.

29. The method of claim 4, wherein the reduction is mean monthly pruritus score is compared to a baseline score using an observer-reported outcome instrument.

\* \* \* \* \*

UNITED STATES PATENT AND TRADEMARK OFFICE
CERTIFICATE OF CORRECTION

PATENT NO. : 11,583,539 B2  
APPLICATION NO. : 17/548090  
DATED : February 21, 2023  
INVENTOR(S) : Per-Göran Gillberg et al.

Page 1 of 1

It is certified that error appears in the above-identified patent and that said Letters Patent is hereby corrected as shown below:

On the Title Page

Column 2 (Other Publications): Delete "(Oevixibat" and insert -- (Odevixibat --.

In the Claims

Column 74, Line 59: In Claim 22, delete "score" and insert -- core --.

Signed and Sealed this
Fifteenth Day of August, 2023

Katherine Kelly Vidal
*Director of the United States Patent and Trademark Office*